(12) United States Patent
Atkinson et al.

(10) Patent No.: US 9,365,597 B2
(45) Date of Patent: Jun. 14, 2016

(54) MITOCHONDRIA-TARGETED INHIBITORS OF CYTOCHROME C PEROXIDASE FOR PROTECTION FROM APOPTOSIS

(71) Applicants: Brock University, St. Catharines (CA); University of Pittsburgh—of the Commonwealth System of Higher Education, Pittsburgh, PA (US)

(72) Inventors: Jeffrey Atkinson, St. Catharines (CA); Jeffrey Stuart, St. Catharines (CA); Valarian E. Kagan, Pittsburgh, PA (US); Detcho A. Stoyanovsky, Pittsburgh, PA (US); Michael W. Epperly, Pittsburgh, PA (US); Joel S. Greenberger, Pittsburgh, PA (US); Hülya Bayir, Pittsburgh, PA (US)

(73) Assignees: University of Pittsburgh—Of the Commonwealth System of Higher Education, Pittsburgh, PA (US); Brock University, St. Catharines, Ontario (CA)

( * ) Notice: Subject to any disclaimer, the term of this patent is extended or adjusted under 35 U.S.C. 154(b) by 455 days.

(21) Appl. No.: 13/675,208

(22) Filed: Nov. 13, 2012

(65) Prior Publication Data

US 2013/0203829 A1 Aug. 8, 2013

Related U.S. Application Data

(60) Provisional application No. 61/558,235, filed on Nov. 10, 2011.

(30) Foreign Application Priority Data

Nov. 10, 2011 (CA) .................................... 2757917

(51) Int. Cl.
*C07F 9/6506* (2006.01)
*C07D 233/64* (2006.01)
*C07D 233/60* (2006.01)

(52) U.S. Cl.
CPC .......... *C07F 9/65061* (2013.01); *C07D 233/60* (2013.01); *C07D 233/64* (2013.01)

(58) Field of Classification Search
CPC .................................................. C07F 9/65061
See application file for complete search history.

(56) References Cited

U.S. PATENT DOCUMENTS

2007/0161544 A1 7/2007 Wipf et al.
2014/0018317 A1 1/2014 Wipf et al.

OTHER PUBLICATIONS

Atkinson et al. "A mitochondria-targeted inhibitor of cytochrome c peroxidase mitigates radiation-induced death" Nature Communications, 2011, vol. 2, Article 497, pp. 1-9.*

Garapati, Venkata Krishna, et al, Poster, "Protection from radiation-induced apoptosis: imidazole fatty acid conjugates that inhibit cytochrome c peroxidase", 21st Quebec-Ontario Minisymposium on Synthetic and Bioorganic Chemistry, Brock University, Nov. 12-14, 2010.
Ross, M.F., et al., "Lipophilic Triphenylphosphonium Cations as Tools in Mitochondrial Bioenergetics and Free Radical Biology", Biochemistry (Moscow), vol. 70, No. 2, 2005, pp. 222-230.
Hanai, Akira et al., "Induction of Apoptosis in Human Colon Carcinoma Cells HT29 by Sublethal Cryo-Injury: Mediation by Cytochrome C Release", Int. J. Cancer, 93, 2001, pp. 526-533.
Kagan, Valerian E. et al., "Mitochondria-targeted distruptors and inhibitors of cytochrom c/ cardiolipin peroxidase complexes", Mol Nutr. Food Res. Jan. 2009, 53(1), pp. 104-114.
Maddalena, Lucas Anthony, "Effectiveness of a Mitochondria-Targeted Inhibitor of Cytochrome c Peroxidase at Protecting Against Cell Death Induced by Cryopreservation and Oxygen-Glucose Deprivation", Thesis, Brock University, Aug. 2012.
Atkinson, Jeffrey et al., "A Mitochondria-targeted inhibitor of cytochrome c peroxidase mitigates radiation-induced death", Nature Communications, Oct. 11, 2011, pp. 1-9.
Tyurina, Yulia Y., "Oxidative lipidomics of hyperoxic acute lung injury: mass spectrometric characterization of cardiolipin and phosphatidylserine peroxication", Am. J. Physiol Lung Cell Mol Physiol, 299: L73-L85, 2010.
Fink, MP, et al., "Hemigrmicidin-TEMPO conjugates: novel mitochondria-targeted antioxidants", Crit. Care Med. Sep. 2007, 35(9 Suppl), S461-7.
De Boer, F., et al, "Extensive early apoptosis in frozen-thawed CD34-positivie stem cells decreases threshold doses for haematological recovery after autologous peripheral blood progenitor cell transplantation Bone marrow transplantation", Journal of Hematotherapy & Stem Cell Research, 29(3), 2002, p. 249-255.
Heng, B. C., et al., "Capase Inhibitor Z-VAD-FMK Enhances the Freeze-Thaw Survival Rate of Human Embryonic Stem Cells", Bioscience reports, 27(4-5), Oct. 2007, p. 257-264.
Heng, B.C. et al., "Loss of viability during free-thaw of intact and adherent human embryonic stem cells with conventional slow-cooling protocols is predominantly due to apoptosis rather than cellular necrosis", Journal of Biomedical Science, 13(3), May 2006, p. 433-445.
Ortega-Ferrusola, C., et al., "Detection of "Apoptosis-Like" Changes During the Cryopreservation Process in Equine Sperm", Journal of Andrology, 29(2), Jan. 2, 2013, p. 213-221.
Stroh, C., et al., "The role of caspases in cryoinjury: caspase inhibition strongly improves the recovery of cryopreserved hematopoietic and other cells", The FASEB Journal, 16(12), Aug. 7, 2002, p. 1651-1653.

* cited by examiner

*Primary Examiner* — Joseph Kosack
(74) *Attorney, Agent, or Firm* — Kathleen D. Rigaut; Dann, Dorfman, Herrell and Skillman

(57) ABSTRACT

The present application is directed to novel imidazole-substituted fatty acids that have been functionalized with an alkyl triphenylphosphonium group, compositions comprising these compounds and their use as inhibitors of cytochrome c peroxidase, in particular for the treatment and prevention of apoptosis.

21 Claims, 15 Drawing Sheets

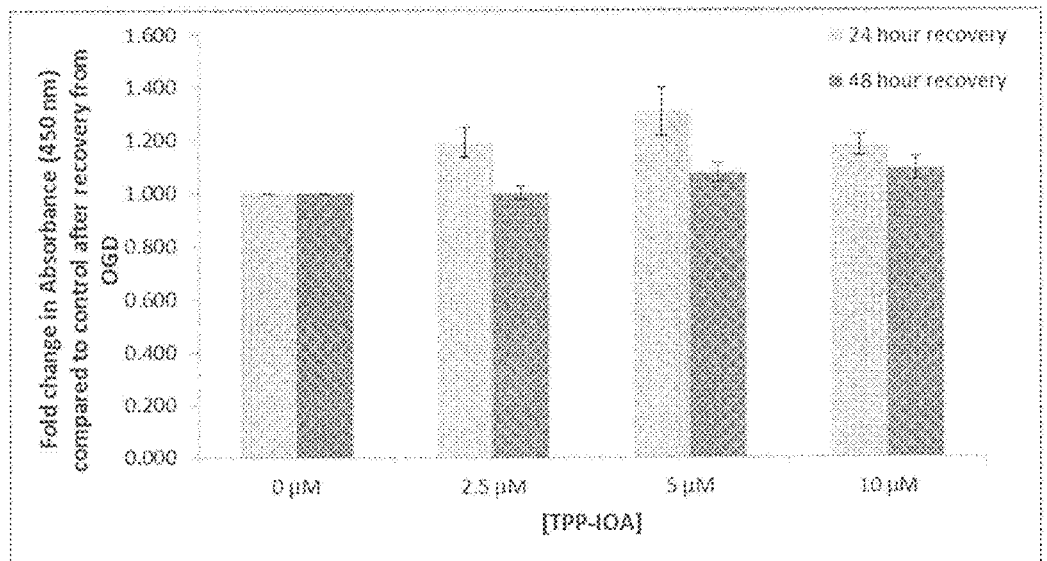

Figure 14
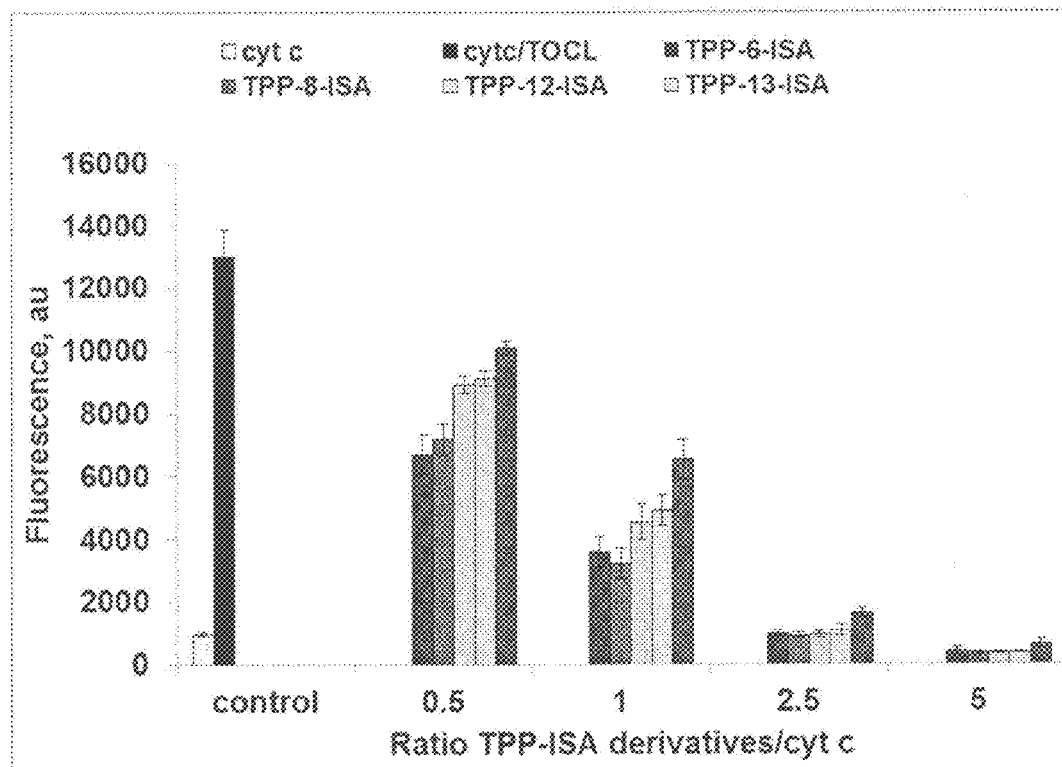
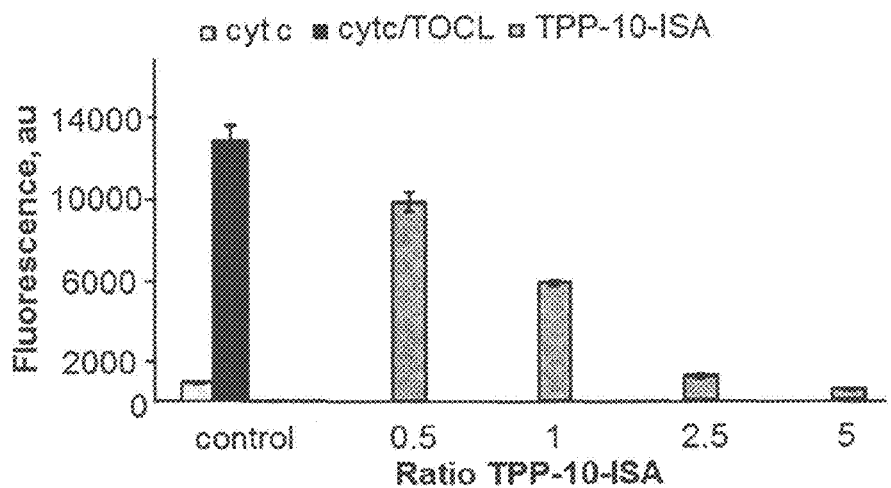

MITOCHONDRIA-TARGETED INHIBITORS OF CYTOCHROME C PEROXIDASE FOR PROTECTION FROM APOPTOSIS

CROSS-REFERENCE TO RELATED APPLICATIONS

The present application claims the benefit of priority from U.S. provisional application No. 61/558,235 filed on Nov. 10, 2011 and Canadian patent application no. 2,757,917 filed on Nov. 10, 2011, the contents of both of which are incorporated herein by reference in their entirety.

FIELD OF THE APPLICATION

The present application relates to novel compounds that inhibit cytochrome c (cyt c) peroxidase, compositions comprising these compounds and various uses thereof, for example for protection of cells from apoptosis. In particular, the present application relates to novel imidazole-substituted fatty acids and their use as cyt c peroxidase inhibitors.

BACKGROUND OF THE APPLICATION

Despite having evolved from organisms adapted to massive irradiation during the early development of Earth's biosphere, the human body—with its abundance of water—is vulnerable to radiolysis by high-energy (ionizing) irradiation. Medical applications of irradiation critically consider this sensitivity of normal tissues, particularly in the use of total body exposure for bone marrow transplantation patients. However, in uncontrolled situations of exposure to radiation, such as during a terrorist attack, or the unavoidable radiation exposure of flight crews during extended space missions, the development of protective measures is lagging behind, and there is an immediate need for the stockpiling of safe and effective radioprotectors/radiomitigators.

Acute radiation syndrome is associated with damage to the haematopoietic system and gastrointestinal tract due to massive cell loss in radiosensitive tissues occurring largely via apoptosis[1,2,3]. Along with radicals generated by radiolysis of water, the execution of mitochondria-mediated apoptosis is universally associated with the production of reactive oxygen species (ROS)[4,5]. Therefore, development of radiomitigators/radioprotectors for biodefense applications and radiotherapy has mostly focused on nonspecific thiol-based antioxidants that have shown clinically insignificant results[6,7,8].

Recently, ROS production has been identified as a required step in selective peroxidation of a mitochondria-specific phospholipid, cardiolipin (CL), whose oxidation products are essential for the outer membrane permeabilization and release of pro-apoptotic factors[4,9]. The catalyst of the peroxidation reaction is cytochrome c (cyt c) that forms a high-affinity complex with CL exhibiting potent peroxidase activity towards polyunsaturated CLs[9].

In normal mitochondria, CL and cyt c are spatially separated; the former is confined almost exclusively to the inner mitochondrial membrane, whereas the latter is located in the intermembrane space[10]. Early in apoptosis, CL migrates from the inner to the outer mitochondrial membrane—a process likely facilitated by one of the four candidate mitochondrial proteins: scramblase-3, nucleoside diphosphate kinase (NDPK-D), mitochondrial isoforms of creatine kinase (m-CPK) and t-Bid[11,12,13]. Trans-membrane re-distribution of CL makes physical interaction of CL and cyt c possible resulting in the formation of cyt c/CL complexes[9].

Several previous studies have proposed that there are two types of interaction of cyt c with anionic phospholipids; an electrostatic interaction and a specific hydrophobic interaction. Whereas the electrostatic interaction is mainly driven by the charges between the protein and anionic lipids, the hydrophobic interaction involves the insertion of the lipid acyl chain in a hydrophobic channel present in the structure of cyt c. It has been shown that both interactions are essential for initiating the peroxidase activity of cyt c[9] leading to peroxidation of bound polyunsaturated molecular species of CL. Notably, accumulation of peroxidized CL is essential for the execution of the apoptotic program. Conversely, prevention of CL peroxidation leads to inhibition of apoptosis[14].

Cyt-c-mediated apoptosis has also been associated with apoptosis in freeze-thaw treatment of cells (i.e. cryopreservation).[15]

Also, in instances of ischemic stroke, the border region of less severely affected brain tissue that surrounds the core necrotic area remains metabolically active following the ischemic event[16]. Many neurons in this region undergo apoptosis in the hours or days following the stroke event, thus there is potential to save such neurons through some form of post-stroke therapy that can suppress apoptosis.[16] Myocardial infarctions are another type of ischemic event that results in a similar manner of cell death.

Ischemia is pathological condition in which blood flow to cells of an organ or tissue is restricted for a period of time, subsequently followed by restoral of perfusion and associated reoxygenation.[17] During ischemia, the reduction in blood flow limits the supply of oxygen and glucose to cells and gradually leads to hypoxia/anoxia, resulting in an ultimate disruption of cellular homeostasis.[17] Re-establishment of blood flow restores oxygen and nutrient supply to cells, but causes further damage to cells.[17] For example, the burst of oxygen to cells after blood supply has been restored can cause an increased production of harmful reactive oxygen species (ROS) within mitochondria that may oxidize and damage macromolecules within the cell.[18] As a result of Ischemia/Reperfusion (I/R) injury, cell death occurs.[17]

Apoptosis is among the modes of cell death that occur in response to I/R.[17] Mitochondrial events appear to have important contributions to the apoptotic pathway associated with many kinds of I/R events, such as cerebral I/R and myocardial infarction.[19,20] Pro-apoptotic tBid appears to be an early activator of the mitochondrial pathway of apoptosis in both neuronal and focal cerebral I/R.[21] Cyt c and Smac/Diablo release from mitochondria, as well as caspase-9 and caspase-3 activation have also been reported to occur in response to cerebral I/R.[19]

Oxygen-glucose deprivation (OGD) appears to be an accepted model for in vitro studies of cerebral ischemia that is commonly used. This model was first developed by Goldberg and Choi[22], and involves the combined deprivation of oxygen and glucose followed by restoration of normal culture conditions to cultured neural cells roughly approximating the conditions of in vivo cerebral ischemia/reperfusion (I/R). Exposure of neural-like cells to OGD leads to patterns of cell death associated with cerebral ischemia[22], and so it can be used for the study of cell death mechanisms associated with cerebral ischemia or the effectiveness of potential protective strategies.

SH-SY5Y cells, a human neuroblastoma cell line, have been frequently used in OGD studies as a model of neuronal cell death associated with cerebral I/R. Fordel et al.[23] found that cell viability was 54% after 32 hour recovery from 16 hour OGD exposure, and a pattern of cell death just like that of in vivo cerebral ischemia was observed. That is, necrotic cell death predominantly occurred during OGD, while apoptotic death was greater following restoration of oxygen and glucose[23]. In another study, Wang et al.[24] exposed SH-SY5Y cells to varying times of OGD, and found that a 10-16 hour exposure decreased viability to cells to below 50% after 72 hours of recovery. Serra-Perez et al.[25] examined retinoic acid-differentiated SH-SY5Y cells in the context of OGD, and found that cyt c was present in the cytosol after 6 hours of reoxygenation following a 15 hour OGD period. Furthermore, an increase in the amount of apoptotic cells and caspase-3 activity was observed during the recovery period[25].

In contrast to the relatively long periods of OGD used in the above studies, Agudo-Lopez et al.[26] exposed SH-SY5Y cells to a much shorter period of OGD, lasting 3 hours in duration. After 16 hours of recovery, a 33% decrease in viability compared to cells not exposed to OGD was observed, along with a small percentage of cells at early apoptotic stages.

SUMMARY OF THE APPLICATION

In the present application, it was shown that the 'pro-oxidant' enzymatic activity of cyt c/CL complexes represents a target for anti-apoptotic drugs. Specifically, the peroxidase activity is due to CL-induced partial unfolding of the protein in the complex resulting in a 'loosened' liganding capacity of haem-iron by a distal $Met_{80}$[27]. The 'locking' of the haem-iron coordination bond with a strong ligand delivered through the hydrophobic channel to the immediate proximity of the haem catalytic site blocks the peroxidase activity, inhibiting CL peroxidation and preventing the progression of apoptosis. Indeed, it was demonstrated that mitochondria-targeted 3-hydroxypropyl-triphenylphosphonium (TPP)-conjugated imidazole-substituted fatty acids (TPP-IFAs) exert strong specific liganding of haem-iron in cyt c/CL complex, effectively suppressing its peroxidase activity and CL peroxidation, thus preventing cyt c release and cell death.

Accordingly, the present application includes a compound of Formula I:

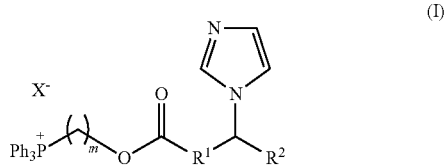

wherein:
m is 1, 2, 3, 4, 5, or 6;
$R^1$ and $R^2$ are independently selected from $C_{1-20}$alkylene and $C_{2-20}$alkenylene, provided that $R^1$ and $R^2$, together, comprise at least 10 carbon atoms; and
X is a counteranion, or
a stereoisomer or a solvate thereof.

The present application also includes a composition comprising one or more compounds of the application and a carrier. In particular the composition is a pharmaceutical composition and the carrier is pharmaceutically acceptable.

Also included in the present application is a method to inhibit cytochrome c (cyt c) peroxidase comprising administering an effective amount of one or more compounds of the application to a cell or subject in need thereof.

The present application also includes a use of one or more compounds of the application to inhibit cyt c peroxidase as well as a use of one or more compounds of the application to prepare a medicament to inhibit cyt c peroxidase. Also included are one or more compounds of the application for use to inhibit cyt c peroxidase.

By inhibiting cyt c peroxidase, the compounds of the application are able to protect cells from apoptosis. Accordingly, the present application also includes a method to prevent or treat apoptosis comprising administering an effective amount of one or more compounds of the application to a cell or subject in need thereof.

The present application also includes a use of one or more compounds of the application to prevent or treat apoptosis as well as a use of one or more compounds of the application to prepare a medicament to prevent or treat apoptosis. Also included are one or more compounds of the application for use to prevent or treat apoptosis.

Other features and advantages of the present application will become apparent from the following detailed description. It should be understood, however, that the detailed description and the specific examples while indicating embodiments of the application are given by way of illustration only. The scope of the claims should not be limited by the embodiments set forth in the examples, but should be given the broadest interpretation consistent with the description as a whole.

BRIEF DESCRIPTION OF THE DRAWINGS

The present application will now be described in greater detail with reference to the drawings in which:

FIG. 2A shows assessments of peroxidase activity of cyt c/TOOL by $H_2O_2$-induced oxidation of Amplex Red to resorufin. Data are means±s.d., n=4, *P<0.01 (Student's t-test) versus control (TOOL/cyt c/$H_2O_2$ with no ISA or IOA or IEOA or TPP-IOA or TPP-ISA added).

FIG. 2B shows a typical EPR spectrum of etoposide phenoxyl radicals (left panel), and assessments of peroxidase activity of cyt c/TOOL by $H_2O_2$-induced oxidation of etoposide using EPR spectroscopy (right panel).

FIG. 2C shows a typical low-temperature EPR spectrum of protein-immobilized (tyrosine) radicals (left panel), and assessments of protein-immobilized (tyrosine) radicals by low-temperature (77 K) EPR spectroscopy (right panel).

FIG. 2D shows a typical low-temperature (77 K) EPR spectrum of cyt c/TOOL complexes in the presence of Angeli's salt (left panel), and effects of ISA and IEOA on haem-nitrosylation of cyt c/TOOL induced by nitroxyl (HNO) generated from Angeli's salt (right panel). Data are means±s.d., n=3, *P<0.05 versus control (no ISA and IEOA added). ISA and IEOA limit accessibility of haem to small molecules.

FIG. 2E shows liquid-He EPR evidence for ligation change in cyt c haem-iron. X-band liquid-He (20 K) EPR spectra of cyt c.

FIG. 4A shows an HPLC-UV profile (solid lines) of mitochondrial extract from cells exposed to TPP-IOA (10 μM; incubation time, 30 min); dashed lines, standard solution of TPP-IOA (50 μM). Inset: overlapped UV spectra of the peaks reflecting the elution of a standard solution of TPP-IOA (Rt=4 min; dashed lines) and mitochondrial extract from mouse embryonic cells (solid lines).

FIG. 4B shows ESI-MS analysis of products formed during the hydrolysis of TPP-IOA in mitochondria.

FIG. 4C shows compartmentalization of TPP-IOA in mouse embryonic cells. The content of TPP-IOA was assessed by HPLC as described below. Data are means±S.E., n=3, *p<0.03 vs. whole cells or cytosol.

FIG. 4D shows the time course of TPP-IOA hydrolysis (closed circles) and accumulation of $(Ph)_3P^+C_3H_7OH$ (open circles) by cytosol (left panel) (1 mg protein/ml) and mitochondrial homogenates (right panel) (1 mg protein/ml). Incubations were carried out in 0.1 M phosphate buffer (pH 7.0) for 25 min at 37° C.; and reaction was stopped with $CH_3CN$ denatured proteins were centrifuged, and the supernatant was subjected to HPLC analysis. The volume of samples was 1 ml.

FIG. 6A shows typical ESI mass spectra of doubly charged molecular ions of non-oxidized TLCL and TLCL oxidized by CL/cyt c and $H_2O_2$. Mass-to-charge (m/z; negative MS mode) values of 723.5 and 731.5, 739.5, 747.5, 755.5, 763.5, 771.5 and 779.5 were assigned to molecular clusters of non-oxidized TLCL and TLCL enriched with 1-7 oxygen atoms, respectively.

FIG. 6B shows quantitative assessment of TLCL and its oxidation products by ESI-MS. Data are means±s.d., n=3, *P<0.05 (ANOVA) versus TLCL/cyt c/$H_2O_2$.

FIG. 7A shows the effect of TPP-ISA and TPP-IOA on γ-irradiation induced PS externalization (dark colour—Annexin V-positive, PI-positive cells; light colour—Annexin V-positive, PI negative cells) in mouse embryonic cells. Cells were γ-irradiated to a dose of 10 Gy, and then incubated in the presence of different concentrations of TPP-ISA or TPP-IOA for 48 h. Data are means±s.d., n=3. *P<0.01 (Student's t-test) versus irradiated only cells. TPP-ISA or TPP-IOA was added to cells 30 min after γ-radiation.

FIG. 7B shows the effect of TPP-ISA and TPP-IOA on γ-irradiation induced caspase 3/7 activation in mouse embryonic cells. Cells were γ-irradiated to a dose of 10 Gy, and then incubated in the presence of different concentrations of TPP-ISA or TPP-IOA for 48 h. Data are means±s.d., n=3. *P<0.01 (Student's t-test) versus irradiated only cells. TPP-ISA or TPP-IOA was added to cells 30 min after γ-radiation.

FIG. 7C shows the effect of TPP-ISA and TPP-IOA on γ-irradiation induced cyt c release from mitochondria into the cytosol (anti-cyt c antibody, 0.2 µg ml$^{-1}$, 1:3,000, Pharmmingen) in mouse embryonic cells. Cells were γ-irradiated to a dose of 10 Gy, and then incubated in the presence of different concentrations of TPP-ISA or TPP-IOA for 48 h. Data are means±s.d., n=3. *P<0.01 (Student's t-test) versus irradiated only cells. TPP-ISA or TPP-IOA was added to cells 30 min after γ-radiation.

FIG. 7D shows the effect of IEOA and ISA on actinomycin D-induced cell death in mouse embryonic cells. IEOA or ISA were incubated in the presence of fatty acid-free bovine serum albumin (BSA) (Sigma) at a molar ratio of 5:1 at 37° C. for 30 min. Mouse embryonic cells were incubated with IEOA/BSA or ISA/BSA (100 µM) complexes for 30 min before the addition of 100 ng ml$^{-1}$ actinomycin D (ActD). After 18-h incubation with ActD, cell viability was analysed by flow cytometry using an Annexin V/PI kit. ActD-induced cell death in ~34.2% of cells. Treatment of cells with ISA or IEOA in concentrations ranging from 1 to 100 µM exerted no detectable protection against ActD-induced cell death. Representative data with 100 µM IEOA/BSA and ISA/BSA complexes are shown. Data are means±s.d., n=3.

FIG. 7E shows the effect of TPP-ISA and TPP-IOA on caspase-3 activation in S-100 from mouse embryonic cells. Data are means±s.d., n=3.

FIG. 7F shows the effect of TPP-IOA on mouse lung endothelial cells treated with rotenone (apoptosis was assessed by PS externalization). Data are means±s.d., n=3. *P<0.05 (Student's t-test) versus rotenone challenged cells.

FIG. 7G shows the effect of TPP-ISA and TPP-IOA on clonogenic survival of mouse embryonic cells after γ-irradiation. The data were fitted to a single-hit multi-target model. Data are means±s.d., n=3. TPP-IOA or TPP-ISA was added to cells 30 min after γ-radiation.

FIG. 12 is a schematic showing the synthesis of TPP-conjugated, C-18 fatty acids with an imidazole substitution at carbons 13 and 14 of the carbon chain.

FIG. 13 shows the effects of TPP-IOA treatment on 24 & 48 hour viability, as assessed by the WST-1 cell proliferation assay, of SH-SY5Y cells exposed to an 8 hour period of OGD. After OGD, cells were incubated in growth media containing TPP-IOA until the indicated time of measurement. Bars represent mean±SEM fold change in absorbance at 450 nm compared to control cells that received no TPP-IOA treatment. The data obtained was from one experiment with n=7 or 8 for each sample group. * represents p-value <0.05 compared to the 24 hour recovery control group (Student's t-test).

FIG. 14A shows the effect of selected TPP-imidazole-stearic acid derivatives on peroxidase activity of cyt-c/TOCL complexes assessed by $H_2O_2$-dependent oxidation of Amplex Red. Conditions: cyt c (1 µM), $H_2O_2$ (50 µM), Amplex Red (50 µM). Experiments were performed in 20 mM HEPES buffer (pH 7.4) containing DTPA (100 µM), cyt c was incubated with DOPC/TOCL liposomes (1:1) at a ratio of TOCL: cyt c of 25:1.

FIG. 14B shows the effect of TPP-10-ISA on peroxidase activity of cyt c/TOCL complexes.

DETAILED DESCRIPTION OF THE APPLICATION

I. Definitions

Figure 1:
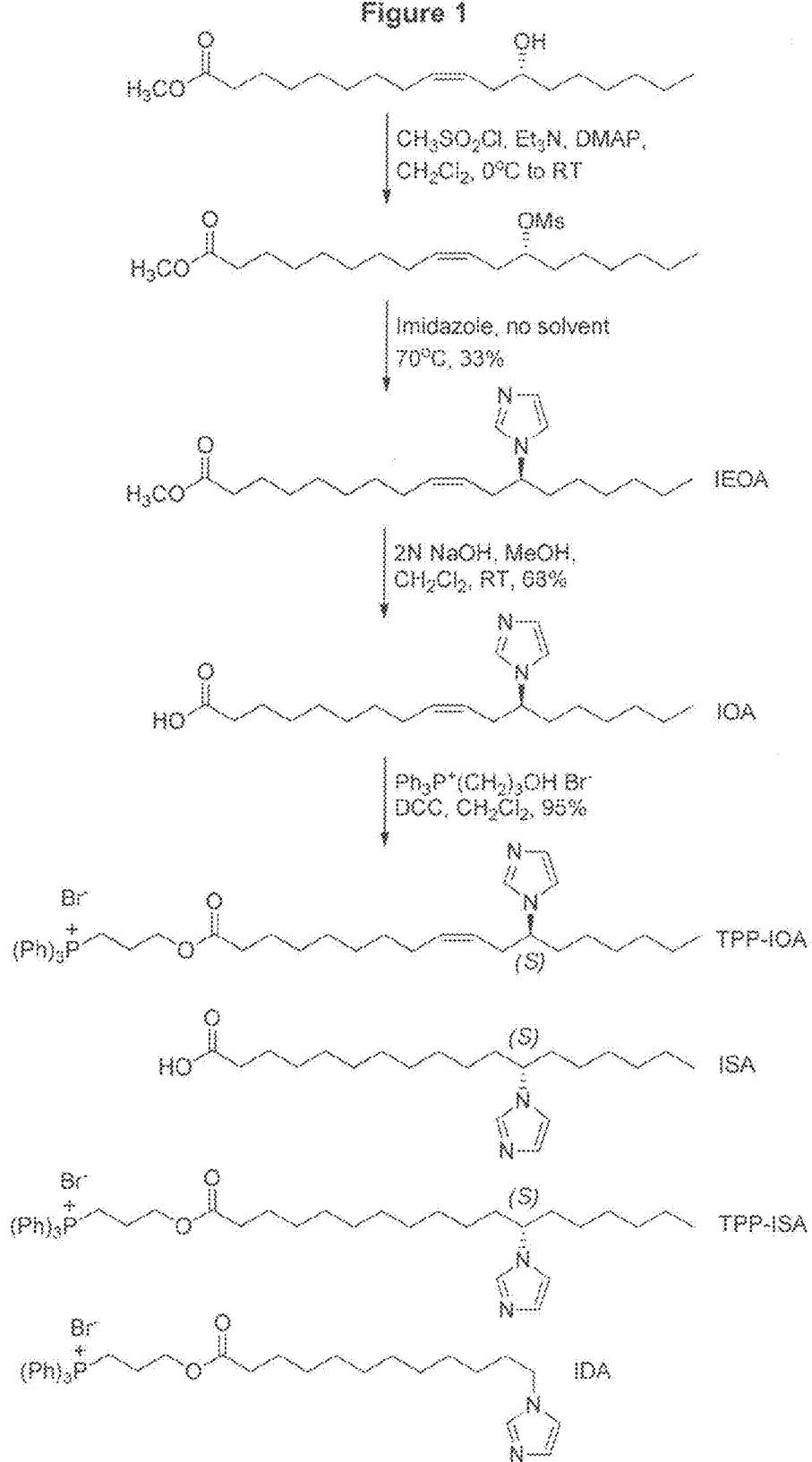
FIG. 1 shows a general synthetic method for synthesis of the compounds IEOA, IOA and TPP-IOA starting from ricinoleic acid as well as structures for ISA, TPP-ISA and IDA.

Unless otherwise indicated, the definitions and embodiments described in this and other sections are intended to be applicable to all embodiments and aspects of the disclosure herein described for which they are suitable as would be understood by a person skilled in the art.

As used in this application, the singular forms "a", "an" and "the" include plural references unless the content clearly dictates otherwise. For example, an embodiment including "a compound" should be understood to present certain aspects with one compound, or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the desired product. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "alkyl" as used herein means straight or branched chain, saturated alkyl groups, that is a saturated carbon chain. The term $C_{1-6}$alkyl means an alkyl group having 1, 2, 3, 4, 5, or 6 carbon atoms.

The term "acyl" as used herein means straight or branched chain, saturated acyl groups, that is a C(O)alkyl group. The term $C_{1-20}$alkyl means an alkyl group having 1, 2, 3, 4, 5, 6, 7, 8, 9, 10, 11, 12, 13, 14, 15, 16, 17, 18, 19 or 20 carbon atoms.

The term "alkylene" as used herein means straight or branched chain, saturated alkylene group, that is a saturated carbon chain that contains substituents on two of its termini. The term $C_{1-20}$alkylene means an alkylene group having 1, 2, 3, 4, 5, 6, 7, 8, 9, 10, 11, 12, 13, 14, 15, 16, 17, 18, 19 or 20 carbon atoms.

The term "alkenylene" as used herein means straight or branched chain, unsaturated alkenylene group, that is an unsaturated carbon chain that contains substituents on two of its termini. The term $C_{2-20}$alkylene means an alkylene group having 2, 3, 4, 5, 6, 7, 8, 9, 10, 11, 12, 13, 14, 15, 16, 17, 18, 19 or 20 carbon atoms and at least 1, for example, 1-8, 1-5, 1-4, 1-3, 1-2 or 1, double bonds.

The term "counteranion" as used herein means an atom or molecule having a negative charge that forms an ionic relationship with the positively charged phosphorus in the compounds of the application. The selection of counteranions would be well within the skill of a person in the art. If the compound of the application is to be used in therapy then the counteranion is pharmaceutically acceptable. Any counteranion that is compatible with the cationic portion of the compounds of the application is used.

The terms "protective group" or "protecting group" or the like as used herein refer to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, 3$^{rd}$ Edition, 1999 and in Kocienski, P. Protecting Groups, 3rd Edition, 2003, Georg Thieme Verlag (The Americas). Examples of suitable protecting groups include but are not limited to t-BOC, Ts, Ms, TBDMS, TBDPS, TMS, Tf, Ns, Bn, allyl, Fmoc, $C_{1-16}$acyl, $C_{1-6}$alkyl and the like.

t-Boc refers to the group t-butyloxycarbonyl.
Ts (tosyl) refers to the group p-toluenesulfonyl.
Ms refers to the group methanesulfonyl.
TBDMS refers to the group t-butyldimethylsilyl.
TBDPS refers to the group t-butyldiphenylsilyl.
TMS refers to the group trimethylsilyl.
Tf refers to the group trifluoromethanesulfonyl.
Ns refers to the group naphthalene sulphonyl.
Bn refers to the group benzyl.
Fmoc refers to the group fluorenylmethoxycarbonyl.
Allyl refers to the group with the structural formula $CH_2=CH-CH_2-$.

The term "subject" as used herein includes all members of the animal kingdom including mammals, and suitably refers to humans.

The term "cell" as used herein means a single cell or a plurality of cells.

The term "pharmaceutically acceptable" means compatible with the treatment of subjects, in particular humans.

The term "solvate" as used herein means a compound wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions.

The term "stereoisomers" as used herein refer to compounds which have their atoms connected in the same sequence but differ in the way the atoms are oriented in space—i.e. the difference between two stereoisomers lies only in the three dimensional arrangement of atoms. Stereoisomers can be classed as cis-trans isomers or optical isomers.

In embodiments of the application, the compounds described herein have at least one asymmetric centre giving optical isomers. Where compounds possess one asymmetric centre, they may exist as enantiomers. Where compounds possess more than one asymmetric centre, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (e.g. less than 20%, suitably less than 10%, more suitably less than 5%) of compounds of the application having alternate stereochemistry.

The term "cis-trans isomers", which are sometimes referred to as geometrical isomers, occur when double bonds prevent rotation of atoms around a bond. In a cis-isomer, both of the larger groups lie on the same side of the molecule. In the trans-isomer, the larger groups are on opposite sides of the molecule.

The term "compounds of the application" or "compounds of the present application" as used herein refers to a compound of Formula I or a solvate thereof, in particular, a pharmaceutically acceptable solvate thereof.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "Treatment" can also mean prolonging survival as compared to expected survival if not receiving treatment. "Treating" and "treatment" as used herein also include prophylactic treatment. For example, a subject to be treated with radiation can be treated to prevent damage caused by the radiation. Treatment also includes in vivo, in vitro and ex vivo treatment methods.

As used herein, the term "effective amount" or "therapeutically effective amount" means an amount effective, at dosages and for periods of time necessary to achieve the desired result. For example in the context of treating or preventing apoptosis, an effective amount is an amount that, for example, reduces the amount of apoptosis compared to the amount of apoptosis without administration of the compound. Effective amounts may vary according to factors such as the cause of the apoptosis, the disease state, age, sex and/or weight of the subject. The amount of a given compound that will correspond to such an amount will vary depending upon various factors, such as the given drug or compound, the pharmaceutical formulation, the route of administration, the cause of the apotosis, the type of condition, disease or disorder, the identity of the subject being treated, and the like, but can nevertheless be routinely determined by one skilled in the art.

As used herein, the terms "TPP-6-imidazole-stearic acid" and "TPP-6-ISA" refer to a compound of the following structure:

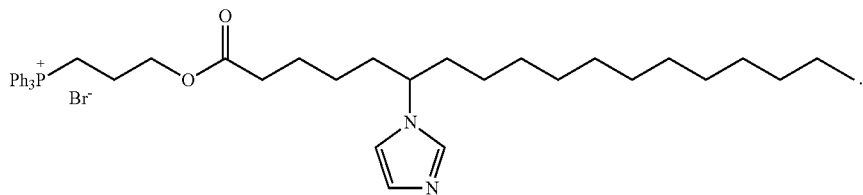

As used herein, the terms "TPP-8-imidazole-stearic acid" and "TPP-8-ISA" refer to a compound of the following structure:

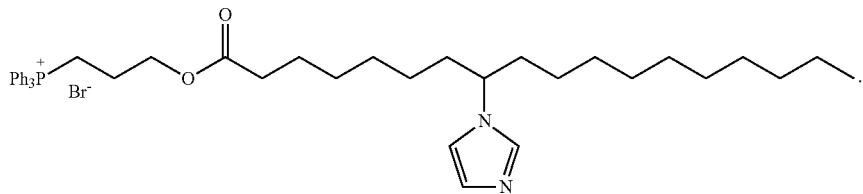

As used herein, the terms "TPP-10-imidazole-stearic acid" and "TPP-10-ISA" refer to a compound of the following structure:

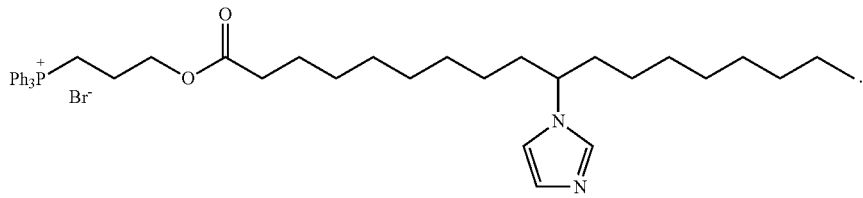

As used herein, the terms "TPP-12-imidazole-stearic acid", "TPP-12-ISA" and "TPP-ISA" refer to a compound of the following structure:

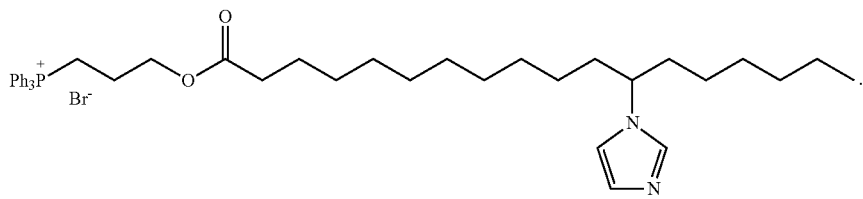

As used herein, the terms "TPP-13-imidazole-stearic acid" and "TPP-13-ISA" refer to a compound of the following structure:

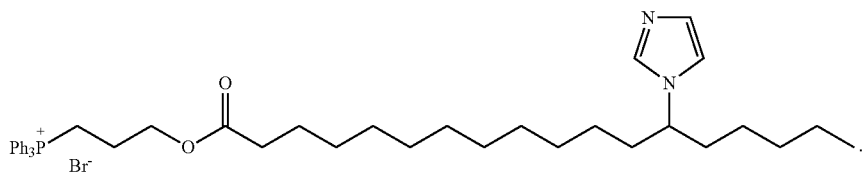

As used herein, the terms "TPP-14-imidazole-stearic acid" and "TPP-14-ISA" refer to a compound of the following structure:

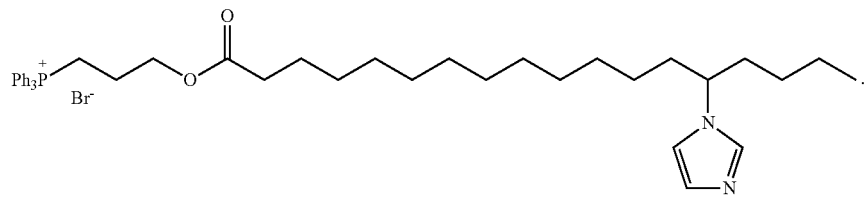

As used herein, the term "TPP-IOA" refers to a compound of the following structure:

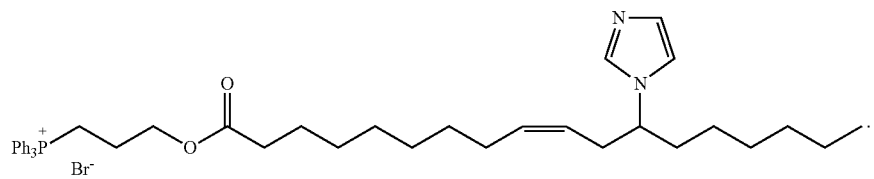

II. Compounds and Compositions of the Application

In the present application, a new class of mechanism-based mitochondria-targeted inhibitors that act as strong ligands of iron in complexes of cyt c with CL were designed, synthesized and explored. The compounds "lock" the catalytic site of the enzymatic complex, inhibiting its ability to facilitate the development of pro-apoptotic oxidative events, and suppress release of cyt c from mitochondria into the cytosol thus inhibiting apoptotic cell death. It was demonstrated that imidazole fatty acids specifically interact with partially unfolded cyt c and not with intact cyt c. Low-temperature (He) EPR experiments indicated that liganding of haem-iron in cyt c by IOA was dependent on the presence of CL.

Imidazole fatty acid (IFA) compounds were found to inhibit the peroxidase activity of isolated cyt c/TOCL complexes in vitro. While the IFA compounds also inhibited peroxidase activity in isolated mitochondria, the inhibition was less efficient than with the isolated cyt c/TOCL complexes. Further, when tested in cells, the IFA compounds showed no inhibition of peroxidase activity. In an effort to improve the in vivo bioavailability of the IFA compounds, the alkyltriphenylphosphonium esters of these compounds were prepared. While the triphenylphosphonium ion has been used previously to deliver compounds across the mitochondrion membrane,[28] prior to the studies of the present application, it was not known whether or not the TPP alkyloxy ester group would be hydrolyzed by esterases in the cell. Previous studies involved compounds with a TPP moiety which was not meant to be hydrolyzed. Advantageously, the studies of the present application showed that the ester in the TPP-IFA compounds was hydrolyzed, and the free IFAs were found to be concentrated in mitochondria. Further, surprisingly the TPP-IFA compounds of the present application exerted strong radioprotective/radiomitigative effects in vivo against lethal doses of irradiation of mice (from 1 h before through 24 h after the irradiation). The TPP-IFA compounds were also found to protect cells from cell death due to oxygen-glucose deprivation, a known model for ischemia.

Therefore, the present application includes a compound of Formula I:

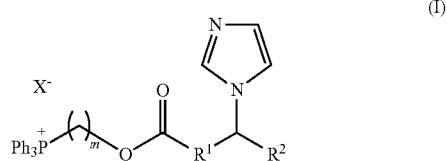

wherein:
m is 1, 2, 3, 4, 5, or 6;
$R^1$ and $R^2$ are independently selected from $C_{1-20}$alkylene and $C_{2-20}$alkenylene, provided that $R^1$ and $R^2$, together, comprise at least 10 carbon atoms; and
X is a counteranion, or
a stereoisomer or a solvate thereof.

In an embodiment of the application, m is 2, 3 or 4. In a further embodiment, m is 3.

In another embodiment of the application $R^1$ and $R^2$ are independently selected from $C_{4-15}$alkylene and $C_{4-15}$alkenylene, provided that $R^1$ and $R^2$, together, comprise at least 12 carbon atoms. In a further embodiment, $R^1$ is selected from $C_{4-15}$alkylene and $C_{4-15}$alkenylene and $R^2$ is selected from $C_{4-15}$ alkylene. In yet another embodiment, when $R^1$ or $R^2$ is alkenylene, it is an embodiment that it contains 1 or 2, suitably 1, double bond. In a further embodiment, the group, —$R^1$—C-(imidazole)-$R^2$ contains 17 carbons in the longest contiguous carbon chain. In another embodiment, this longest contiguous carbon chain is unbranched. In a further embodiment, the group, —C(O)—$R^1$—C-(imidazole)-$R^2$ is from oleic acid or stearic acid.

In an embodiment, $X^-$ is any suitable counteranion including both inorganic and organic anions. In an embodiment, this counteranion is pharmaceutically acceptable. Examples of suitable counteranions include, but are not limited to, the anions of hydrochloric acid, hydrobromic acid, sulfuric acid phosphoric acid, sodium monohydrogen orthophosphate, potassium hydrogen sulfate, glycolic acid, lactic acid, pyruvic acid, malonic acid, succinic acid, glutaric acid, fumaric acid, malic acid, tartaric acid, citric acid, ascorbic acid, maleic acid, benzoic acid, phenylacetic acid, cinnamic acid, salicylic acid and sulfonic acids such as p-toluene sulfonic and methanesulfonic acids. The resulting salts may exist in either a hydrated, solvated or substantially anhydrous form. In another embodiment, the counteranion is a halide, such as chloride or bromide.

The compounds of the application contain at least one asymmetric center where the imidazole is attached to the carbon chain and where the compound of Formula I contains at least one double bond, so there is the possibility for cis and trans regioisomers around that double bond. As mentioned previously, all stereoisomers and regioisomers, including mixtures thereof are within the scope of the present application. In an embodiment, the asymmetric center is substantially (e.g. greater than about 50%, about 60%, about 70%, about 80%, about 90%, about 95% or about 99%) in the S configuration and the double bond is in the cis or Z-configuration.

In an embodiment of the application, the compound of Formula I is selected from:

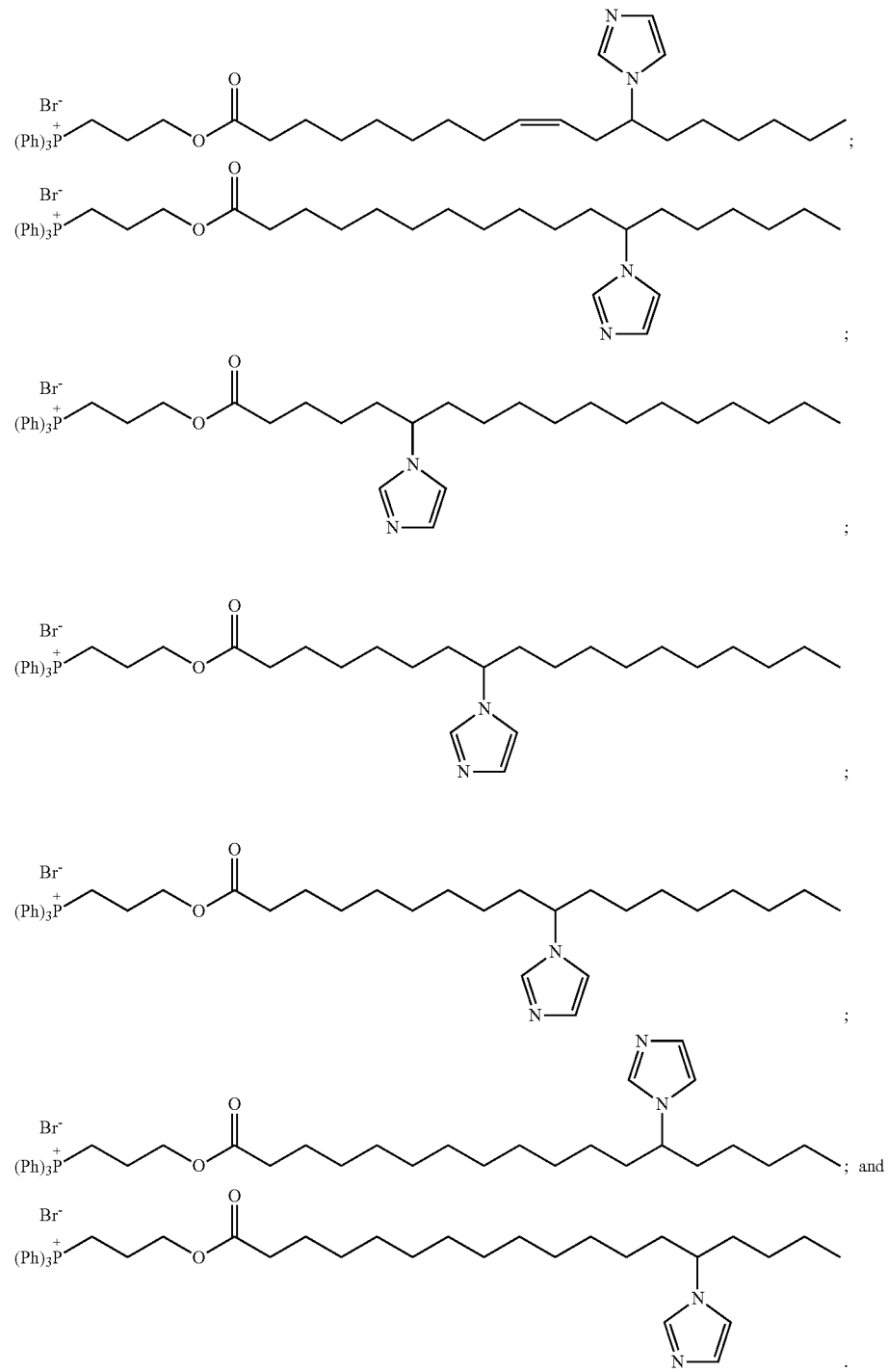

In another embodiment of the application, the compound of Formula I is selected from:

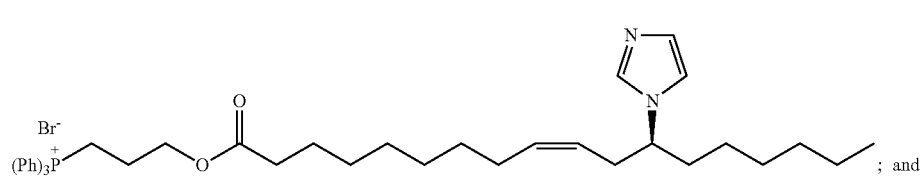
(TPP-IOA)

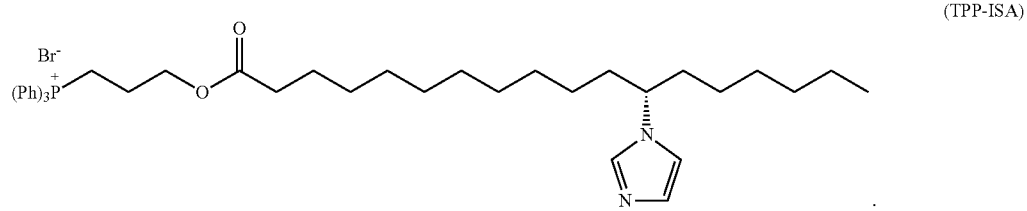
(TPP-ISA)

In another embodiment of the application, the compound of Formula I is selected from:

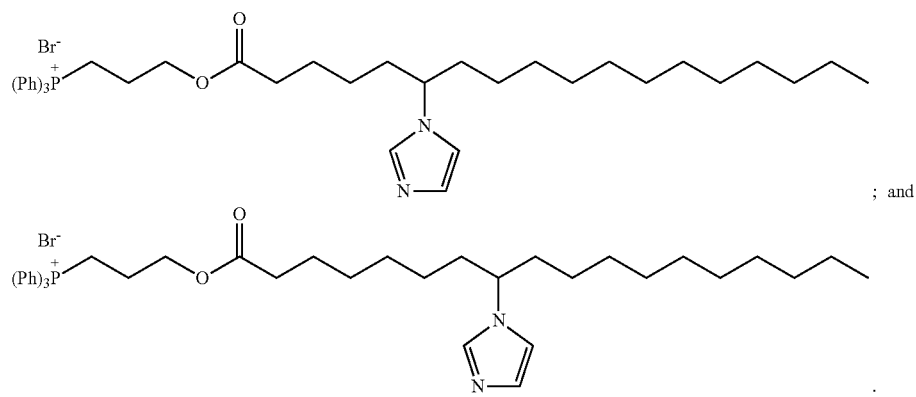

The compounds of the application may be formulated into compositions comprising the compound and at least one carrier. Suitably, the compounds of the application are formulated into pharmaceutical compositions for administration to subjects or cells in a biologically compatible form suitable for administration in vivo. Accordingly, the present application also includes a pharmaceutical composition comprising one or more compounds of the application and at least one pharmaceutically acceptable carrier.

The compounds of the application, may be administered to a subject in a variety of forms depending on the selected route of administration, as will be understood by those skilled in the art. A compound of Formula I, may be administered, for example, by oral, parenteral, buccal, sublingual, nasal, rectal, patch, pump or transdermal administration and the pharmaceutical compositions formulated accordingly. Conventional procedures and ingredients for the selection and preparation of suitable compositions are described, for example, in Remington's Pharmaceutical Sciences (2000-20th edition) and in The United States Pharmacopeia The National Formulary (USP 24 NF19) published in 1999.

A compound of Formula I, may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the compound may be incorporated with excipient and used in the form of ingestible tablets, buccal tablets, troches, capsules, elixirs, suspensions, syrups, wafers, and the like. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. Timed-release compositions can be formulated, e.g. liposomes or those wherein the active compound is protected with differentially degradable coatings, such as by microencapsulation, multiple coatings, etc. Liposome delivery systems, include, for example, small unilamellar vesicles, large unilamellar vesicles and multilamellar vesicles. Liposomes can be formed from a variety of phospholipids, such as cholesterol, stearylamine or phosphatidylcholines.

It is also possible to freeze-dry the compounds of the application and use the lyophilizates obtained, for example, for the preparation of products for injection.

A compound of Formula I, may also be administered parenterally. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time. Solutions of the compound can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Compounds of the application may also be delivered by the use of monoclonal antibodies as individual carriers to which the compound molecules are coupled. Compounds of the application may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, compounds of the application may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels. Still further the compounds of the application may be delivered by the use of nanoparticles.

III. Synthetic Methods

The compounds of the application may be prepared using methods generally known in the art from commercially available starting materials.

For example, compounds of Formula I are available by reacting a compound of Formula II, wherein X is as defined in Formula I, with a compound of Formula III, wherein $R^1$ and $R^2$ are as defined in Formula I, under standard, carboxylic acid activation, nucleophilic substitution reaction conditions as shown in Scheme 1.

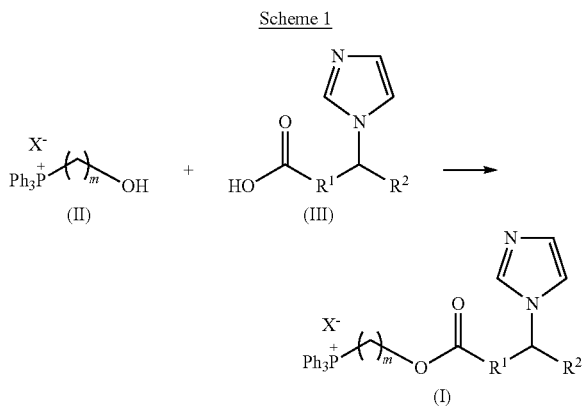

For example the carboxylic acid of the compound of Formula III is activated by conversion to an acid chloride, or by reaction with coupling reagents such as dicyclohexylcarbodiimide (DCC) and the like, and then reacted with the compound of Formula II, optionally in the presence of a non-nucleophilic base.

Figure 11:
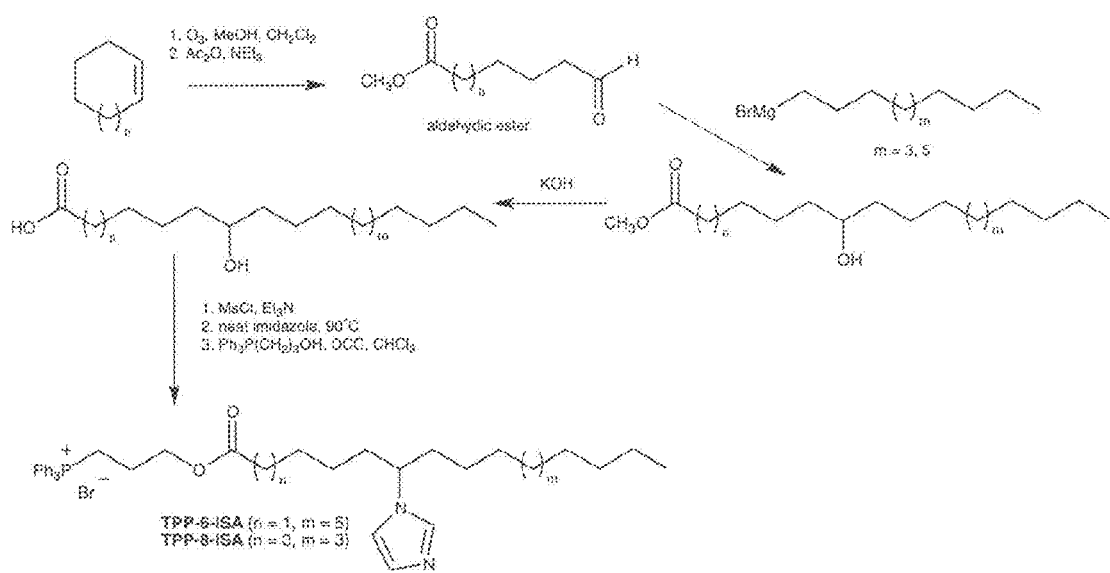
FIG. 11 is a schematic showing the synthesis of TPP-conjugated, C-18 fatty acids with an imidazole substitution at carbons 6 and 8 of the carbon chain by an ozonolysis methodology.

Compounds of Formula III wherein $R^1$ and $R^2$ are as defined in Formula I are, in one embodiment, derivable from hydroxyl substituted fatty acids, for example, ricinoleic acid. To prepare the compounds of Formula III, the carboxylic acid functional group is typically protected, for example as an ester, and the hydroxyl converted to a leaving group which is displaced by imidazole, either neat or in solution in the presence of a base. Removal of the carboxylic acid protecting group is then performed using known methods. In another embodiment, compounds of Formula I are available by cleaving a corresponding cycloalkenyl compound, for example with ozone, to obtain the corresponding aldehydic ester or derivative thereof. Addition of an alkyl Grignard reagent to the aldehyde provides the corresponding hydroxyl-substituted fatty acid ester, or derivative thereof, which can be converted to the imidazole-substituted fatty acid using the method described above. Examples of such methods to prepare compounds of Formula III are shown in FIGS. 11 and 12.

Compounds of Formula II, wherein X is as defined in Formula I, are either commercially available are prepared using methods known in the art. For example, triphenylphosphine is reacted with the corresponding alkanol having a suitable leaving group attached to a carbon at another location on the alkane chain. An example of a suitable leaving group is a halide, such as bromide. It should be noted that the leaving group becomes the counteranion "X". This counteranion may be maintained or exchanged at any stage during the preparation of the compounds of Formula I using known anion exchange methods.

IV. Methods and Uses of the Compounds of the Application

The compounds of the application are new, accordingly the present application includes all uses of these compounds, including their use as therapeutics, diagnostics or in screening assays.

In an embodiment, the present application includes a method to inhibit cytochrome c (cyt c) peroxidase comprising administering an effective amount of one or more compounds of the application to a cell or subject in need thereof.

The present application also includes a use of one or more compounds of the application to inhibit cyt c peroxidase as well as a use of one or more compounds of the application to prepare a medicament to inhibit cyt c peroxidase. Also included are one or more compounds of the application for use to inhibit cyt c peroxidase.

By inhibiting cyt c peroxidase, the compounds of the application are able to protect cells from apoptosis. Accordingly, the present application also includes a method to prevent or treat apoptosis comprising administering an effective amount of one or more compounds of the application to a cell or subject in need thereof.

The present application also includes a use of one or more compounds of the application to prevent or treat apoptosis as well as a use of one or more compounds of the application to prepare a medicament to prevent or treat apoptosis. Also included are one or more compounds of the application for use to prevent or treat apoptosis.

It is an embodiment of the application that the apoptosis is mitochondria-dependent apoptosis. In a specific embodiment of the present application, the apoptosis is induced by exposure of the subject or cell to radiation (i.e. radiation induced apoptosis). Accordingly, the compounds of the application are effective radioprotectants or radiomitigators. Therefore the present application also includes a method of preventing or treating radiation induced apoptosis comprising administering an effective amount of one or more compounds of the application to a subject or cell in need thereof.

The present application also includes a use of one or more compounds of the application to prevent or treat radiation induced apoptosis as well as a use of one or more compounds of the application to prepare a medicament to prevent or treat radiation induced apoptosis. Also included are one or more compounds of the application for use to prevent or treat radiation induced apoptosis.

The present application also includes a method of preventing or treating radiation damage comprising administering an effective amount of one or more compounds of the application to a subject or cell in need thereof. The present application also includes a use of one or more compounds of the application to prevent or treat radiation damage as well as a use of one or more compounds of the application to prepare a medicament to prevent or treat radiation damage. Also included are one or more compounds of the application for use to prevent or treat radiation damage. In an embodiment, the radiation damage is caused by exposure of the subject or cell to full-body irradiation (for example, for bone marrow transplantation), clinical radiation therapy (for example, for cancer therapy to protect healthy cells) or accidental radiation exposure.

In another specific embodiment of the application, the apoptosis is induced by subjecting a cell to a freeze/thaw cycle, for example, for cryopreservation. Accordingly, the present application also includes a method of treating or preventing freeze/thaw induced apoptosis comprising administering an effective amount of one or more compounds of the application to a cell in need thereof.

The present application also includes a use of one or more compounds of the application to prevent or treat freeze/thaw induced apoptosis as well as a use of one or more compounds of the application to prepare a medicament to prevent or treat freeze/thaw induced apoptosis. Also included are one or more compounds of the application for use to prevent or treat freeze/thaw induced apoptosis.

In another specific embodiment of the application, the apoptosis is induced by ischemia, for example, cerebral ischemia such as ischemic stroke or cardiac ischemia such as myocardial infarction and also ischemia affecting other vital organs (for example, the liver, kidney and gastrointestinal tract). Accordingly, the present application also includes a method of treating or preventing ischemia induced apoptosis comprising administering an effective amount of one or more compounds of the application to a subject or cell in need thereof.

The present application also includes a use of one or more compounds of the application to prevent or treat ischemia induced apoptosis as well as a use of one or more compounds of the application to prepare a medicament to prevent or treat ischemia induced apoptosis. Also included are one or more compounds of the application for use to prevent or treat ischemia induced apoptosis.

Other specific apoptosis-causing factors or stimuli that can be targeted using the compounds of the application, include, but are not limited to, traumatic brain injury, organ failure during sepsis, acute lung injury (e.g. hypoxia) and aging.

In an embodiment, treatment or prevention methods and uses disclosed herein also comprise assessing a subject for a condition or need for the treatment or prevention and administering the compound of the invention if the condition or need is present in the subject.

Treatment or prevention methods comprise administering to a subject or a cell, a therapeutically effective amount of one or more of the compounds of the application, and optionally consists of a single administration, or alternatively comprises a series of administrations. For example, the one or more compounds of the application are administered in a single administration any time prior to or following the apoptosis-inducing factor. For example, the one or more compounds of the application are administered immediately prior to the apoptosis-inducing factor or about 24 hours prior to the apoptosis-inducing factor, or any time in between, for example about 1 minute, about 10 minutes, about 30 minutes, about 1 hour, about 5 hours, about 10 hours or about 20 hours prior to the apoptosis-inducing factor. Alternatively, the one or more compounds of the application are administered immediately following the apoptosis-inducing factor or about 48 hours following the apoptosis-inducing factor, or any time in between, for example about 1 minute, about 10 minutes, about 30 minutes, about 1 hour, about 5 hours, about 10 hours, about 20 hours, about 24 hours, about 30 hours or about 36 hours, following the apoptosis-inducing factor.

However, in another embodiment, the compounds may be administered to the subject or cell in a series of administrations, for example about 1, 2, 3, 4, 5 or 6 times daily for 1 day to about 10 days either before or after the apoptosis-inducing factor. The length of the treatment period depends on a variety of factors, such as the cause of the apoptosis, severity of the condition, the age of the subject, the concentration of the compound, the activity of the compound, and/or a combination thereof. It will also be appreciated that the effective dosage of the compound used for the treatment or prevention may increase or decrease over the course of a particular treatment or prevention regime. Changes in dosage may result and become apparent by standard diagnostic assays known in the art. In some instances, chronic administration may be required. For example, the compounds are administered to the subject in an amount and for a duration sufficient to treat the subject.

The dosage of compounds of the application can vary depending on many factors such as the pharmacokinetic properties of the compound, the mode of administration, the age, health and weight of the recipient, the nature and extent of the symptoms, the frequency of the treatment and the type of concurrent treatment, if any, and the clearance rate of the compound in the subject to be treated. One of skill in the art can determine the appropriate dosage based on the above factors. Compounds of the application may be administered initially in a suitable dosage that may be adjusted as required, depending on the clinical response. As a representative example, oral dosages of one or more compounds of the application range between about 1 mg per day to about 1000 mg per day for an adult, suitably about 1 mg per day to about 500 mg per day, more suitably about 1 mg per day to about 200 mg per day. In an embodiment of the application, compositions are formulated for oral administration and the compounds are suitably in the form of tablets containing 0.25, 0.5, 0.75, 1.0, 5.0, 10.0, 20.0, 25.0, 30.0, 40.0, 50.0, 60.0, 70.0, 75.0, 80.0, 90.0, 100.0, 150, 200, 250, 300, 350, 400, 450, 500, 550, 600, 650, 700, 750, 800, 850, 900, 950 or 1000 mg of active ingredient per tablet.

Compounds of the application may be used alone or in combination with other known agents useful for treating or preventing diseases, disorders or conditions mediated by cyt c, including apoptosis. When used in combination with other agents, it is an embodiment that the compounds of the application are administered contemporaneously with those agents. As used herein, "contemporaneous administration" of two substances to a subject means providing each of the two substances so that they are both biologically active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. It is a further embodiment of the present application that a combination of agents is administered to a subject in a non-contemporaneous fashion.

The following non-limiting examples are illustrative of the present application:

EXAMPLES

General Materials and Methods for Examples 1 to 8

Reagents.

Unless indicated, all reagents used were purchased from Sigma (St. Louis, Mo.).

Cells.

Mouse embryonic cells (courtesy of Dr X. Wang, University of Texas, Dallas) were cultured in Dulbecco's Modified Eagle Medium (DMEM) supplemented with 15% fetal bovine serum (FBS), 25 mM Hepes, 50 mg per liter uridine, 110 mg per liter pyruvate, 2 mM glutamine, 1× nonessential amino acids, 50 μM β-mercaptoethanol, 0.5×10$^6$ Upper liter mouse leukaemia inhibitory factor, 100 Upper liter penicillin, and 100 mg per liter streptomycin in a humidified atmosphere of 5% $CO_2$, 95% air at 37° C. Mouse lung endothelial cells were obtained as previously described[29]. Briefly, lungs were flushed with Hank's balanced salt solution (HBSS) containing 10 U ml$^{-1}$ heparin, then homogenized and digested in type I collagenase using a gentle MACs dissociator (Miltenyi). Pulmonary endothelial cells were isolated by magnetic beads coated with antibody (rat anti-mouse) to PECAM-1 (BD Pharmingen), and seeded for subculture (passage 1). At approximately passage 2, cells were incubated with fluorescently labelled diacetylated low-density lipoprotein (LDL) followed by fluorescence-activated cell sorting (FACS) for further purification. The enriched PECAM and diacetylated LDL population was sub-cultured on a collagen/gelatin matrix in 2% $O_2$, 5% $CO_2$, 93% nitrogen in a Coy Hypoxic Glove Box/Chamber in Opti-MEM (Gibco), 10% FBS, 2 mM glutamine, 0.2% retinal-derived growth factor (Vec Technologies), 10 U ml$^{-1}$ heparin, 0.1 mM non-essential amino acid supplement (Gibco) and 55 μM β-mercaptoethanol (Counted as passage 3). Cells at passage 4-6 were applied to do the experiments.

Isolation of Mitochondria.

Mitochondrial fractions were isolated by differential centrifugation. Briefly, cells were suspended in mitochondria isolation buffer (pH 7.4; MIB) containing mannitol (210 mM), sucrose (70 mM), HEPES (10 mM), EDTA (1 mM) and protease inhibitor cocktail. Cells were lysed by Dounce homogenization. Unbroken cells, nuclei and debris were removed by 5 min centrifugation at 600×g at 4° C. Mitochondria, obtained by centrifugation at 10,000×g (10 min), were washed once with MIB.

Peroxidase Activity of cyt c.

Peroxidase activity of cyt c was assessed by oxidation of Amplex Red, etoposide or TLCL (tetra-linoleoyl-cardiolipin). Measurements of Amplex Red oxidation were performed using fluorescence of its oxidation product resorufin. Cyt c (1 μM) was incubated with tetra-oleoyl-cardiolipin (TOCL) containing liposomes (CL/cyt c ratio 25:1). Then 50 μM Amplex Red and 50 μM $H_2O_2$ were added, and the incubation proceeded for an additional 20 min. Fluorescence was detected by employing a "Fusion α" universal microplate analyzer and by using an excitation wavelength of 535 nm and an emission wavelength of 590 nm. EPR spectra of etoposide phenoxyl radicals were recorded at 25° C. in gas permeable Teflon tubings (inner diameter, 0.8 mm; thickness, 0.013; Alpha Wire Corp., Elizabeth, N.J.). Volume of samples was 60 μL. The spectra were recorded under the following conditions: 335.3 mT, center field; 2 mT, sweep width; 0.04 mT, field modulation; 10 mW, microwave power; 0.1 s, time constant; 2 min, time scan. The time course of the etoposide radical EPR signal was obtained by repeated scanning of the field (0.15 mT, sweep width; 335.3 mT, center field) corresponding to a part of the EPR signal. Peroxidase activity of mitochondria was determined by the formation of resorufin from Amplex Red. Isolated mouse liver mitochondria (0.6 mg/ml) were incubated in the presence of 100 μM Amplex Red and 2 mM tert-butyl hydroperoxide (tBOOH). After incubation at room temperature for 20 min, fluorescence of resurufin was measured.

Assessment of Oxidized Molecular Species of CL by Mass Spectrometry.

For measurement of TLCL oxidation, cyt c (4 μM) was incubated with TLCL (100 μM) containing liposomes (TLCL/cyt c ratio-20:1) and $H_2O_2$ (80 μM) for 10 min at 37° C. The reaction was stopped by catalase (150 units/ml) and CL was extracted using Folch procedure[37]. Analysis of (hydroperoxy- and hydroxy-) oxidized phospholipid species was performed as described[30]. TLCL and its oxidized molecular species were extracted by the Folch procedure[37] and separated on a normal phase column (Luna 3 μm Silica 100A, 150×2 mm, Phenomenex, Torrance Calif.). Analytes were eluted at a flow rate of 0.2 mL/min using gradient of solvents A (chloroform:methanol: ammonium hydroxide (28%), 80:19.5:0.5 (v/v)) and B (chloroform:methanol: water:ammonium hydroxide, 60:34:5:0.5 (v/v))[31]. The column was flashed for the first 3 min isocratically with solvent B (10%), 3-15 min with a linear gradient from 10% solvent B to 37% solvent B, 15-23 min following a linear gradient to 100% solvent B, and then 23-45 min isocratically at 100% solvent B, 47-57 min isocratic at 10% solvent B for equilibrium column. To assess oxidized molecular species of CL, electrospray-ionization-liquid chromatography mass-spectrometry (LC/ESI-MS) was performed using a Dionex Ultimate™ 3000 HPLC coupled on-line to an ESI ion source and a linear ion trap mass spectrometer (LXQ Thermo-Fisher) with the Xcalibur operating system (Thermo Fisher Scientific, San Jose, Calif.). The ESI probe was operated at a voltage differential of 3.5-5.0 kV in the negative ion mode. Capillary temperature was maintained at 150° C. Using range zoom (200-2000 m/z) in negative ion mode, the centroid spectra were acquired.

Assessment of Imidazole Substituted Fatty Acids by Mass Spectrometry.

Mass spectral analysis of TPP-IOA was performed with a Finnigan LCQ Duo mass spectrometer (ThermoFisher Scientific, Co. West Palm Beach, Fla.). To exclude interference from $LiClO_4$, HPLC fractions were collected and analytes were extracted following the Folch procedure[37]. The dry residues obtained after evaporation of the organic phase were re-dissolved in $CH_3OH$ and the corresponding solutions were directly infused in the mass spectrometer. For MS analysis of (E)-12-(1H-imidazol-1-ium-1-yl)octadec-9-enoic acid, the methanolic solution was supplemented with $CH_3COOH$ (1%). All mass spectra were recorded in positive mode.

Preparation of Small Unilamellar Liposomes.

Small unilamellar liposomes were prepared from dioleoylphosphatidylcholine (DOPC) and TOCL (1:1 ratio) or DOPC and TLCL (4:1 ratio) by sonication in HEPES buffer (20 mM with 100 μM diethylene triamine pentaacetic acid (DTPA) (pH 7.4) 3×60 sec, relaxation time 2 min, 4° C.).

Statistics.

For the in vitro experiments, the results are presented as means±s.d. values from at least three experiments, and statistical analyses were performed by either paired/unpaired Student's t-test or one-way ANOVA. As an exploratory analysis, P-values were not adjusted for multiple comparisons. For the survival data, median survival and its 95% confidence interval were calculated for each group, and the two-sided log-rank test was used to examine the differences between irradiated mice and irradiated mice treated with TPP-ISA or TPP-IOA. In all these tests, a P-value of <0.05 was regarded as significant.

Example 1

General Procedure for the Synthesis of Triphenylphosphonium-Conjugated Imidazole-Substituted Fatty Acids A general synthetic method is shown for synthesis of conjugates starting from ricinoleic acid in FIG. 1, which is identical to that used for the reduced form (12-hydroxystearic acid).

The synthesis of imidazole-substituted fatty acids and their esters relied on the ready availability of the naturally occurring fatty acid (9Z,12R)-(+)-ricinoleic acid. For initial studies the 12-OH group offered a site for heterocycle substitution on a long chain fatty acid without having to prepare new starting materials. Reduced ricinoleic acid (12-hydroxystearic acid) and the natural product ricinoleic acid (Pfaltz and Bauer, Inc.) were both purchased from VWR (Canada). Methyl 12-hydroxyoctadecanoate (methyl 12-hydroxystearate) was purchased from Aldrich (Oakville, ON). The mesylates were used crude as they tended to decompose when chromatographed on silica.

(a) Methyl (12-methanesulfonyloxy)-dihydroricinoleate

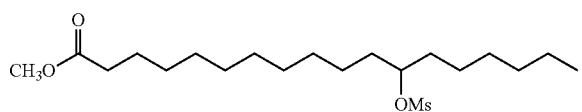

Methyl 12-hydroxyoctadecanoate 9.24 g (29.4 mmol) and 4-dimethylaminopyridine (507.2 mg, 4.16 mmol) were dissolved in 150 mL of dichloromethane. Under a nitrogen atmosphere, triethylamine (6.2 mL, 44.56 mmol) and methane sulfonyl chloride (3.4 mL, 44 mmol) were added to the mixture. The mixture was left to stir on an ice bath for 20 minutes, and then over night at room temperature. The reaction solution was diluted with 50 mL dichloromethane, and neutralized with 100 mL $NaHCO_3$ in water. The sample was washed 3×50 mL with water, and the organic layer was collected and dried with anhydrous magnesium sulfate and evaporated under reduced pressure to yield a crude dark yellow oil (~12 g) which was used crude in the next step.

(b) Methyl 12-(1H-imidazol-1-yl)octadecanoate

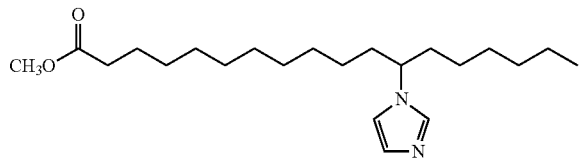

Methyl (12-methanesulfonyloxy)-dihydroricinoleate (5.94 g, 14.5 mmol) was combined with imidazole 2.01 g (29.5 mmol) in a round bottom flask. The solventless mixture was left to stir overnight at 70° C. The material was purified via column chromatography on silica (hexane:ethyl acetate, 1:1) to yield 2.22 g (6.09 mmol, 42.0%) of a dark yellow oil.

$R_f$=0.45 ($CHCl_3$, iodine and $KMnO_4$ stain). $^1H$ NMR (300 MHz, $CDCl_3$) δ 7.43 (s, 1H), 7.05 (s, 1H), 6.86 (s, 1H), 3.73 (quintet, 1H), 3.64 (s, 3H), 2.27 (t, 2H), 1.68 (m, 4H), 1.59 (m, 2H), 1.30-1.10 (m, 22H), 0.83 (t, 3H); $^{13}C$ NMR ($CDCl_3$) 174.1, 136.2, 129.2, 116.1, 58.4, 51.2, 36.1, 33.8, 31.3, 29.1, 29.1, 28.9, 28.8, 28.6, 25.8, 25.8, 24.7, 22.3, 13.7; MS (FAB)

m/z 364 (M+, 100%), 346 (12%), 333 (19%), 298 (10%), 291 (23%), 280 (21%), 279 (98%), 207 (10%), 179 (11%), 165 (100%), 150 (17%).

(c) 12-(1H-imidazol-1-yl)octadecanoic acid

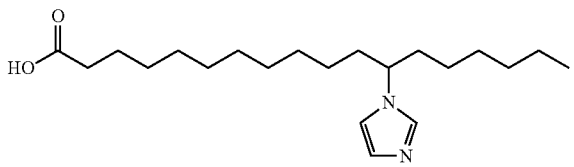 [SMILES: CCCCCCC(CCCCCCCCCCC(=O)O)n1ccnc1]

Methyl 12-imidazol-1-yl-dihydroricinoleate (1.43 g, 3.92 mmol) was combined with 10 mL 2N NaOH/MeOH in 50 mL dichloromethane. The mixture was left to stir for 3 days at room temperature. Solvent was removed under reduced pressure. 50 mL of water was added and the mixture was extracted with 50 mL ether. The aqueous layer was removed and acidified to pH 5 with 1N HCl. The aqueous layer was then extracted with 3×50 mL dichloromethane. Both the dichloromethane and ether layers were collected and washed with 50 mL saturated NaCl solution and again with 50 mL water. The organic layer was collected and dried with magnesium sulfate, and evaporated to give a crude yield of 1.34 g (3.83 mmol, 97.5%). The material was then purified via column chromatography on silica (dichloromethane:methanol 9:1) to yield 1.19 g (3.38 mmol, 86.3%).

$R_f$=0.44 (dichloromethane:methanol 9:1, iodine, KMnO$_4$ stain). $^1$H NMR (300 MHz, CDCl$_3$) δ 12.17 (s, 1H), 7.66 (s, 1H), 7.10 (s, 1H), 6.87 (s, 1H), 3.87 (m, 1H), 2.29 (t, 2H), 1.66 (m, 6H), 1.19 (broad m, 23H), 0.84 (t, 3H); $^{13}$C NMR (CDCl$_3$) δ 136.0, 127.5, 116.6, 59.2, 53.4, 36.1, 31.5, 29.2, 29.13, 29.07, 29.0, 28.8, 25.9, 25.9, 25.0, 22.4, 13.9; MS (EI) m/z 349 (M+, 9%), 306 (22%), 291 (15%), 266 (25%), 265 (96%), 263 (12%), 207 (12%), 166 (23%), 165 (100.0%).

(d) Methyl 12-(imidazol-1-yl)-(Z)-octadec-9-enoate

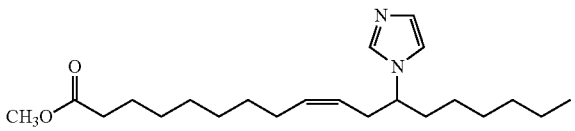

Methyl 12-methanesulfonyloxy-(Z)-octadec-9-enoate (16.12 g, 40.9 mmol) was combined with imidazole (5.40 g, 29.5 mmol) in a round bottom flask. The mixture was left to stir overnight at 70° C. The material was purified via column chromatography (hexane:ethyl acetate 1:1) to yield 4.88 g (13.5 mmol, 33.0%) of a dark yellow oil.

$R_f$=0.45 (CHCl$_3$, iodine and KMnO$_4$ stain). $^1$H NMR (300 MHz, CDCl$_3$) δ 7.45 (s, 1H), 7.03 (s, 1H), 6.90 (s, 1H), 5.48-5.3 (m, 2H), 3.80 (m, 1H), 3.63 (s, 3H), 2.42 (m, 2H), 2.27 (t, 2H), 1.65-1.40 (broad m, 22H), 0.83 (t, 3H); $^{13}$C NMR (CDCl$_3$) δ 174.2, 136.1, 133.4, 128.7, 121.7, 116.7, 51.3, 36.4, 35.3, 34.1, 33.9, 31.4, 29.2, 28.9, 28.7, 27.1, 25.9, 24.7, 22.4, 22.3, 13.9; MS (EI) m/z 365 (M+100%) 333 (19.2%), 291 (23.7%), 280 (21.0%), 278 (97.8%), 166 (21.2%), 165 (100.0%), 109 (10.2%), 97 (13.8%), 96 (12.6%), 95 (21.2%), 74 (31.9%), 69 (97.2%), 55 (40.2%).

(e) 12-(Imidazol-1-yl)-(Z)-9-octadecaenoate

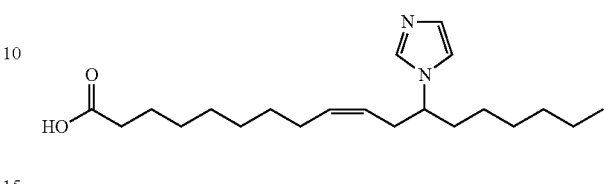

Methyl 12-(imidazol-1yl)-(Z)-octadec-9-enoate) 4.8 g (13.5 mmol) was combined with 10 mL 2N NaOH/MeOH in 75 mL dichloromethane. The mixture was left to stir for 3 days at room temperature. Solvent was removed under reduced pressure. 50 mL of water was added and the mixture was extracted with 50 mL ether. The aqueous layer was removed and acidified to pH 5 with 1N HCl. The aqueous layer was then extracted with 3×50 mL dichloromethane. The organic layers were collected, washed with 50 mL saturated NaCl solution, 50 mL water, dried with magnesium sulfate, and evaporated to give a crude yield of 4.02 g (11.55 mmol, 85.7%). The material was then purified via column chromatography (dichloromethane:methanol 10:1) to yield 3.19 g (9.18 mmol, 68.1%).

$R_f$=0.42 (dichloromethane:methanol 10:1, iodine, KMnO$_4$ stain). $^1$H NMR (300 MHz, CDCl$_3$) δ 11.45 (s, 1H), 8.74 (s, 1H), 7.30 (s, 1H), 7.09 (s, 1H), 5.40 (m, 1H), 5.13 (m, 1H), 4.24 (quintet, 1H), 2.48 (m, 2H), 2.26 (t, 2H), 1.79 (m, 4H), 1.55 (m, 2H), 1.13-1.11 (broad m, 16H), 0.79 (t, 3H); $^{13}$C NMR (CDCl$_3$) δ 177.4, 134.8, 134.5, 122.5, 122.2, 118.0, 60.9, 34.7, 34.3, 33.4, 31.3, 28.9, 28.7, 28.6, 28.5, 27.0, 25.7, 24.6, 22.3, 13.8; MS (EI) m/z 348 (7%), 166 (17.8%), 165 (M+, 100.0%), 95 (9%), 81 (13%).

(f) 3-Hydroxypropyltriphenylphosphonium bromide

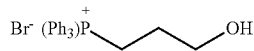

Triphenylphosphine (5.66 g, 0.022 mmol) and 3-bromopropanol (0.53 mL, 0.022 mmol) were dissolved in 50 mL of 95% ethanol. The flask was flushed with nitrogen and allowed to reflux at 100° C. for 90 minutes. Ethanol was decanted, 50 mL of toluene was added and the mixture was allowed to reflux for a further 90 minutes at 110° C. Toluene was decanted and the mixture was filtered using toluene as a rinsing solvent. The compound was collected under reduced pressure to yield a crude white powder (5.98 g, 0.0186 mmol, 86%).

$R_f$=0.57 (acetonitrile:water 9:1, iodine, KMnO$_4$). $^1$H NMR (300 MHz, CDCl$_3$) δ 7.70 (s, multiplet, 15H), 4.39 (m, singlet, 1H), 3.71 (m, multiplet, 4H), 1.81 (m, singlet, 2H); $^{13}$C NMR (CDCl$_3$) δ 135.0, 134.9, 133.4, 133.3, 130.5, 130.4, 118.8, 117.6, 60.3, 60.1, 25.8, 25.7, 20.4, 19.7; (EI) m/z 321 (M+100%) 291 (10.5%), 183 (6.9%), 108 (2.8%).

(g) (3-(12-Imidazol-1-yl)-octadecanoyl)propyl)triphenylphosphonium bromide (TPP-ISA)

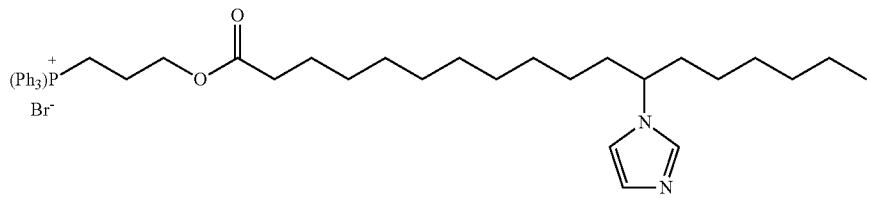

3-Hydroxypropyltriphenylphosphonium bromide (192.2 mg, 0.540 mmol), N,N'-dicyclohexylcarbodiimide 231.2 mg (1.12 mmol) and 12-imidazole stearic acid (12-(1H-imidazol-1-yl)octadecanoic acid) (171.7 mg, 0.489 mmol) were dissolved in 25 mL dichloromethane. The mixture was allowed to stir at room temperature overnight. The mixture was filtered using Celite to remove precipitated urea, and evaporated to give a crude product that was purified via column chromatography on silica (dichloromethane:methanol, 10:1) to yield 253.6 mg (0.368 mmol, 75.3%) of a slightly yellow, thick oil.

$R_f$=0.34 (dichloromethane:methanol 10:1). $^1$H NMR (300 MHz, CDCl$_3$) δ 7.9-7.6 (m, 15H), 7.45 (s, 1H), 7.04 (s, 1H), 6.87 (s, 1H), 4.35 (t, 2H), 4.01 (m, 2H), 3.86 (m, 1H), 2.21 (t, 2H), 1.99 (m, 2H), 1.69 (m, 4H), 1.50 (t, 2H), 1.25-1.05 (m, 22H), 0.82 (t, 3H); $^{13}$C NMR (CDCl$_3$) δ 173.1, 134.9, 134.9, 133.4, 133.3, 130.4, 130.2, 118.2, 117.0, 116.2, 62.9, 62.6, 58.4, 36.0, 33.8, 31.2, 29.0, 28.8, 28.7, 28.5, 25.7, 25.6, 24.5, 22.2, 21.9, 19.8, 19.1, 13.7; MS (FAB) m/z 653 (M+, 100%), 375 (9%), 319 (12%), 275 (12%), 262 (14%), 183 (12%), 69 (55%).

(h) 9-(Z)-(3-(12-imidazol-1-yl)octadeca-9-enoyloxy) propyl)triphenylphosphonium bromide (TPP-IOA)

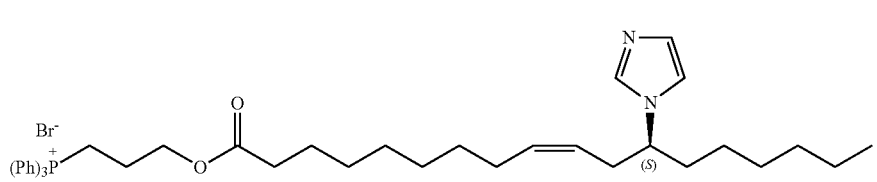

3-Hydroxypropyltriphenylphosphonium bromide (876.5 mg, 2.46 mmol), N,N'-dicyclohexylcarbodiimide (485.6 mg, 2.35 mmol) and 12-imidazol-1-yl-(Z)-9-octadecaenoate (816.7 mg, 2.34 mmol) were dissolved in 50 mL dichloromethane. The mixture was allowed to stir at room temperature overnight. The mixture was filtered using Celite to remove precipitated urea and evaporated to provide a crude product that was purified via column chromatography (dichloromethane:methanol 10:1) to yield 1.54 g (2.23 mmol, 95.3%) of a light yellow, thick oil.

$R_f$=0.58 (dichloromethane:methanol 10:1). $^1$H NMR (300 MHz, CDCl$_3$) δ 7.90-7.65 (m, 15H), 7.54 (s, 1H), 7.03 (s, 1H), 6.93 (s, 1H), 5.37 (m, 1H), 5.14 (m, 1H), 4.34 (t, 2H), 3.98 (m, 3H), 2.43 (m, 2H), 2.22 (t, 2H), 1.98 (m, 2H), 1.85-1.72 (m, 4H), 1.51 (m, 2H), 1.25-1.15 (m, 18H), 0.81 (t, 3H); $^{13}$C NMR (CDCl$_3$) δ 172.9, 134.82, 134.78, 133.2, 133.1, 133.0, 130.2, 130.0, 128.1, 123.4, 117.9, 116.8, 116.4, 62.7, 62.5, 58.4, 49.4, 34.9, 33.7, 33.6, 31.1, 28.8, 28.6, 28.5, 28.3, 26.7, 25.5, 24.3, 22.0, 21.8, 19.6, 18.9, 13.5; MS (FAB) m/z 651 (M+, 100%), 375 (11%), 319 (15%), 303 (12%), 289 (11%).

Example 2

Suppression of Peroxidase Activity of Cyt c Complexes

Materials and Methods

Peroxidase activity of cyt c was assessed by oxidation of Amplex Red, etoposide or TLCL as described above.

Results and Discussion (a) ISA, IOA, IEOA and IDA

Figure 2:
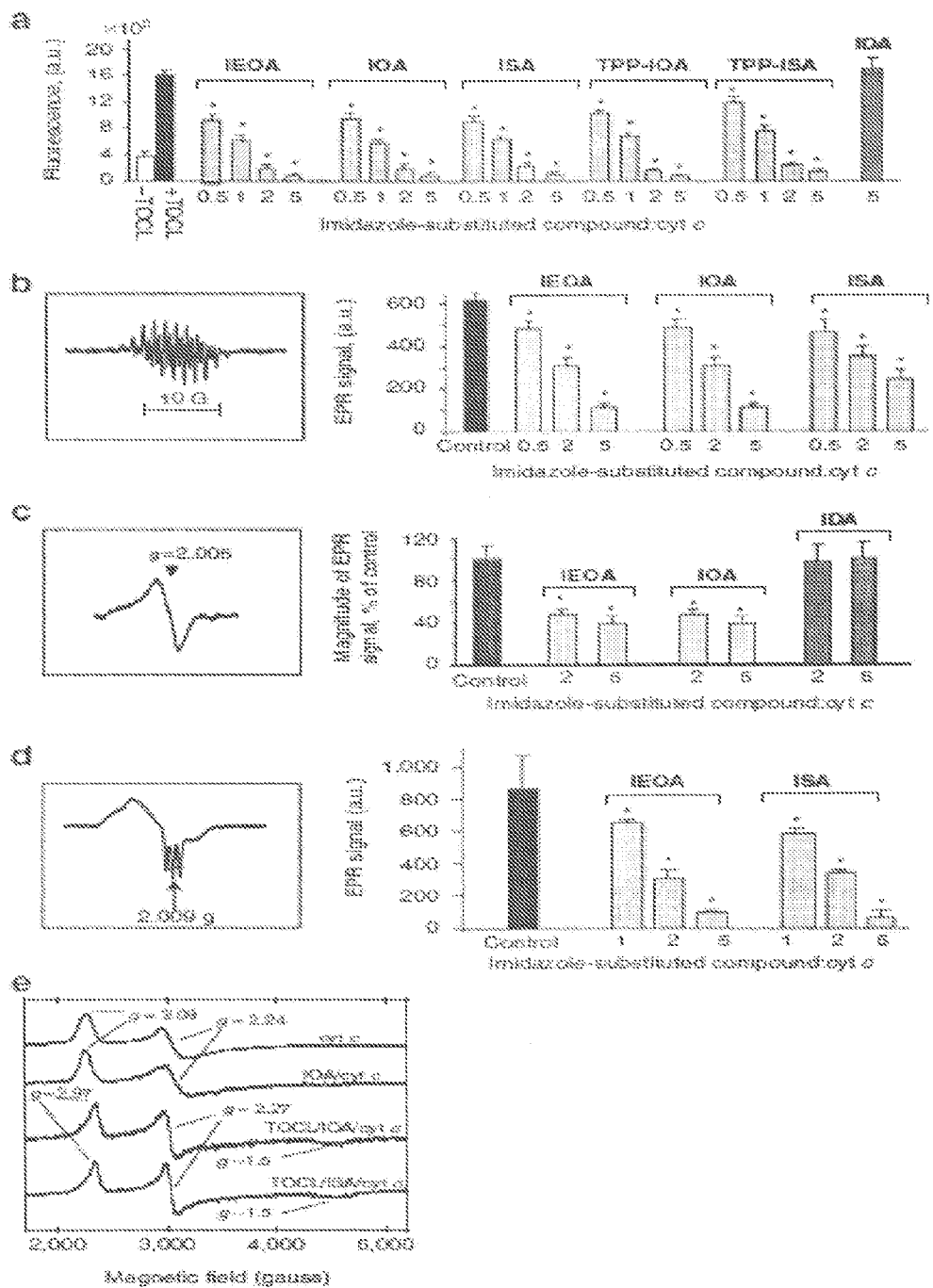
FIG. 2 shows the inhibition of peroxidase activity of cyt c/TOOL complexes.

The effect of ISA, IOA and IEOA (see FIG. 1 for structures) on the peroxidase activity of cyt c complexes with tetra-oleoyl-cardiolipin (TOOL) towards $H_2O_2$-driven oxidation of two prototypical phenolic substrates, Amplex Red (FIG. 2A) and etoposide (FIG. 2B) was evaluated. It was found that ISA, IOA and IEOA acted as potent inhibitors of the peroxidase activity of cyt c/TOOL complexes with both substrates (FIG. 2).

The truncated derivative IDA (see FIG. 1 for structure), did not exert any inhibitory effect (FIG. 2A).

Because catalytic reactive intermediates of cyt c/CL peroxidase complexes—protein-immobilized (tyrosyl) radicals (Tyr•)—can be detected by electron paramagnetic resonance (EPR) spectroscopy[32], the effect of IEOA and IOA on $H_2O_2$-dependent formation of radicals (FIG. 2C) was studied. Both IOA and IEOA (but not IDA) effectively quenched generation of Tyr. radicals.

Figure 3:
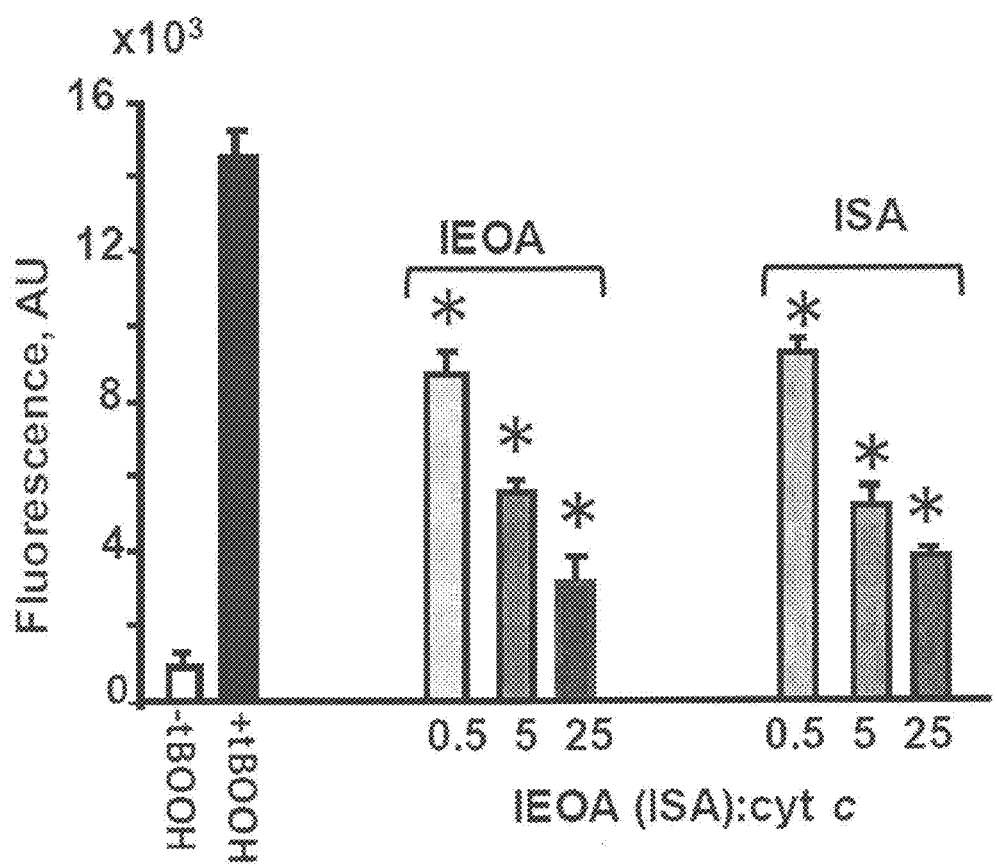
FIG. 3 shows assessments of the effect of IEOA and ISA on peroxidase activity of mouse liver mitochondria by oxidation of Amplex Red to resorufin. Data are means±S.D., n=3, *p<0.01 vs. control (no ISA, IEOA added).

Finally, the ability of ISA and IEOA to inhibit peroxidase activity using isolated mouse liver mitochondria was assessed. To avoid decomposition of $H_2O_2$ by catalase, tert-butyl hydroperoxide (tBOOH) was used as a source of oxidizing equivalents. Both ISA and IEOA suppressed peroxidase activity in a concentration-dependent manner (FIG. 3).

(b) TPP-ISA and TPP-IOA

TPP-ISA and TPP-IOA were as effective as non-conjugated ISA and IOA in inhibiting peroxidase activity of cyt c/TOOL complexes (FIG. 2).

Example 3

Liganding of haem-iron in cyt c/TOCL Complexes (a) Low-Temperature EPR Measurements of Protein-Immobilized Radicals To address whether ISA and IEOA act as strong ligands of haem-iron in cyt c/TOOL complexes, low-temperature EPR spectroscopy was used[33]. In the reduced form, cyt c/TOOL binds N. to produce haem-nitrosylated complexes with characteristic EPR spectra[9].

Materials and Methods

EPR spectra of protein-immobilized (tyrosyl) radicals were recorded after the addition of $H_2O_2$ (500 µM) to cyt c (100 µM) incubated with tetra-oleoyl-cardiolipin (TOOL) liposomes at room temperature. After incubation for 20 s, the reaction was stopped by freezing the samples in liquid nitrogen. EPR spectra were obtained on a JEOL-REIX spectrometer with 100 kHz modulation (JEOL, Kyoto, Japan). EPR spectra from frozen samples were recorded at 77 K under the following conditions: center field, 3230 G; sweep width, 100 G; field modulation, 5 G; microwave power, 1 mW; receiver gain, $10^3$; time constant, 0.1 s; time scan, 4 min.

Heme nitrosylation: Cyt c (100 µM) was incubated with a nitroxyl donor, Angeli's salt (500 µM), for 30 min at room temperature. The reaction was stopped by freezing the samples in liquid nitrogen. The EPR spectra of heme-nitrosylated cyt c were measured at 77 K under the following instrumental settings: center field, 3200 G; scan range, 500 G; field modulation, 5 G; microwave power, 10 mW; time constant, 0.1 s; scan time, 4 min; receiver gain, $10^3$.

Results and Discussion

At 77 K, typical spectra of penta-, and hexa-coordinated cyt c were detectable on incubation of cyt c/TOOL complexes in the presence of a source of nitroxyl (HNO), Angeli's salt (FIG. 2D). ISA and IEOA (FIG. 2D) caused a concentration-dependent decrease of the EPR signal.

(b) Liquid-He EPR Measurements of ISA and IEOA Liganding

To provide evidence for coordination changes of the haem-iron in cyt c, liquid-He EPR measurements were performed.

Materials and Methods

Conditions: native cyt c (300 µM), IEOA/cyt c (2:1), TOCL/IEOA/cyt c (20:2:1), 20 mM HEPES buffer, pH 7.4. Samples (200 µl) were placed in 3 mm o.d. suprasil quartz EPR tubes and frozen in liquid nitrogen for subsequent spectroscopic measurements. X-band (9 GHz) EPR spectra were recorded on a Bruker ESP 300 spectrometer equipped with an Oxford Instruments ESR 910 flow cryostat for ultra-low-temperature measurements. Spectra were recorded at 9.8 G modulation amplitude and 200 µW microwave power. The microwave frequency was calibrated by a frequency counter and the magnetic field was calibrated with a gaussmeter. The temperature was calibrated with carbon-glass resistors (CGR-1-1000) from LakeShore. This instrument and the software (SpinCount) to analyse the EPR spectra were provided by Professor Mike Hendrich, Carnegie Mellon University.

Results and Discussion

The X-band EPR spectrum of native ferri-cyt c at pH 7.4, recorded at 20 K, exhibited anisotropic, low-spin signals, with $g_z=3.09$, $g_y=2.24$ and $g_x\sim1$ (usually unobserved) (FIG. 2E) indicative of His/Met axial coordination at the haem[34,35]. On the addition of IOA, there was no change in the EPR spectrum indicating retention of the native His/Met axial coordination (FIG. 2E). However, when IOA was added to the cyt c/TOCL complex, the EPR spectrum revealed the presence of another low-spin species ($g_z=2.97$, $g_y=2.27$, $g_x\sim1.5$, FIG. 2E) with g-values entirely consistent with His/imidazole coordination[35,36]. This signal was broadened on the low-field side, suggesting a combination of the native ferri-cyt c and a His/imidazole form. Spectral simulations confirm an ~50:50 mixture of the native structure and the form in which $Met_{80}$ has been replaced by the imidazole moiety of IOA. These were the only signals observed; in particular, there were none at g~6, indicating the absence of any penta- or hexacoordinate high-spin species. Similarly, ISA was able to change haem-iron coordination in cyt c, whereby $Met_{80}$ was substituted by the imidazole moiety (FIG. 2E). These results confirm experimentally that the imidazole moiety of imidazole fatty acids can indeed serve as a coordinating ligand for the haem substituting for $Met_{80}$ ligation.

The present studies demonstrate that imidazole fatty acids specifically interact with partially unfolded cyt c and not with intact cyt c. While it is possible that imidazole fatty acids may interact with other hemoproteins—for example, cytochromes P450[Error! Bookmark not defined.], their effects on the oxygenase/peroxidase activity of the hemoproteins might depend on several parameters such as redox potential, heme-coordination state, spin states. The results of the low-temperature (He) EPR experiments indicate that liganding of heme-iron in cyt c by IOA was specifically dependent on the presence of CL. Notably, many hemoproteins with peroxidase function—cytochromes P450, myeloperoxidase, cyclooxygenase—do not require anionic (phospho)lipids for their activation.

Example 4

Inhibition of Apoptosis by TPP-ISA and TPP-IOA

Materials and Methods

Assessment of TPP-IOA in Mouse Embryonic Cells and Subcellular Fractions.

Mouse embryonic cells ($2\times10^6$) were seeded in 100 mm cell culture dishes and let attached overnight. Thereafter, the cells were incubated with TPP-IOA (10 µM) in PBS at 37° C. for 30 min, washed with PBS (2×5 mL), and collected by trypsinization. Mitochondria were isolated as described above. In mitochondria, TPP-IOA was analyzed by HPLC after precipitation of proteins with $CH_3CN$ (final concentration, 70%; incubation time, 15 min at 4° C.; centrifugation, 5 min at 10,000×g). TPP-IOA from cytosolic fractions was extracted by following the protocol of Folch et al.[37] and then re-dissolved in a minimal volume of methanol. Isocratic HPLC separation of TPP-IOA was achieved with 90% methanol containing 20 mM $LiClO_4$ at flow rate of 1 ml/min using Zorbax Eclipse XDB-C18 column (5 µm; 4.6×150 mm; Agilent, Santa Clara, Calif., USA). Detection of TPP-IOA was performed with a SPD-M10A photodiode array detector (Shimadzu, Kyoto, Japan) following the specific UV spectrum of the triphenylphosphonium function ($\lambda_{max}$=224, 264 and 274 nm; FIG. 4A, Inset). TPP-IOA was eluted as single peak with retention time of 4 min.

ATP Measurements.

ATP levels in cells were measured using ATP bioluminescent somatic cell assay kit (St. Louis, Mo.) according to the manufacturer's instructions.

Production of Superoxide Anion Radicals.

A superoxide-meditated oxidation-sensitive fluorogenic dye, dihydroethidium (DHE), was utilized for assessments of superoxide production. Briefly, cells were incubated with 5 µM of DHE for 30 min. Cells were collected by trypsinization and re-suspended in PBS. The fluorescence of 2-hydroxy-ethidium was measured using a FACScan flow cytometer (BD Biosciences, San Jose, Calif.) supplied with the CellQuest software. Mean fluorescence intensity from 10,000 cells was acquired using a 585/42-nm band-pass filter.

Exposure of Mouse Embryonic Cells to γ-Irradiation.

Mouse embryonic cells were seeded on a 35 mm dish at a cell density of $5\times10^4$/dish, and allowed to attach overnight. The cells were γ-irradiated at a dose of 10 Gy using a Shepherd model 143-45A irradiator (J.L. Shepherd & Associates, CA). Ten min after irradiation, different concentrations of TPP-ISA or TPP-IOA (2.5 and 5 µM) were added and cells were incubated at 37° C. in 5% $CO_2$ for 48 h. Then, cells were harvested for measuring phosphatidylserine externalization by an Annexin V/PI kit and caspase 3/7 activity using a Caspase-Glo® 3/7 Assay kit. Data are means±S.D., n=3. *p<0.01 vs. irradiated only cells.

Phosphatidylserine Externalization.

Phosphatidylserine externalization was determined by an Annexin V-FITC apoptosis detection kit (Biovision) according to the manufacturer's instructions.

Caspase 3/7 Activity.

Caspase-3/7 activity was measured using a luminescence Caspase-Glo 3/7 assay kit (Promega) according to the manufacturer's instructions.

Measurement of Cyt c Release by Western Blot Analysis.

Cells were collected after 48 h post-irradiation incubation and resuspended in lysis buffer containing 0.05% digitonin for 4 min on ice. Supernatants were collected after centrifugation for 10 min at 10,000 g. Equal amounts of protein were subject to 15% SDS-PAGE, transferred onto a nitrocellulose membrane, and probed with antibodies against cyt c (clone 7H, 8.2; C12, BD Pharmingen) or actin (Novus) (loading control) followed by horseradish peroxidase-coupled detection. The protein band profile was analysed by densitometry using Labworks image acquisition and analysis software (UVP).

Cell-Free Apoptosis System (S100 System).

The cytosol extracts (S100) of mouse embryonic cells were obtained as described previously[38] with minor modifications. Briefly, the cells were washed twice in cold phosphate-buffered saline, pH 7.4, and the resulting pellet was resuspended in buffer containing 25 mM HEPES-KOH, pH 7.0, 10 mM KCl, 1.5 mM $MgCl_2$, 1 mM EDTA, 1 mM EGTA, 1 mM DTT, 0.1 mM phenylmethylsulfonyl fluoride, 0.05% digitonin, and 1% protease inhibitor mixture for 2 min at 4° C. Cells were centrifuged at 4° C. for 10 min at 10,000×g. The resulting supernatant was further centrifuged at 4° C. for 50 min at 100,000×g. The supernatant was collected as S-100 and kept at −80° C. until further use. For caspase-3 activation, S100 (5 µg of protein/µl) was incubated with 1 mM dATP and 1 µM cyt c for 90 min at 37° C. The caspase-3 activity was evaluated using Enzchek caspase-3 assay kit as described in the manufacturer's manual (Invitrogen, Carlsbad, Calif.).

Exposure of Mouse Lung Endothelial Cells to Rotenone.

Mouse lung endothelial cells were maintained in 2% $O_2$, 5% $CO_2$, 93% nitrogen in Opti-MEM containing 10% FBS, 2 mM glutamine, 0.2% retinal derived growth factor, 10 U/mL heparin, 0.1 mM non-essential amino acid supplement and 55 µM β-mercaptoethanol. Cells at passage 4 to passage 6 were seeded on collagen/gelatin coated plates and incubated with 2 µM rotenone in growth factor depleted medium together with TPP-IOA (2.5, 5 µM) for 48 h, then cells were collected by trypsinization.

Clonogenic Assay.

Cells were plated in 35-mm dishes with 2 ml culture medium at the appropriate density (between 100 and 1000 cells per dish). TPP-ISA (2.5 µM) or TPP-IOA (2.5 µM) was added to the cell culture 30 min post γ-irradiation. Medium containing TPP-ISA or TPP-IOA was replaced with fresh complete culture medium after 4 hrs. Colonies were fixed and stained with 0.25% crystal violet and 10% formalin (35% v/v) in 80% methanol for 30 min after a 7-day incubation, and those with >50 cells were scored as survivors. The surviving fraction was calculated as the plating efficiency (=number of colonies counted/number of cells seeded×100%) of samples relative to that of control. The data were fitted to a single-hit multi-target model. $D_0$—the dose needed to reduce cell surviving fraction to 37% (1/e)—was estimated from the curves fitted to evaluate the radiomitigative effects of TPP-ISA and TPP-IOA.

Results and Discussion

The ability of imidazole substituted fatty acids to inhibit apoptosis in cells was explored. To target imidazole substituted fatty acids into mitochondria, the fatty acids were esterified with 3-hydroxypropyl-triphenylphosphonium (TPP) salt (FIG. 1); an organic cationic alcohol with delocalized electron density[39]. As mentioned above, TPP-ISA and TPP-IOA were found to be as effective as non-conjugated ISA and IOA in inhibiting peroxidase activity of cyt c/TOOL complexes (FIG. 2).

Figure 4:
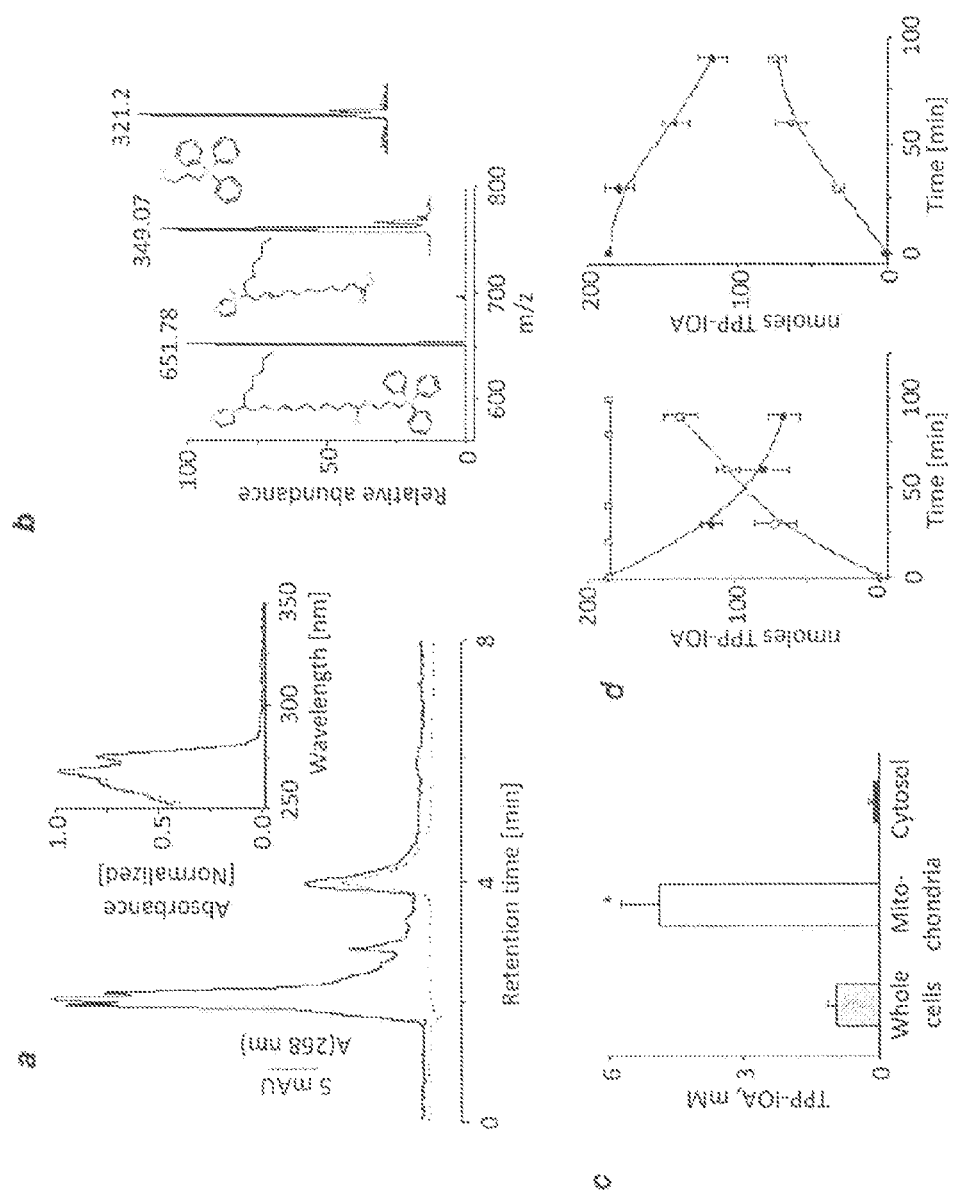
FIG. 4 shows HPLC and ESI-MS analysis of hydrolysis of TPP-IOA and its hydrolysis products in mitochondria and cytosol of mouse embryonic cells.

The amounts of accumulated TPP-IOA in mitochondria of mouse embryonic cells were estimated using high-performance liquid chromatography (HPLC) and electrospray ionization mass spectrometry (ESI-MS) (FIG. 4). It was found that most of the TPP-IOA was present in mitochondria (FIG. 4). Assuming that the volume of mitochondria constitutes ~15-25% of the total volume of a cell, the mitochondrial enrichment factor becomes even greater such that the concentration of TPP-IOA in mitochondria may be as high as ~5 mM.

It was not demonstrated prior to the present studies whether endogenous esterases can hydrolyse the ester-bond and release IOA and TPP-derived propanol. To test this, assessments of esterase activity of mitochondria and cytosolic fractions isolated from mouse embryonic cells were performed based on HPLC measurements of TPP-IOA (FIG. 4). It was found that hydrolysis of TPP-IOA takes place in both mitochondria and the cytosol. The hydrolysis rate in mitochondria was comparable to that in the cytosolic fraction (FIG. 4). Thus, both TPP-IOA and its de-esterifed form, IOA, could be present in mitochondria of mouse embryonic cells.

Because TPP-conjugated imidazole-substituted fatty acids effectively partition into mitochondria, it was examined whether they affected bioenergetic functions, particularly ATP production. Neither TPP-IOA nor TPP-ISA had any effect on ATP levels in mouse embryonic cells.

Figure 5:
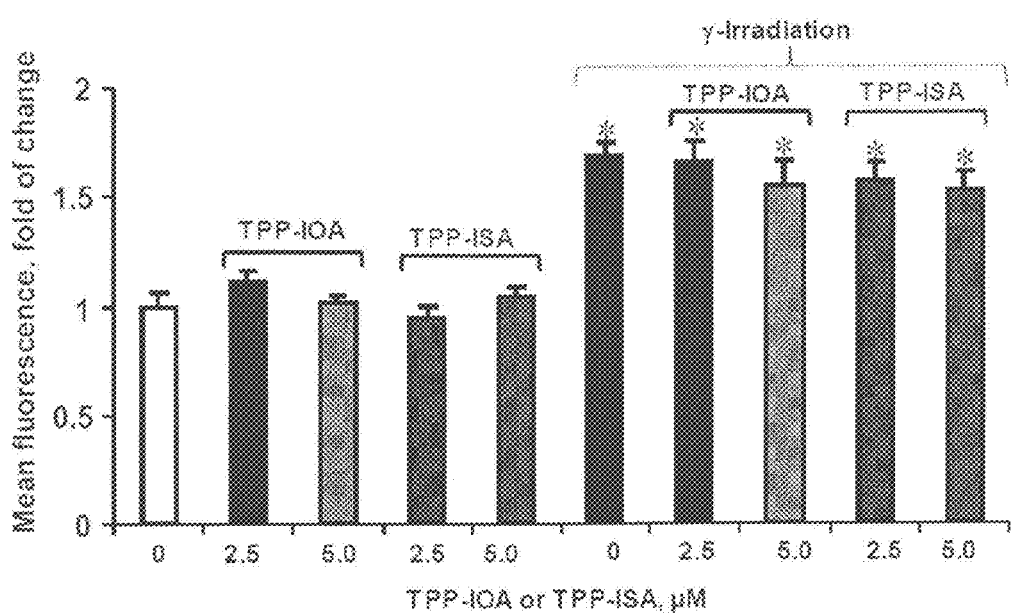
FIG. 5 shows assessments of superoxide generation in mouse embryonic cells after treatment with TPP-IOA and TPP-ISA. Cells were γ-irradiated at a dose of 10 Gy and then incubated with different concentrations of TPP-IOA or TPP-ISA (2.5 and 5 µM) for 18 hrs. To estimate superoxide generation, cells were incubated with 5 µM of dihydroethidium (DHE) for 30 min at 37° C. Collected cells were re-suspended in phosphate buffered saline (PBS) and fluorescence of 2-hydroxyethidium was analyzed using FACScan supplied with CellQuest software. Data are means±S.D., n=3. *p<0.01 vs. control cells (without any treatment).

Normally, mitochondria are the major source of superoxide radicals in mouse embryonic cells[40,41]. Assessments of intracellular superoxide production using dihydroethidium showed that neither TPP-IOA nor TPP-ISA had any effect on superoxide production in cells with or without radiation treatment (FIG. 5).

Figure 6:
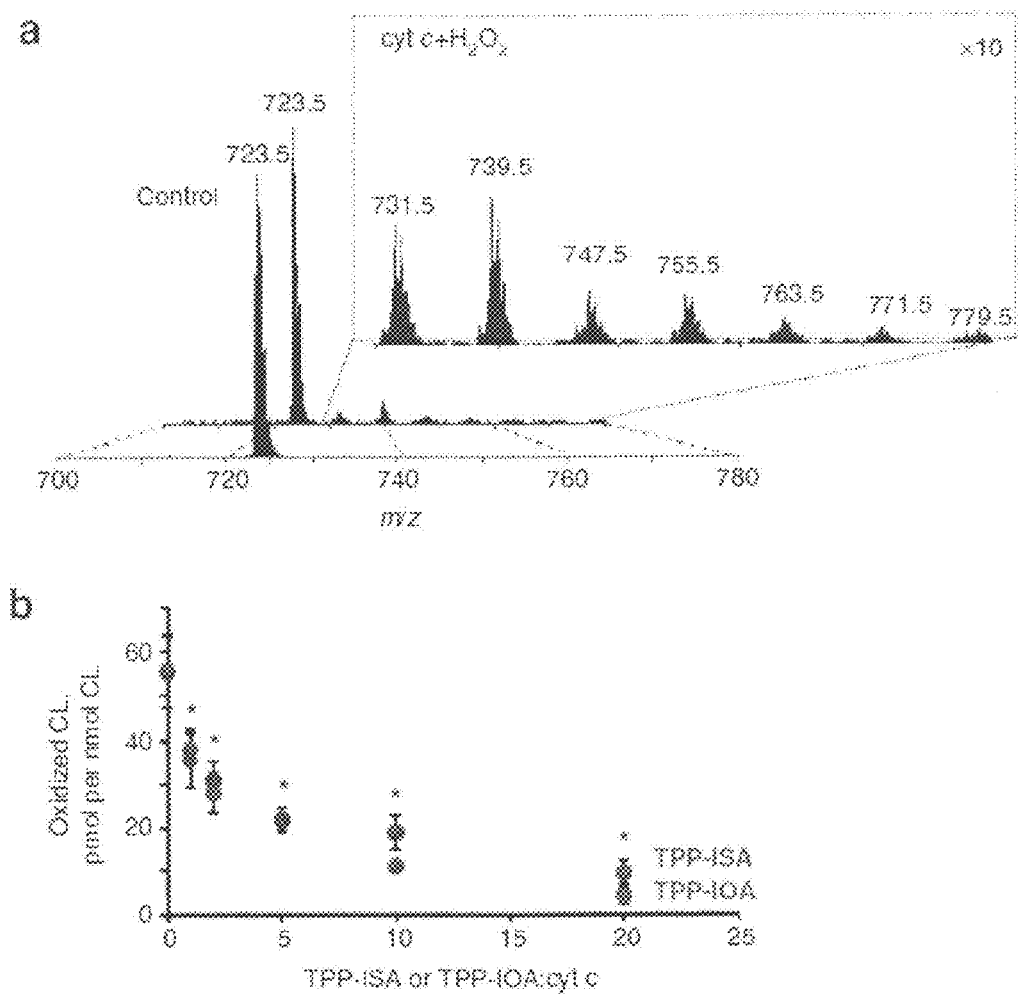
FIG. 6 shows inhibition of $H_2O_2$-induced TLCL (tetralinoleoyl-cardiolipin) peroxidation.

For the anti-apoptotic action, the proposed haem-iron ligation inhibits peroxidation of polyunsaturated species of CL. Therefore, an oxidizable tetra-linoleoyl-cardiolipin (TLCL) was used, and experiments conducted on its cyt c/$H_2O_2$-induced oxidation (FIG. 6). In the presence of $H_2O_2$, accumulation of characteristic TLCL peroxidation products with multiple oxygenated linoleic acid residues detectable by ESI-MS were detected (FIG. 6A). It was found that both TPP-IOA and TPP-ISA inhibited cyt c/$H_2O_2$-induced oxidation of TLCL in a concentration-dependent manner. No difference in inhibition of TLCL oxidation between TPP-IOA and TPP-ISA was detected. The oxidation of TLCL was completely blocked at a ratio of cyt c to TPP-IOA or TPP-ISA of 1:20 (FIG. 6B).

A model of intrinsic apoptosis induced in mouse embryonic cells by γ-irradiation was employed, and several biomarkers of apoptosis assessed. It was found that TPP-IOA and TPP-ISA had similar radiation mitigating effects on mouse embryonic cells as evidenced by phosphatidylserine (PS) externalization (FIG. 7A), caspase 3/7 activation (FIG. 7B) and cyt c release (FIG. 7C). In contrast, IEOA or ISA—devoid of a mitochondria-targeting TPP-moiety—exerted no protection against apoptosis in mouse embryonic cells (FIG. 7D).

To verify that the protective effects were realized during mitochondrial stages of apoptosis, TPP-ISA were added to the in vitro 'caspase activation system' containing S100 fraction from mouse embryonic cells[38]. Caspase activation caused by exogenously added cyt c was completely insensitive to TPP-ISA and TPP-IOA (FIG. 7E) thus confirming that anti-apoptotic effects of TPP-IOA and TPP-ISA were realized in mitochondria. Furthermore, the anti-apoptotic activity was neither cell-nor stimulus-specific, as TPP-IOA effectively inhibited apoptosis, induced by a mitochondrial complex I inhibitor, rotenone, in cultured mouse lung endothelial cells (FIG. 7F).

Mitochondria are believed to be involved in orchestration of different cell death pathways[42,43]. It was found that necrotic cells (propidium iodide (PI)-positive, Annexin V-positive) represented 12.9% while apoptotic cells (PI-negative, Annexin V-positive) were accountable for 28.9% of total PS-positive cells detectable after irradiation. Treatment with TPP-IOA caused a twofold decrease in the number of apoptotic cells (to 14.8%) and 1.6-fold reduction in the number of necrotic cells (to 8.2%). Similarly, TPP-ISA protected via both anti-apoptotic and anti-necrotic mechanisms (to 13.9% of apoptotic and 7.8% necrotic cells, respectively). Overall, these results suggest that TPP-IOA and TPP-ISA afforded the radiomitigation in mouse embryonic cells acting through both anti-apoptotic and anti-necrotic pathways.

In addition to apoptosis and necrosis, mitotic cell death can be also triggered in irradiated cells. Using a clonogenic assay that includes the mitotic cell death component, it was demonstrated that post-irradiation treatment of mouse embryonic cells with TPP-ISA or TPP-IOA resulted in a significant protection. Using a single-hit multi-target model, it was estimated that TPP-ISA or TPP-IOA increased $D_0$—the dose needed to reduce cell surviving fraction to 37% (1/e)—to 1.67±0.06 and 1.71±0.05, respectively, compared with 1.33±0.08 in untreated cells (FIG. 7G).

Example 5

In Vivo Assessments of Radioprotective/Radiomitigative Effects of TPP-IOA and TPP-ISA using C57BL/6NTac Female Mice Given the ability of TPP-IOA and TPP-ISA to act as radiomitigators in vitro, their potential to act as radioprotectors/radiomitigators in vivo was assessed.

Materials and Methods

Animals.

C57BL/6NTac female mice were anaesthetized with Nembutal (1 mg per 20 g mouse), irradiated to a total body dose of 9.25 Gy using either a Shepherd Mark 1 Model 68 cesium irradiator at a dose rate of 80 cGy min$^{-1}$ (31-35 mice per group) or a Varian TrueBeam linear accelerator (Varian Medical Systems) at 100 monitor units or 100 cGy min$^{-1}$ using 6 MV photons with a 40 cm×40 cm field at 100 SSD (10-23 mice per group). Mice were injected intraperitoneally (i.p.) with 5 mg per kg body weight of TPP-IOA in a 100 µl volume of water containing 25% ethanol at 1 h before irradiation, 10 min before irradiation, 10 min after irradiation, 5 h after irradiation and 24 h after irradiation. Other groups were injected i.p. with 2.5 mg per kg body weight of TPP-IOA or 5 mg per kg body weight of TPP-ISA 10 min after irradiation. The mice were followed for the development of haematopoietic syndrome (at which time they were killed). The health of the non-irradiated mice was unexceptional and no adverse side effects were noticed over the period of study (52 days) after i.p. injection of either TPP-IOA or TPP-ISA (5 mg per kg body weight).

The log-rank test was used for three analyses: the comparison of overall survival that is defined as the time from the date of radiation to the date of death for all mice under study; the comparison of short-term survival over the first 20 days, that is, the overall survival count at 20 days; and the comparison of conditional survival in mice surviving 20 or more days, that is, the time from the date of radiation to the date of death for all mice who survived 20 days or longer after radiation. All these comparisons were made between each of the treated groups and the radiation-only control group. All procedures were pre-approved and performed according to the protocols established by the Institutional Animal Care and Use Committee of the University of Pittsburgh.

Selective Reaction Monitoring (SRM) and Multiple Reaction Monitoring (MRM) Analysis of TPP-IOA and its Hydrolysis Products.

TPP-IOA and its hydrolysis products were extracted from plasma, small intestine and bone marrow tissue 10 min after TPP-IOA i.p. injection into animals (5 mg/kg body weight), using a standard Folch procedure for extraction of lipids[37]. In one set of runs, intact TPP-IOA was assessed by SRM as described below. In an identical set of duplicate runs, hydrolyzed TPP-IOA (in the form of the TPP moiety, see below) was assessed by a different mass spectrometric method, MRM, as described below.

Selective Reaction Monitoring:

TPP-IOA (m/z 651) was assessed by SRM in a LCQ-Duo ion trap mass spectrometer (Thermo, Inc., Waltham, Mass.). Chromatography was performed on an Eclipse XDB reverse phase C18 column (4.6 mm×15 cm, Agilent Technologies, Santa Clara, Calif.) using an isocratic solvent system consisting of acetonitrile:water:triethylamine:acetic acid (450:50:2.5:2.5, v/v/v/v) and a flow rate of 0.4 ml/min. The transition measured was 651>303 (TPP-IOA to TPP-propyl moiety—water) within a 0.5 Da window. Instrument conditions were as follows: spray voltage, 4.5 kV, positive mode; sheath gas, 30; capillary temperature, 250° C.; tube lens, 20; capillary voltage, 26. The instrument was tuned for the appropriate parent ion and all parameters were optimized to maximize the transition during the SRM including tuning under appropriate flow conditions.

Multiple Reaction Monitoring:

MRM conditions for assessment of hydrolyzed TPP-IOA utilized the same LC conditions. Transitions measured during MRM were as follows: 321 to 303 and 303 to 262 (TPP-propyl to TPP-propyl minus water to TPP, respectively). Instrument conditions were as follows: spray voltage, 4.5 kV, positive mode; sheath gas 20; capillary temperature, 300° C.; tube lens, 20; capillary voltage, 26. The hydrolysis measured the appearance of the TPP-propyl/TPP group and not the appearance of the IOA. Based on studies using IOA standard it was concluded that measurements at the pg level could not be attained due to IOA's poor ionization efficiency. This was most likely due to the zwitterionic nature of the IOA, allowing a positive charge to be associated with the imidazole group and a negative charge to be associated with the carboxyl group. This prevented strong ionization in either the positive or negative mode at low abundances despite modifiers that were added to the mobile phase system. Additions of various mobile phase modifiers to the solvent system were not able to enhance ionization of the IOA in either positive or negative mode. To circumvent this problem, an LC-MS/MS method was also developed to assess the alternative product of the hydrolysis, namely the TPP-propyl group. Like the parent molecule (TPP-IOA), the strong positive charge allowed excellent ionization efficiencies and measurement at the pg level.

Results and Discussion

Figure 8:
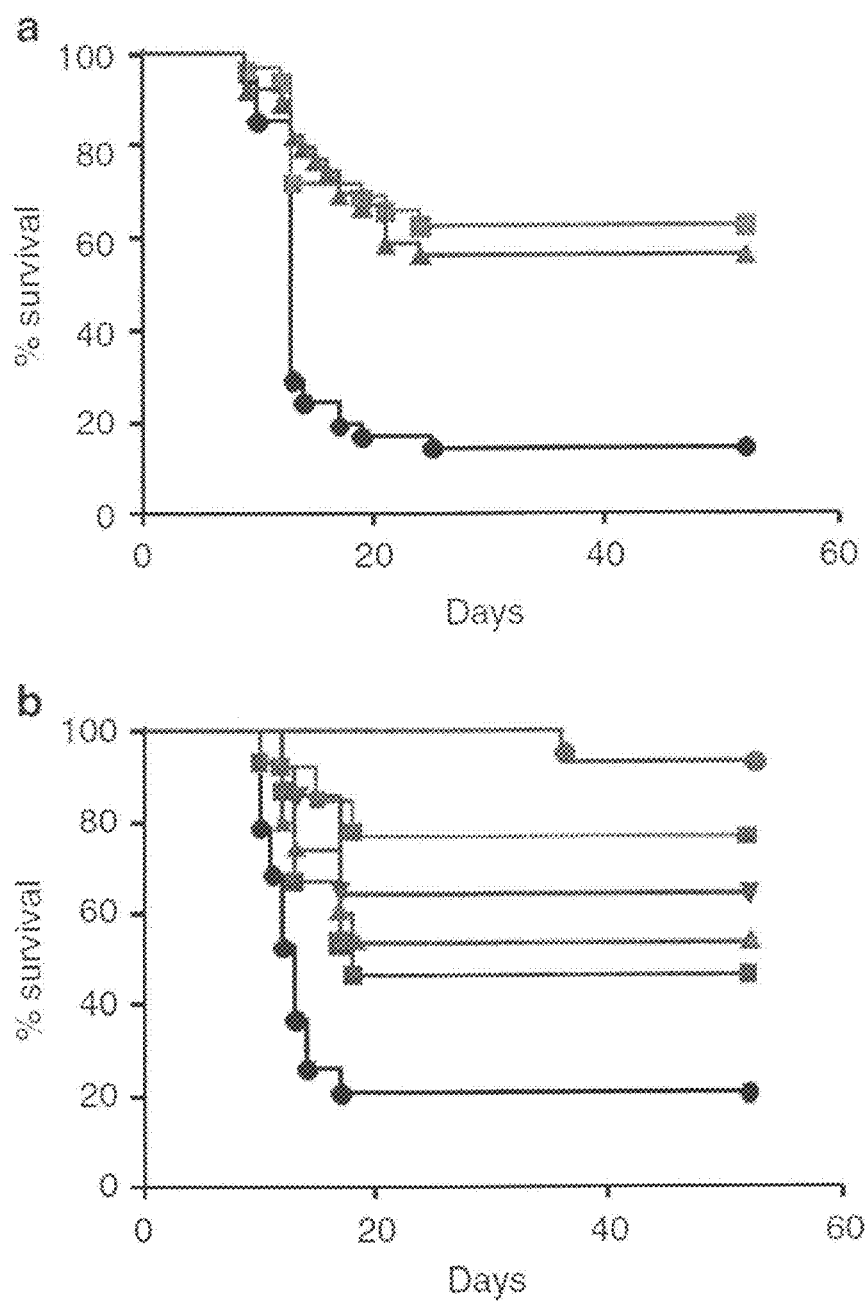
FIG. 8A shows radiation protection and mitigation by TPP-IOA and TPP-ISA. C57BL/6NTac female mice were exposed to total body irradiation to a dose of 9.25 Gy using a cesium source (n=31-35 mice per group). The mice were irradiated and injected i.p. with TPP-IOA or TPP-ISA (5 mg per kg body weight in 100 µl of water containing 25% ethanol) 10 min after irradiation. Mice exposed to: total body irradiation at the dose of 9.25 Gy only (circles); to total body irradiation at the dose of 9.25 Gy and injected with TPP-ISA (5 mg per kg body weight) 10 min (triangles) or TPP-IOA (5 mg per kg body weight) 10 min (squares) thereafter. P<0.0001 (a two-sided log-rank test)—TPP-IOA or TPP-ISA injected and exposed to total body irradiation mice versus mice exposed to total body irradiation only. For assessments of significance see Table 1.
FIG. 8B shows radiation protection and mitigation by TPP-IOA and TPP-ISA. C57BL/6NTac female mice were exposed to total body irradiation to a dose of 9.25 Gy using a linear accelerator (n=10-23 mice per group). The mice were injected i.p. with TPP-IOA (5 mg per kg body weight in 100 µl of water containing 25% ethanol) at 1 h or 10 min before irradiation or 10 min, 5 or 24 h after irradiation. Mice exposed to: total body irradiation at the dose of 9.25 Gy only (black circles); to total body irradiation at the dose of 9.25 Gy and injected with TPP-IOA (5 mg per kg body weight) 10 min (grey circles), 5 h (downward-pointing triangles) and 24 h (lower grey squares) thereafter. Mice injected with TPP-IOA (5 mg per kg body weight) 10 min (upper grey squares) and 1 h (upward-pointing triangles) before total body irradiation (9.25 Gy). For assessments of significance see Table 1.

C57BL/6NTac female mice were exposed to 9.25 Gy total body irradiation at the dose rate of 80 cGy min$^{-1}$ using the cesium irradiator. Three independent experiments (the total number of mice in each group was 31-35) yielded similar results: irradiation resulted in death of animals within 13-15 days (with survival of only 20% of animals by day 30). TPP-IOA or TPP-ISA (i.p. injection, 5 mg per kg body weight, 10 min after irradiation) showed a strong radiomitigative effect for both compounds (FIG. 8A). There was no statistically significant difference in radiomitigative potency of TPP-IOA and TPP-ISA (P=0.6389, a two-sided log-rank test).

A clinical linear accelerator was also used to deliver the radiation dose. The mice (three groups with 22-23 animals in each) were irradiated to 9.25 Gy at the dose rate of 100 cGy min$^{-1}$ using a Varian TrueBeam linear accelerator (Varian Medical Systems) and injected i.p. with 5 mg per kg body weight of either TPP-ISA or TPP-IOA, 10 min after irradiation. Similar to the results with the cesium irradiator, the survival curves over 52 days were statistically different for TPP-IOA (5 mg per kg body weight) and TPP-ISA (5 mg per kg body weight) versus irradiated controls (Table 1). However, there was no statistically significant difference between TPP-IOA and TPP-ISA (P=0.4567, a two-sided log-rank test).

Thus, after multiple experiments, using two different irradiators, a high potency of both TPP-IOA and TPP-ISA in mitigating radiation damage without a significant difference in radiomitigative activity between them was demonstrated. Therefore, all subsequent in vivo experiments were conducted with TPP-IOA and linear accelerator as the radiation source.

A dose of 5 mg per kg body weight of TPP-IOA was chosen because a lower dose (2.5 mg per kg body weight) of drug was not effective in mitigating the mice against irradiation. When mice (10 per group) were irradiated and administered 2.5 mg per kg body weight (10 min after irradiation), there was a trend towards a greater survival that, however, did not reach the level of significance (P=0.0525, a two-sided log-rank test) (Table 1).

It was further tested whether TPP-IOA was protective if given at later time points (than 10 min) after irradiation (10 mice per group). Administration of TPP-IOA at 5 or 24 h after irradiation resulted in a significant increase in survival (FIG. 8B, Table 1). TPP-IOA was also protective if given 10 min or 1 h before irradiation (FIG. 8B; Table 1).

Figure 9:
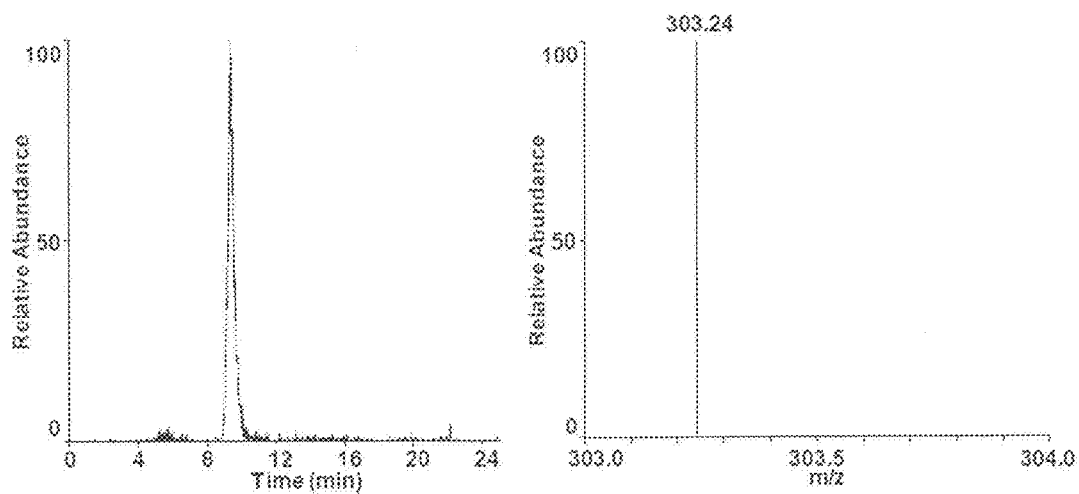
FIG. 9 shows selective reaction monitoring (SRM) analysis of TPP-IOA. TPP-IOA was quantitated by SRM analysis. A plasma sample (10 min after i.p. injection of TPP-IOA, 5 mg/kg body weight) containing TPP-IOA was chromatographed on a C18 column and exhibited a retention time of 9.4 min (left panel). The transition m/z 651→303 was measured (right panel) corresponding to TPP-IOA to TPP-propyl minus water.

Given the high radioprotective/radiomitigative activity of TPP-IOA, the extent to which it would be absorbed to reach radiosensitive tissues was determined. This required the development of new LC-MS/MS protocols to quantitate TPP-IOA in tissue samples. These involved the establishment of a selective reaction monitoring protocol for TPP-IOA that provides high selectivity and sensitivity. The direct assessments clearly demonstrated the presence of TPP-IOA in plasma (FIG. 9) as well as in the two most important radiosensitive tissues; bone marrow and small intestine. TPP-IOA levels were highest in plasma (54.0 ng ml$^{-1}$ of plasma), followed by small intestine (1.5 ng per g of tissue) and bone marrow (0.2 ng per g of tissue), at the 10 min time point after i.p. injection. The levels measured in plasma are consistent with those found for decyl-TPP; a related compound, as seen in the study by Porteous et al.$^{44}$ The present study showed that, after intravenous injection, the TPP-compounds are distributed rapidly to various tissues and less than 1% remains in plasma after 15 min.

Figure 7:
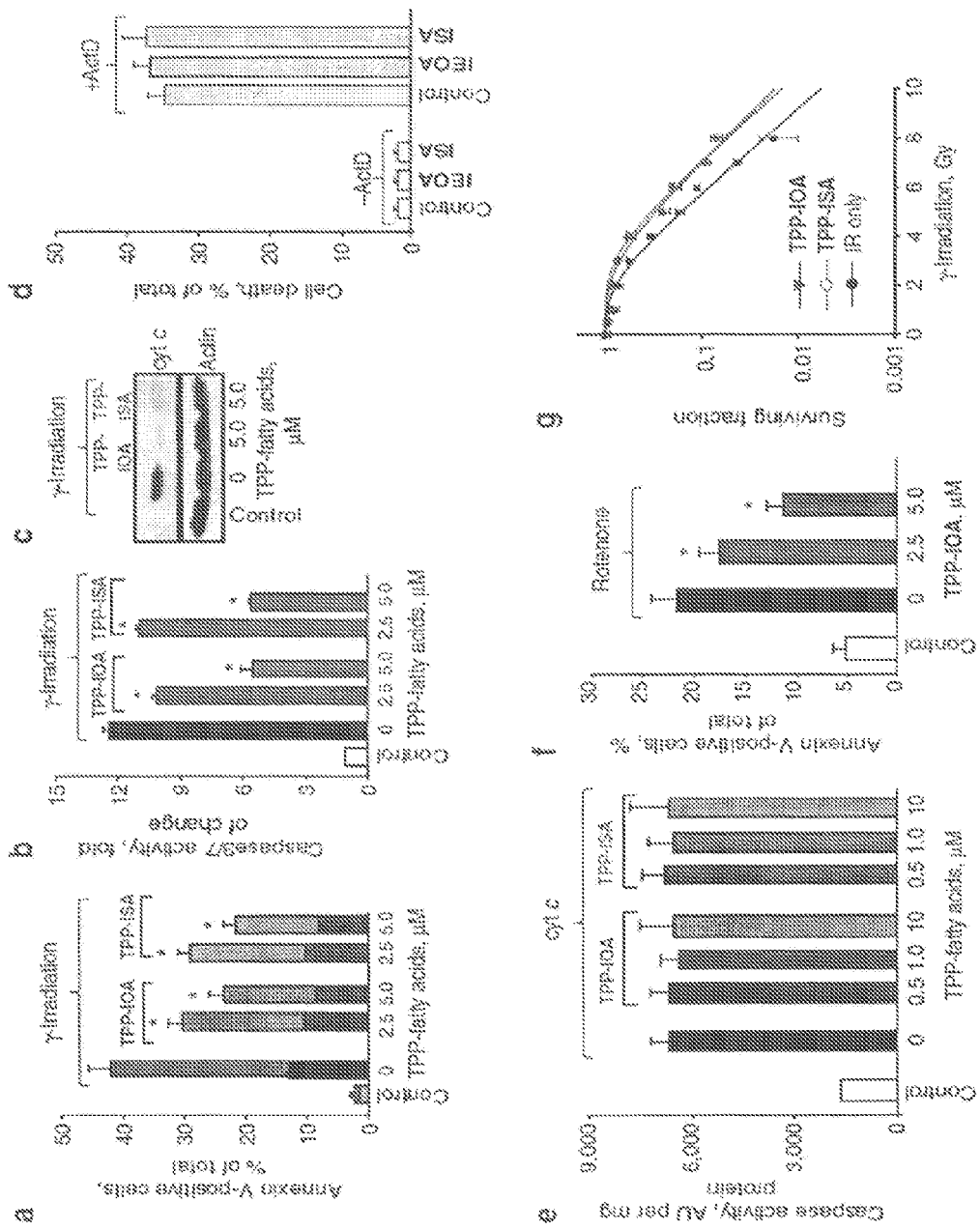
FIG. 7 shows mitigative effects of TPP-ISA and TPP-IOA against apoptosis.
Figure 10:
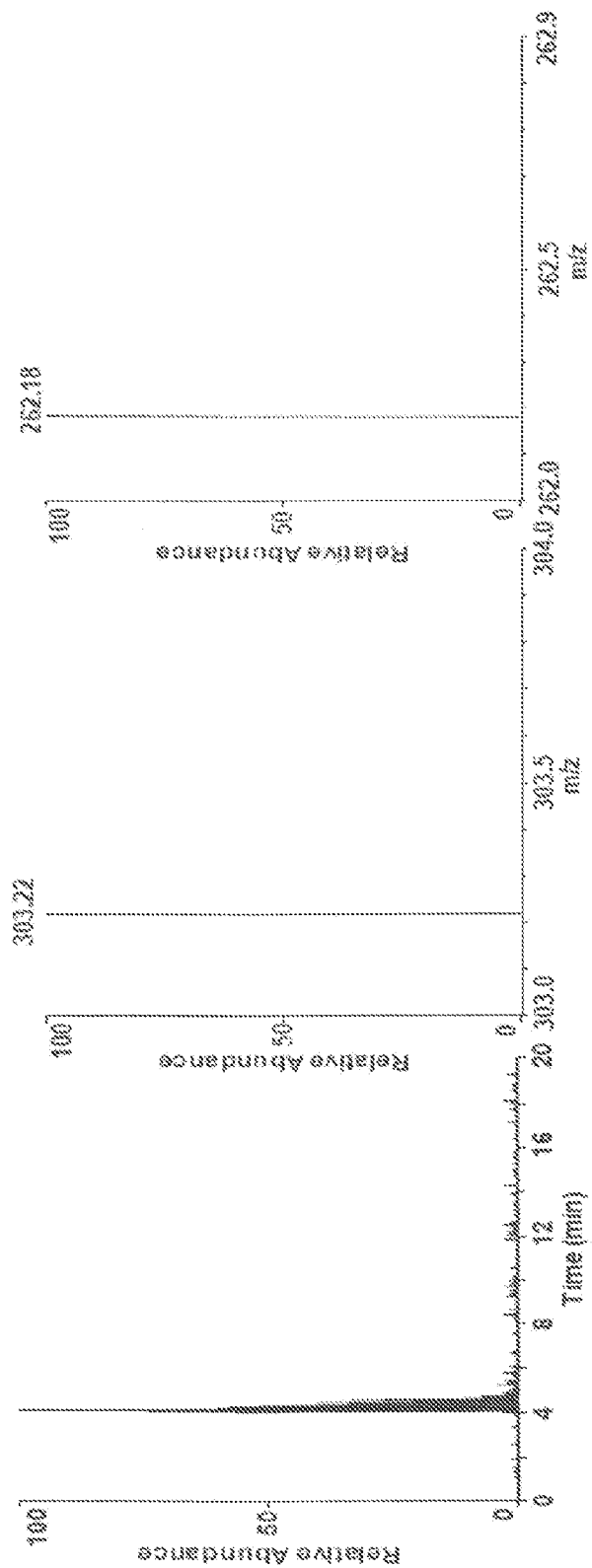
FIG. 10 shows multiple reaction monitoring (MRM) analysis of products formed during TPP-IOA hydrolysis. TPP-IOA hydrolysis was measured by the presence of the TPP-propyl group by MRM analysis. A small intestine sample (10 min time point) containing TPP-IOA hydrolysis products was chromatographed on a C18 column. The TPP-propyl group exhibited a retention time of 4.17 min (left panel). The transitions m/z 321→303 corresponding to TPP-propyl to TPP-propyl minus water (middle panel) and m/z 303→262 corresponding to TPP-propyl minus water to TPP, were measured (right panel).

In addition, the hydrolysis of TPP-IOA in tissues (plasma, bone marrow and small intestine) yielding TPP and non-esterified IOA was assessed utilizing two different LC-MS/MS approaches: a selected reaction monitoring method to determine the levels of IOA, a likely hydrolysis product of TPP-IOA, in tissue samples, and multiple reaction monitoring offering extremely high selectivity and sensitivity (FIG. 10). Using these approaches, it was determined that bone marrow had the least amount of hydrolysis; exhibiting a level of 0.6 ng per g tissue per min of the TPP-propyl hydrolysis product. This was followed by a level of 4.1 ng per g tissue per min and 19.0 ng per g tissue per min of the TPP hydrolysis product in plasma and small intestine, respectively. Simple calculations show that the total amounts of non-hydrolysed TPP-IOA plus hydrolysed (IOA+TPP) will be significantly (approximately two orders of magnitude) higher than those of the non-hydrolysed compound measured in the small intestine and bone marrow. The importance of this is underscored by the above data that both TPP-IOA and IOA are effective inhibitors of peroxidase activity of cyt c/CL complexes (FIG. 2) and CL peroxidation (FIG. 7).

Example 6

Preparation of (3-((6-(1H-imidazol-1-yl)octadecanoyl)oxy)propyl)triphenylphosphonium bromide A schematic for the synthesis of TPP-conjugated, C-18 fatty acids with an imidazole substitution at carbons 6 and 8 of the carbon chain by an ozonolysis methodology is shown in FIG. 11.

(a) Synthesis of Methyl 6-oxohexanoate

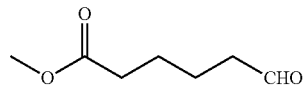

Cyclohexene (6.16 g, 75.02 mmol) and NaHCO$_3$ (2.0 g, 24.01 mmol) were added in 250 ml of dichloromethane, cooled to −78° C., then ozone gas was bubbled through the solution until a light blue color appeared. The ozone outlet was removed from the mixture and nitrogen gas bubbled through the solution to remove excess ozone, then the solution was allowed to warm to room temperature and filtered. 80 ml of benzene was added to the mixture and the volume reduced to 50 ml. The solution was diluted with another 225 ml of dichloromethane, cooled to 0° C., to which was added triethylamine (22 ml, 112.5 mmol) and acetic anhydride (19.63 ml, 225.1 mmol). The mixture was warmed to room temperature and stirring continued overnight. The mixture was diluted with 100 ml of dichloromethane, washed with 150 ml of 0.1N HCl, 150 ml of 10% NaOH solution, brine solution, dried on anhydrous MgSO$_4$, and concentrated.

Crude compound was distilled at 60° C. under 0.1 mm vacuum to obtain a colorless liquid (6.8 g, 63%).

$R_f$=0.5 (20% ethyl acetate in hexanes, iodine and KMnO$_4$ stain). $^1$H NMR (300 MHz, CDCl$_3$) δ 9.76 (t, 1H), 3.66 (t, 3H), 2.45 (m, 2H), 2.35 (m, 2H), 1.67 (q, 4H); $^{13}$C NMR (75 MHz, CDCl$_3$) δ 201.85, 173.43, 51.28, 43.26, 33.48, 24.17, 21.32; MS (+EI) m/z 145 [M+1]$^+$ (3.0%), 144 (1.2%), 143 (3.8%), 142 (5.4%), 129 (28.3%), 114 (45.9%), 113 (25.4%), 101 (51.5%), 100 (26.6%), 87 (53.4%), 74 (79.9%), 59 (100%), 55 (88.4%), 43 (82.4%), 41 (49.8%).

(b) Synthesis of methyl 6-hydroxyoctadecanoate

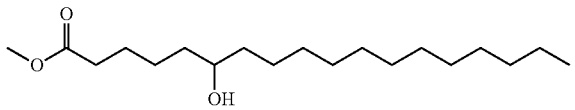 [SMILES: CCCCCCCCCCCCC(O)CCCCC(=O)OC]

Magnesium metal (0.359 g, 14.56 mmol) was added into dry THF (10 ml) in a 100 ml two-necked round bottom flask which was fitted with a condenser and a nitrogen gas inlet. The flask was heated to 70° C., then a few drops of 1,2 dibromoethane were added to the reaction mixture, followed by slow addition of 1-bromododecane (2.92 g, 11.726 mmol) at reflux. Stirring was continued for another 30 min. After cooling, the Grignard reagent was added dropwise to a stirred solution of methyl 6-oxohexanoate (1.31 g, 11.49 mmol) in THF (15 ml) at −20° C. The reaction mixture was slowly brought to room temperature after addition, and stirring continued for another 2 h. The mixture was quenched with saturated ammonium chloride solution, extracted with (3×40 ml) of ethyl acetate, and the combined organic layers were washed with brine solution, dried on anhydrous MgSO$_4$, concentrated and purified on silica gel (2:8 ethyl acetate and hexanes) to offer a white coloured solid (1.55 g, 47%).

$R_f$=0.42 (20% ethyl acetate in hexanes, iodine and KMnO$_4$ stain). $^1$H NMR (300 MHz, CDCl$_3$) δ 3.68 (s, 3H), 3.60 (m, 1H), 2.34 (t, 2H), 1.65 (m, 2H), 1.47 (m, 8H), 1.27 (s, 19H), 0.89 (t, 3H); $^{13}$C NMR (75 MHz, CDCl$_3$) δ 174.16, 71.55, 51.42, 37.49, 36.95, 33.97, 31.88, 29.67, 29.61, 29.31, 25.63, 25.17, 24.87, 22.64, 14.06; MS (EI) m/z 264 (4.8%), 158 (9.5%), 145 (20.8%), 113 (38.4%), 87(49%), 67(41.8%), 55(99.5%), 41(100%).

(c) Synthesis of methyl 6-(1H-imidazol-1-yl)octadecanoate

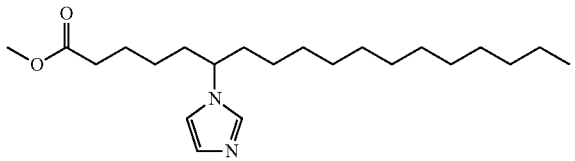 [SMILES: CCCCCCCCCCCCC(CCCCC(=O)OC)n1ccnc1]

Methanesulfonyl chloride (0.39 ml, 4.99 mmol) was added dropwise to a stirred solution of methyl 6-hydroxyoctadecanoate (1.55 g, 4.94 mmol) and triethylamine (0.89 ml, 6.42 mmol) in dry dichloromethane (30 ml) at 0° C. The reaction mixture was warmed to room temperature after the addition, and stirred for 2 h. The reaction mixture was quenched with water, diluted with 50 ml of dichloromethane, and the organic layer was washed with water and brine solution, dried on anhydrous MgSO$_4$, concentrated and evaporated under vacuum. This crude compound was combined with imidazole (0.67 g, 9.88 mmol) and heated at 80° C. for 16 h. Crude compound was purified on silica gel (2% methanol in dichloromethane) to obtain a light brown liquid (605 mg, 33.7%).

$^1$H NMR (300 MHz, CDCl$_3$) δ 7.46 (s, 1H), 7.07 (s, 1H), 6.87 (s, 1H), 3.88 (m, 1H), 3.63 (s, 3H), 2.24 (t, 2H), 1.71-1.48 (m, 6H), 1.23-1.11 (m, 22H), 0.86 (t, 3H); $^{13}$C NMR (75 MHz, CDCl$_3$) δ 173.75, 58.47, 51.48, 36.27, 35.98, 33.67, 31.87, 29.58, 29.55, 29.47, 29.36, 29.30, 29.16, 26.02, 25.56, 24.40, 22.65, 14.08; MS (+EI) m/z 364 (8.6%), 363 (10.7%), 333 (5%), 250 (7.0), 249 (32.2%), 195 (13.8%), 95 (24.3%), 82 (15.3%), 81(16.0%), 69 (100%), 57 (20.2%), 55 (41.7%), 43 (81.9%).

(d) Synthesis of 6-(1H-imidazol-1-yl)octadecanoic acid

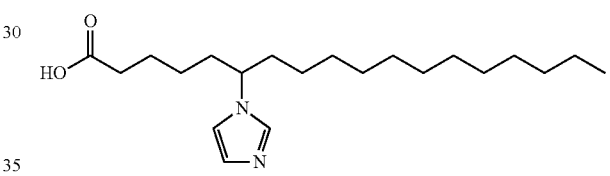

Sodium hydroxide (0.11 g, 2.75 mmol) was added to a stirred solution of methyl 6-(1H-imidazol-1-yl)octadecanoate (0.5 g, 1.37 mmol) in a mixture of methanol (9 ml) and water (3 ml) at 0° C., warmed to room temperature, and stirring continued for another 3 hours. Methanol was removed from the mixture by evaporation. The aqueous layer was acidified with 1N HCl up to pH 4, extracted with dichloromethane (3×15 ml), and the combined organic layers were washed with brine solution, dried on anhydrous MgSO$_4$, and concentrated. Crude product was purified on silica gel column (5% methanol in dichloromethane) to obtain a gummy liquid (370 mg, 77%).

$^1$H NMR (300 MHz, CDCl$_3$) δ 12.95 (s, 1H), 7.80 (s, 1H), 7.13 (s, 1H), 6.92 (s, 1H), 4.0 (m, 1H), 2.28 (m, 2H), 1.80-1.51 (m, 6H), 1.25 (m, 22H), 0.88 (t, 3H); $^{13}$C NMR (75 MHz, CDCl$_3$) δ 178.98, 135.96, 126.87, 116.68, 59.27, 36.17, 35.79, 34.47, 31.89, 29.61, 29.56, 29.49, 29.35, 29.35, 29.32, 29.16, 26.03, 25.35, 24.48, 22.67, 14.10; MS (+EI) m/z 351 (2.5%), 350 (10.5%), 349 (10.2%), 249 (46.3%), 181 (14.2%), 95 (23.3%), 69 (100%), 55 (38%), 43 (58%), 41(63%).

(e) Synthesis of (3-((6-(1H-imidazol-1-yl)octadecanoyl)oxy)propyl)triphenylphosphonium bromide

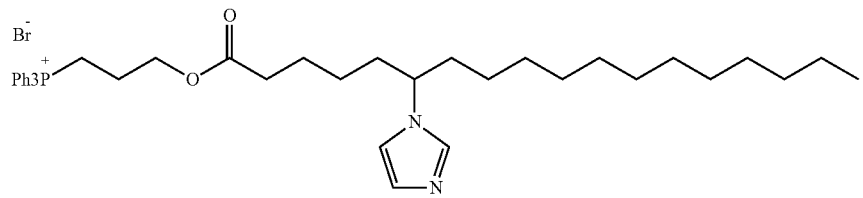

6-(1H-imidazol-1-yl)octadecanoic acid (300 mg, 0.857 mmol) and (3-hydroxypropyl)triphenylphosphonium bromide (344 mg, 0.858 mmol) were dissolved in dry dichloromethane, cooled to 0° C. to which was then added DCC (177 mg, 0.858 mmol). The mixture was warmed to room temperature and stirring continued for another 16 h. The mixture was filtered and concentrated, then purified by silica gel column (6% methanol in dichloromethane) to obtain a gummy liquid (420 mg, 67%).

$R_f$=0.43 (15% methanol in dichloromethane, iodine and $KMnO_4$ stain). $^1$H NMR (600 MHz, $CDCl_3$) δ 7.74-7.60 (m, 15H), 7.38 (s, 1H), 6.89 (s, 1H), 6.80 (s, 1H), 4.20 (s, 2H), 3.80 (m, 3H), 2.09 (m, 2H), 1.86 (d, 2H), 1.58 (t, 4H), 1.44 (s, 1H), 1.35 (s, 1H), 1.11 (m, 22H), 0.93 (s, 2H), 0.73 (t, 3H); $^{13}$C NMR (151 MHz, $CDCl_3$) δ 172.84, 136.29, 135.16, 135.15, 133.62, 133.56, 130.57, 130.48, 128.96, 118.06, 117.49, 116.50, 63.15, 63.03, 58.4, 36.16, 35.85, 33.68, 31.77, 29.48, 29.45, 29.38, 29.28, 29.19, 29.09, 25.93, 25.42, 24.17, 22.55, 22.10, 19.89, 19.54, 14.03; MS (FAB) m/z: 655 (11.7%), 654 (M+1, 46.9%), 653 (M+, 100%), 375 (6.6%), 319 (12.1%), 303 (10.5%), 289 (8.3%), 275 (11%), 262 (12.7%), 185 (6.9%), 183 (11.5%), 69 (30.8%).

Example 7

Preparation of (3-((8-(1H-imidazol-1-yl)octadecanoyl)oxy)propyl)triphenylphosphonium bromide A schematic for the synthesis of TPP-conjugated, C-18 fatty acids with an imidazole substitution at carbons 6 and 8 of the carbon chain by an ozonolysis methodology is shown in FIG. 11.

(a) Synthesis of methyl 8-oxooctanoate

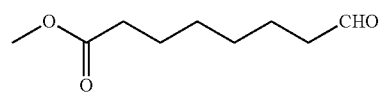

Cis-cyclooctene (10 g, 90.74 mmol) and $NaHCO_3$ (2.44 g, 29.05 mmol) were suspended in 400 ml of dichloromethane, cooled to −78° C., then ozone gas was bubbled through the solution until a light blue color appeared. The ozone outlet was removed from the mixture and nitrogen gas bubbled through the solution to remove excess ozone, and it was allowed to warm to room temperature and filtered. 100 ml of benzene was added to the mixture and the volume reduced by evaporation to 100 ml. The solution was diluted with another 400 ml of dichloromethane, cooled to 0° C., triethylamine (18.94 ml, 136.1 mmol) and acetic anhydride (25.7 ml, 272.2 mmol) were added, the ice bath removed, and stirring continued overnight at room temperature. The mixture was diluted with 200 ml of dichloromethane, washed with 200 ml of 0.1N HCl, 200 ml of 10% NaOH solution, brine solution, dried on anhydrous $MgSO_4$, and concentrated. Crude compound was distilled at 96° C. under 0.1 mm vacuum to obtain a colorless liquid (10.9 g, 70%).

$R_f$=0.45 (20% Ethyl acetate in hexanes, iodine and $KMnO_4$ stain). $^1$H NMR (300 MHz, $CDCl_3$) δ 9.52 (t, 1H, J=3 Hz), 3.41 (t, 3H), 2.21-2.17 (m, 2H), 2.08-2.03 (m, 2H), 1.40 (m, 4H), 1.12 (m, 4H); $^{13}$C NMR (75 MHz, $CDCl_3$) δ 202.04, 173.56, 51.00, 43.41, 33.53, 28.54, 28.48, 24.40, 21.55; MS (EI) m/z 173 [M+1]$^+$ (2.4%), 171 (5.4%), 157 (24.35%), 138 (49.7%), 129 (24.6%), 97 (32.9%), 87 (37.3%), 74 (100%), 69 (50.7%).

(b) Synthesis of methyl 8-hydroxyoctadecanoate

Magnesium metal (0.209 g, 8.71 mmol) was added into dry THF (10 ml) in a 50 ml two-necked round bottom flask fitted with a condenser and nitrogen gas inlet. The flask was heated to 70° C., then a few drops of 1,2 dibromoethane were added to the mixture, followed by the slow addition of 1-bromodecane (1.3 g, 5.81 mmol) while at reflux temperature. Stirring was continued for 30 min. After cooling, the Grignard reagent was added dropwise to a stirred solution of methyl 8-oxooctanoate (1.0 g, 5.8 mmol) in THF (10 ml) at −20° C., and the reaction mixture was slowly warmed to room temperature, where stirring was continued for 2 h. The mixture was quenched with saturated ammonium chloride solution, extracted with (3×25 ml) of ethyl acetate, and the combined organic layers were washed with brine solution, dried on anhydrous MgSO₄, concentrated and purified on silica gel (2:8 ethyl acetate and hexanes) to obtain an off-white solid (450 mg, 47%).

(c) Synthesis of methyl 8-(1H-imidazol-1-yl)octadecanoate

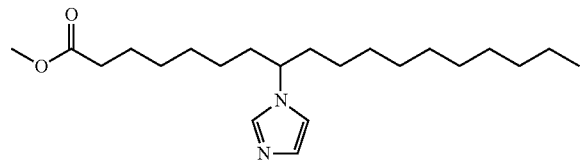 [SMILES: CCCCCCCCCCC(CCCCCCC(=O)OC)n1ccnc1]

To a stirred solution of methyl 8-hydroxyoctadecanoate (0.92 g, 2.93 mmol) 4-dimethylaminopyridine (30 mg) and triethylamine (0.42 ml, 6.42 mmol) in dry dichloromethane (30 ml) at 0° C., was added methanesulfonyl chloride (0.23 ml, 2.96 mmol). The reaction mixture was allowed to warm up to room temperature after the addition, and stirred for 2 h. The reaction mixture was quenched with water, diluted with 30 ml of dichloromethane. The organic layer was washed with water and brine solution, dried on anhydrous MgSO₄, concentrated and dried under vacuum. This crude compound was mixed with imidazole (0.45 g, 5.86 mmol) then heated at 80° C. for 16 h. Crude compound was purified on silica gel (3:7 ethyl acetate in dichloromethane) to obtain a light brown liquid (370 mg, 35%).

$R_f$=0.4 (5% methanol in dichloromethane, iodine and KMnO₄ stain). ¹H NMR (300 MHz, CDCl₃) δ 7.46 (s, 1H), 7.07 (s, 1H), 6.88 (s, 1H), 3.91-3.82 (m, 1H), 3.65 (s, 3H), 2.31-2.24 (t, 2H), 1.77-1.54 (m, 6H), 1.23-1.16 (m, 22H), 1.13-1.09 (t, 3H); ¹³C NMR (75 MHz, CDCl₃) δ 174.09, 129.41, 116.45, 58.70, 51.43, 36.30, 36.23, 33.91, 31.85, 29.51, 29.48, 29.36, 29.25, 29.19, 28.83, 26.04, 25.88, 24.73, 22.63, 14.07; MS (EI) m/z 364 (14.8%), 363 (21.1%), 333 (10.8%), 224(12.1%), 223 (63%), 222 (19.5%), 221(100%), 69 (85.5%), 55 (21.1%).

(d) Synthesis of 8-(1H-imidazol-1-yl)octadecanoic acid

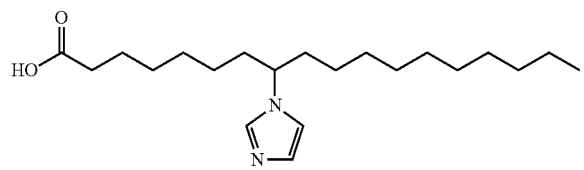 [SMILES: CCCCCCCCCCC(CCCCCCC(=O)O)n1ccnc1]

Sodium hydroxide (0.67 g, 1.68 mmol) was added to a stirred solution of 8-(1H-imidazol-1-yl)octadecanoate (0.305 g, 0.84 mmol) in a mixture of methanol (9 ml) and water (3 ml) at 0° C., warmed to room temperature and stirring continued another 3 h. Methanol was removed from the mixture by evaporation. The pH was adjusted to 4 with 1N HCl, and the mixture extracted with dichloromethane (3×15 ml). The combined organic layers were washed with brine solution, dried on anhydrous MgSO₄, and concentrated. Crude product was purified on silica gel column (5% methanol in dichloromethane) to obtain a gummy liquid (370 mg, 83%).

¹H NMR (300 MHz, CDCl₃) δ 8.73 (s, 1H), 8.68 (s, 1H), 7.33 (s, 1H), 7.05 (s, 1H), 4.18 (q, 1H), 2.29 (m, 2H), 1.80-1.54 (m, 6H), 1.33-1.06 (m, 22H), 0.87 (m, 3H); ¹³C NMR (75 MHz, CDCl₃) δ 131.93, 130.90, 128.83, 59.36, 36.20, 36.14, 31.86, 29.52, 29.49, 29.36, 29.26, 29.17, 28.91, 28.87, 26.04, 25.89, 24.91, 22.66, 14.10; MS (+EI) m/z 351 (2.8%), 350 (8.0%), 230 (14.7%), 222 (20.9%), 221 (100%), 213 (37.8%), 215 (67.7%), 209 (60.4%), 202 (65.4%), 201 (41.1%).

(e) Synthesis of (3-((8-(1H-imidazol-1-yl)octadecanoyl)oxy)propyl)triphenylphosphonium bromide

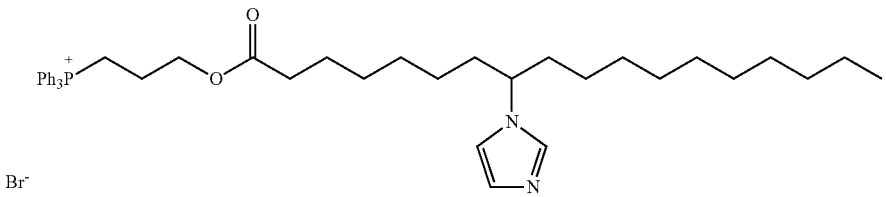

8-(1H-imidazol-1-yl)octadecanoic acid (225 mg, 0.643 mmol) and (3-hydroxypropyl)triphenylphosphonium bromide (258 mg, 0.643 mmol) were dissolved in dry dichloromethane, cooled to 0° C., then added N,N'-dicyclohexylcarbodiimide (146 mg, 0.708 mmol), warmed to room temperature and stirring continued for another 16 h. The mixture was filtered and concentrated, purified by silica gel column (5.5% methanol in DCM) to obtain a gummy liquid (330 mg, 70%).

$R_f$=0.43 (15% Methanol in dichloromethane, iodine and KMnO₄ stain). ¹H NMR (600 MHz, CDCl₃) δ 7.79-7.63 (m, 15H), 7.45 (s, 1H), 6.97 (s, 1H), 6.85 (s, 1H), 4.27 (t, 2H), 3.83 (m, 3H), 2.15 (m, 2H), 1.94 (m, 2H), 1.64 (m, 4H), 1.42 (t, 2H), 1.21-1.13 (m, 22H), 0.98 (m, 2H), 0.79 (t, 3H); ¹³C NMR (151 MHz, CDCl₃) δ 173.23, 136.28, 135.21, 135.19, 135.11, 133.66, 133.59, 133.47, 133.41, 130.61, 130.52, 130.44, 130.40, 128.85, 118.12, 117.55, 116.56, 77.45, 77.23, 77.02, 63.12, 63.00, 58.80, 36.23, 36.14, 33.90, 31.83, 31.79, 29.55, 29.51, 29.46, 29.43, 29.33, 29.26, 29.20, 29.14, 28.76, 28.75, 26.00, 25.82, 24.53, 22.59, 22.20, 19.93, 19.57, 14.07; MS (FAB) m/z 654 (M+1, 43.4%), 653 (M+, 91.9%), 603 (10.3%), 375 (12.8%), 319 (18.3%), 303 (16.2%), 289 (13.1%), 275 (18.1%), 185 (13.6%), 183 (20.3%), 69 (100%).

Example 8

Preparation of (3-((13-(1H-imidazol-1-yl)octadecanoyl)oxy)propyl)triphenylphosphonium bromide (TPP-13-ISA)

Figure 12A:
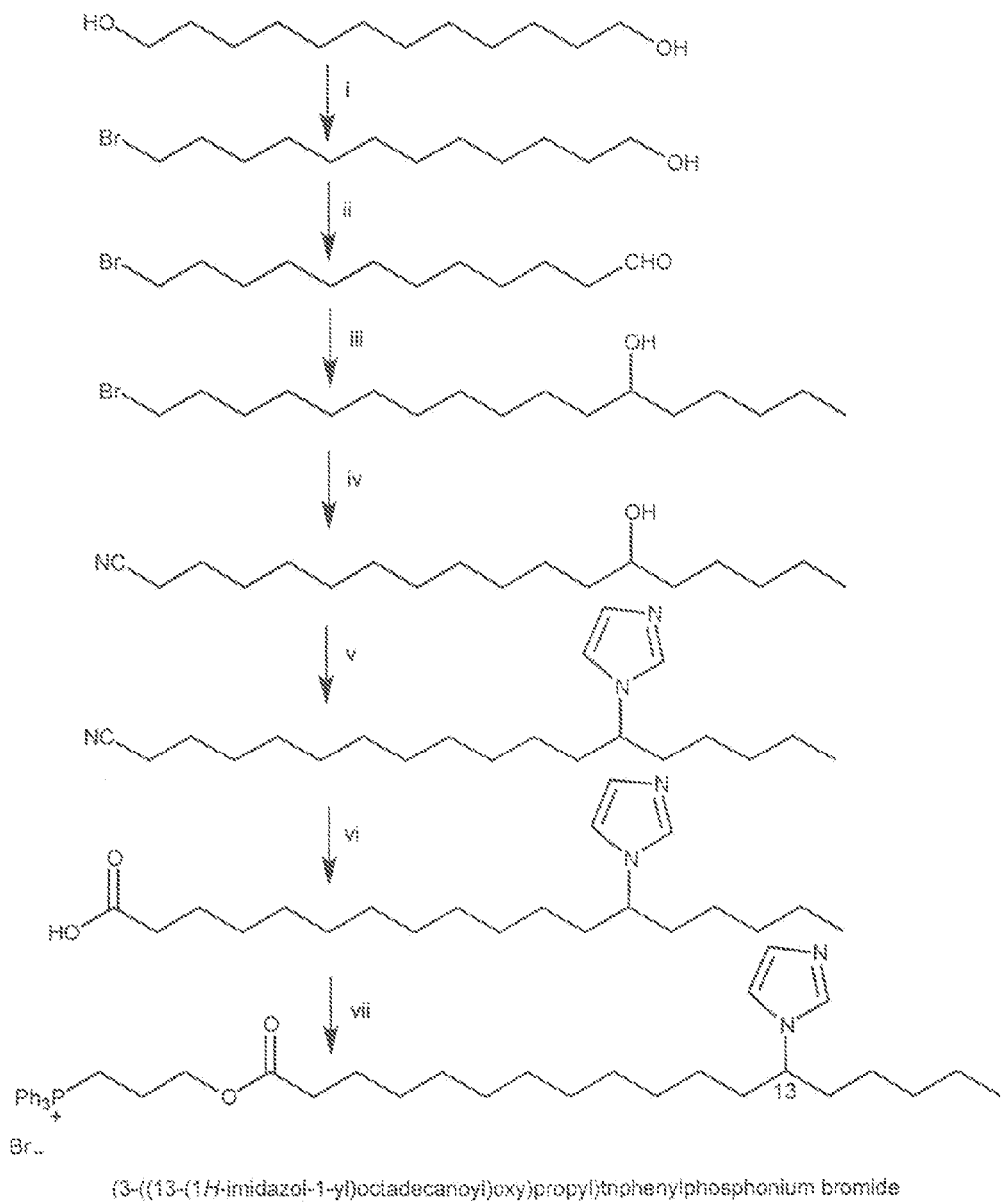
FIG. 12A shows the synthesis of TPP-13-ISA. Reaction Conditions: (i) 48% HBr in $H_2O$, toluene and reflux, 3h, 78%; (ii) PCC, DCM, 4h, 72%; (iii) 1-bromopentane, Mg, THF, cat. $I_2$, 58%; (iv) NaCN, dry DMF, 90° C. 16 hr, 92%; (v) $CH_3SO_2Cl$, TEA, DMAP, DCM, 0° C. to RT, then imidazole, 70° C., 16h, 32%; (vi) $EtOH:H_2O$ (2:1), NaOH, reflux, 16 hr, 81%; (vii) (3-hydroxypropyl)triphenylphosphonium bromide, cat. DMAP, DCC, DCM, 78%.
Figure 12B:
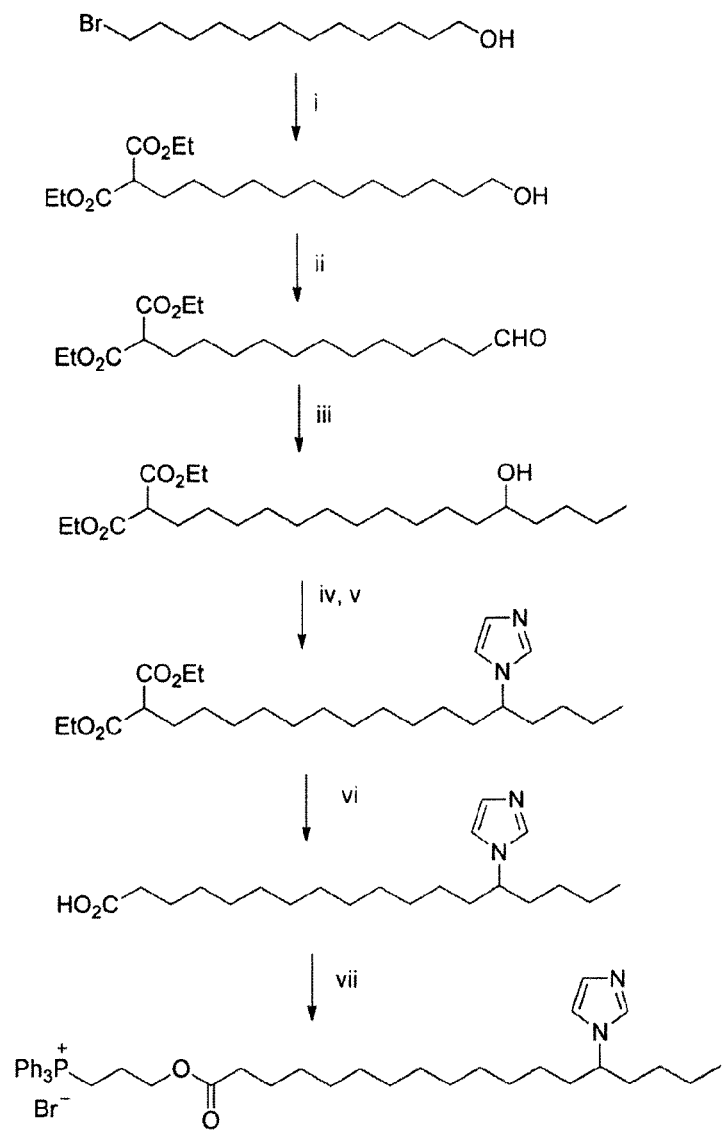
FIG. 12B shows the synthesis of TPP-14-ISA. Reaction Conditions: (i) $K_2CO_3$, KI, $CH_2(COOEt)_2$, acetonitrile, 90° C., 48h, 63%; (ii) PCC, DCM, 3h, 73%; (iii) 1-bromobutane, Mg, THF, 4h, 62.5%; (iv) methane sulfonyl chloride, TEA, DMAP, DCM, 3h; (v) imidazole, 75° C., 16h, 32.5%; (vi) NaOH, NeOH:$H_2O$ (3:1), 3h; & 170° C., 20 mins, 68%; (vii) TPP propanol, DCC, DMAP, DCM, 16h, 71%.

A schematic for the synthesis of TPP-conjugated, C-18 fatty acids with an imidazole substitution at carbon 13 of the carbon chain is shown in FIG. 12A.

(a) Synthesis of 12-bromododecan-1-ol

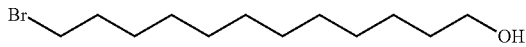 [SMILES: OCCCCCCCCCCCCBr]

To a stirred solution of dodecane-1,12-diol (8.365 g, 42.75 mmol), 48% HBr in water (9.7 ml, 85.50 mmol) and toluene (120 ml) were added and the reaction mixture refluxed for 3 h. The reaction mixture was then concentrated, the crude compound was dissolved in DCM (150 ml), washed with water, NaHCO$_3$ brine solution, dried over MgSO$_4$ and concentrated. The crude product was purified by silica gel column (5% EtOAc in hexane) to obtain 12-bromododecan-1-ol as an off-white low melting solid (8.87 g, 78%).

$R_f$=0.55 (10% EtOAc in Hexane, KMnO$_4$ active.). $^1$H NMR (300 MHz, CDCl$_3$) δ 3.63 (t, 2H), 3.40 (t, 2H), 3.85 (m, 2H), 1.59-1.51 (m, 2H), 1.44-1.27 (m, 16H); $^{13}$C NMR (75 MHz, CDCl$_3$) δ 62.91, 34.00, 32.82, 32.74, 29.56, 29.50, 29.41, 29.22, 28.74, 28.15, 25.73; MS (EI) m/z 220 (3.6%), 164 (8.7%), 162 (8.1%), 150 (13.7%), 148 (13.6%), 97 (31.9%), 83 (45.4%), 82 (58.7%), 69 (66.7%), 68 (54.2%), 55 (100%), 41 (57.9%); HRMS Calculated: 264.1089. Found: [M−18]$^+$=246.09741.

(b) Synthesis of 12-bromododecanal

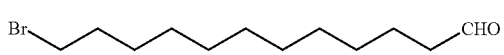 [SMILES: O=CCCCCCCCCCCCBr]

12-bromododecan-1-ol (6 g, 22.62 mmol) was dissolved in dry DCM (90 ml) and cooled to 0° C., to which was then added PCC (7.32 g, 33.93 mmol) portion wise. The solution was warmed to room temperature and stirring continued another 4 h. The reaction mixture was concentrated and purified by silica gel column (6% EtOAc in hexane) to offer 12-bromododecanal as a colorless liquid (4.3 g, 72%).

$R_f$=0.45 (10% EtOAc in hexane, KMnO$_4$ active); $^1$H NMR (300 MHz, CDCl$_3$) δ 9.76 (t, 1H), 3.41 (t, 2H), 2.42 (m, 2H), 1.85 (m, 2H), 1.63 (m, 2H), 1.44-1.28 (m, 14H); $^{13}$C NMR (75 MHz, CDCl$_3$) δ 202.94, 43.88, 34.01, 32.80, 29.40, 29.36, 29.33, 29.30, 29.19, 29.12, 29.03, 28.72, 28.58, 28.14, 24.71, 22.05; MS (EI) m/z [M+1]$^+$ 263 (1.5%), 261 (1.6%), 220 (9.7%), 218 (13.7%), 150 (14.5%), 148 (14.6%), 135 (10.5%).

(c) Synthesis of 17-bromoheptadecan-6-ol

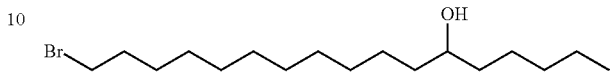

1-bromopentane (2.54 ml, 20.51 mmol) in THF (5 ml) was added dropwise to a stirred suspension of Mg metal (0.54 g, 22.23 mmol) and a catalytic amount of iodine in dry THF (15 ml) at 75° C., after which stirring was continued for another 30 minutes. The generated Grignard reagent was cooled to room temperature and added slowly to a stirred solution of 12-bromododecanal (4.5 g, 17.09 mmol) in THF (40 ml) at 0° C. The reaction was warmed to room temperature and stirring continued another 1.5 hours, then quenched with NH$_4$Cl solution, and extracted with EtOAc (3×50 ml). The combined organic layers were washed with brine solution, dried on MgSO$_4$ and concentrated. The crude compound was purified over silica gel column (8% EtOAc in hexane) to give 17-bromoheptadecan-6-ol as an off-white low melting solid (3.34 g, 58%).

$R_f$=0.54 (10% EtOAc in Hexane, KMnO$_4$ active); $^1$H NMR (300 MHz, CDCl$_3$) δ 3.60-3.56 (m, 1H), 3.41 (t, 2H), 1.85 (m, 2H), 1.47-1.28 (m, 28H), 0.89 (t, 3H); $^{13}$C NMR (151 MHz, CDCl$_3$) δ 71.98, 37.47, 37.45, 34.02, 32.83, 31.92, 29.70, 29.59, 29.54, 29.42, 28.75, 28.17, 25.65, 25.33, 22.65, 14.05; MS (EI) m/z [M+1]$^+$ 263 (1.5%), 261 (1.6%), 220 (9.7%), 218 (13.7%), 150 (14.5%), 148 (14.6%), 135 (10.5%); HRMS Calculated: 264.1089. Found: [M−18]$^+$=246.09741.

(d) Synthesis of β-hydroxyoctadecanenitrile

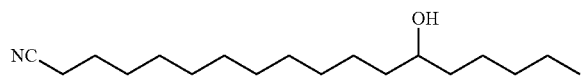 [SMILES: CCCCCC(O)CCCCCCCCCCCC#N]

To 17-bromoheptadecan-6-ol (1.0 g, 2.98 mmol) in dry DMF, was added NaCN (175 mg, 3.58 mmol) and the resulting reaction mixture heated at 90° C. for 16 hours. After cooling to room temperature, the mixture was diluted with diethyl ether (100 ml), the organic layer was washed with cold water (3×20 ml), brine solution, dried over MgSO$_4$ and concentrated. The crude product was purified over a silica gel column (10% EtOAc in hexane) to give 13-hydroxyoctadecanenitrile as a colorless liquid (0.77 g, 92%).

$R_f$=0.55 (20% EtOAc in Hexane, KMnO$_4$ and Iodine active); $^1$H NMR (300 MHz, CDCl$_3$) δ 3.60-3.56 (m, 1H), 3.41 (t, 2H), 1.85 (q, 2H), 1.47-1.28 (m, 27H), 0.92-0.87 (m, 3H); $^{13}$C NMR (151 MHz, CDCl$_3$) δ 119.82, 71.88, 62.51, 37.42, 34.83, 31.91, 29.67, 29.55, 29.48, 29.43, 29.25, 28.71, 28.61, 25.62, 25.32, 22.63, 18.88, 17.07, 14.03, 13.84; MS (EI) m/z [M−18]$^+$ 263 (9.8%), 211 (18.6%), 210 (100%), 136

(25.5%), 122 (29.9%), 100 (30.3%), 97(32.4%), 83 (46.2%), 55 (66.5%); HRMS Calculated: 281.2719. Found: [M−18]+= 263.26080.

(e) Synthesis of 13-(1H-imidazol-1-yl)octadecanenitrile

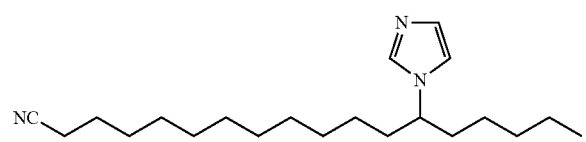 [SMILES: CCCCCC(CCCCCCCCCCCC#N)n1ccnc1]

To a stirred solution of β-hydroxyoctadecanenitrile (4.5 g, 15.99 mmol), TEA (2.9 ml, 20.78 mmol) and DMAP (0.19 g, 1.59 mmol) in dry DCM (70 ml) cooled to 0° C., was added methanesulfonyl chloride (1.3 ml, 16.78 mmol) under $N_2$. After allowing the reaction mixture to warm to room temperature, stirring was continued for another 2 hours. The reaction mixture was diluted with DCM (100 ml), the organic layer was washed with 1N HCl, water and brine solution, dried over $MgSO_4$ and concentrated under reduced pressure. This crude compound was mixed with imidazole (2.18 g, 31.97 mmol) and heated at 70° C. for 16 hours under $N_2$. The crude product was purified by silica gel column (2% MeOH in DCM) to give 13-(1H-imidazol-1-yl)octadecanenitrile as a light yellow liquid (1.64 g, 32%).

$R_f$=0.58 (10% MeOH in DCM, $KMnO_4$ and Iodine active); $^1$H NMR (300 MHz, $CDCl_3$) δ 7.44 (s, 1H), 7.05 (s, 1H), 6.87 (s, 1H), 3.86 (m, 1H), 2.31 (t, 2H), 1.73-1.58 (m, 6H), 1.41 (m, 2H), 1.25-1.05 (m, 20H), 0.85-0.80 (m, 3H); $^{13}$C NMR (75 MHz, $CDCl_3$) δ 136.49, 129.37, 119.83, 116.39, 58.68, 36.30, 36.27, 31.35, 29.34, 29.19, 29.16, 28.68, 28.59, 26.03, 25.71, 25.31, 22.39, 17.08, 13.91; MS (EI) m/z [M]+ 331 (3.9%), 261 (66.3%), 152 (17.4%), 151 (100%), 69 (50.5%), 55 (20.9%), 41 (23.7%); HRMS Calculated: 331.2987. Found: [M−18]+=331.29944.

(f) Synthesis of 13-(1H-imidazol-1-yl)octadecanoic acid

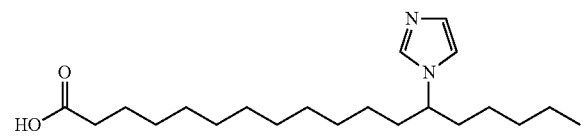 [SMILES: CCCCCC(CCCCCCCCCCCC(=O)O)n1ccnc1]

13-(1H-imidazol-1-yl)octadecanenitrile (550 mg, 1.66 mmol) was dissolved in EtOH (10 ml) and water (5 ml), to which was then added NaOH (332 mg, 8.30 mmol) and the mixture refluxed for 16 hr. The reaction mixture was then concentrated and acidified with 1N HCl, extracted with DCM, washed with brine solution, dried over $MgSO_4$ and concentrated. The crude product was purified by silica gel column (4% MeOH in DCM) to give 13-(1H-imidazol-1-yl)octadecanoic acid as a thick oil (470 mg, 81%).

$R_f$=0.52 (10% MeOH in DCM, $KMnO_4$ and Iodine active); $^1$H NMR (300 MHz, $CDCl_3$) δ 9.81 (s, 1H), 8.60 (s, 1H), 7.34 (s, 1H), 7.05 (s, 1H), 4.14 (m, 1H), 2.31 (s, 2H), 1.76 (m, 4H), 1.61 (m, 2H), 1.22-1.20 (m, 22H), 1.06 (m, 2H), 0.83 (s, 1H); $^{13}$C NMR (75 MHz, $CDCl_3$) δ 177.81, 60.96, 35.76, 34.44, 31.21, 29.18, 29.13, 29.01, 28.97, 28.90, 25.77, 25.55, 24.88, 22.32, 13.88.

(g) Synthesis of (3-((13-(1H-imidazol-1-yl)octadecanoyl)oxy)propyl)triphenylphosphonium bromide (TPP-13-ISA)

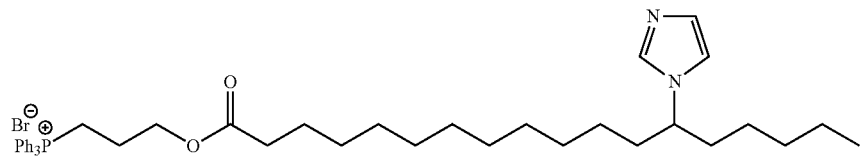

A stirred solution of 13-(1H-imidazol-1-yl)octadecanoic acid (365 mg, 1.041 mmol), (3-hydroxypropyl)triphenylphosphonium bromide (418 mg, 1.041 mmol) and DMAP (catalytic amount) in DCM (10 ml), was cooled to 0° C., to which was then added DCC (215 mg, 1.041 mmol) under $N_2$ gas, and stirring continued overnight at room temperature. The reaction mixture was filtered and concentrated. The crude product was purified by silica gel column (5% MeOH in DCM) to give TPP-13-ISA as a gummy semi-solid (600 mg, 78%)

$^1$H NMR (300 MHz, $CDCl_3$) δ 7.89-7.84 (m, 6H), 7.82-7.79 (m, 3H), 7.72-7.69 (m, 6H), 7.48 (s, 1H), 7.06 (s, 1H), 6.90 (s, 1H), 4.38-4.36 (m, 2H), 4.02-3.97 (m, 3H), 2.42 (t, 4H), 2.02-2.00 (m, 2H), 1.73-1.68 (m, 4H), 1.54-1.52 (m, 2H), 1.25-1.06 (m, 22H), 0.85-0.82 (m, 3H); $^{13}$C NMR (151 MHz, $CDCl_3$) δ: 173.49, 135.16, 133.76, 133.70, 133.60, 130.52, 118.33, 117.76, 68.12, 63.00, 58.83, 36.31, 36.28, 34.16, 31.37, 29.47, 29.43, 29.37, 29.23, 29.19, 29.09, 26.07, 25.74, 24.83, 22.43, 22.28, 19.96, 19.61, 13.96; MS (EI) m/z [M+1]+ (16.2%), [M]+ 653 (34.5%), 183 (11.5%), 95 (15.1%), 77 (10.1%), 69 (100.0%), 57 (18.5%), 55 (31.2%), 43 (24.2%), 41 (26.4%); HRMS Calculated: 653.4230. Found: 653.42199.

Example 9

Preparation of (3-((14-(1H-imidazol-1-yl)octadecanoyl)oxy)propyl)triphenylphosphonium bromide (TPP-14-ISA)

(a) Synthesis of diethyl 2-(12-hydroxydodecyl)malonate

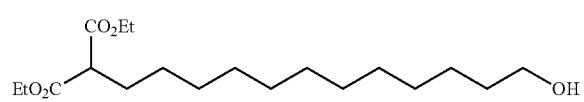

12-bromododecan-1-ol (6.54 g, 24.658 mmol), $K_2CO_3$ (8.52 g, 61.645 mmol), KI (0.409 g, 2.466 mmol) and diethylmalonate (7.52 ml, 48.316 mmol) were added to dry acetonitrile (100 ml), then the mixture was heated at 90° C. for 48 h. The reaction mixture was filtered to remove the solid materials and the filtrate was concentrated. The crude compound was purified by silica gel column (7-10% EtOAc in hexane) to give diethyl 2-(12-hydroxydodecyl)malonate (5.35 g, 63%) as a colorless compound.

$R_f$=0.43 (30% EtOAc in hexane, iodine and $KMnO_4$ active); $^1H$ NMR (300 MHz, $CDCl_3$) δ 4.20-4.13 (q, 4H), 3.60 (t, 2H), 3.29 (t, 1H), 1.87-1.82 (m, 2H), 1.74 (s, 1H), 1.56-1.49 (m, 2H), 1.28-1.22 (m, 24H); $^{13}C$ NMR (75 MHz, $CDCl_3$) δ: 169.59, 62.92, 61.20, 52.04, 32.75, 29.54, 29.49, 29.43, 29.39, 29.24, 29.15, 28.69, 27.26, 25.71, 14.03; MS (EI) m/z: 344 (4.7%), 173 (56.8%), 160 (100%), 55 (40.5%), 45 (47.1%), 44 (46.6%); HRMS Calculated: 344.2563. Found: 344.25495.

(b) Synthesis of diethyl 2-(12-oxododecyl)malonate

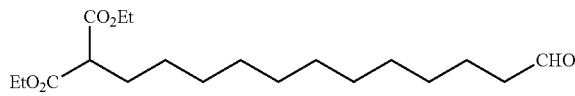 [SMILES: CCOC(=O)C(CCCCCCCCCCCC=O)C(=O)OCC]

Diethyl 2-(12-hydroxydodecyl)malonate (3.91 g, 11.35 mmol) was dissolved in dry DCM (60 ml), then PCC (3.67 g, 17.025 mmol) was added portion-wise to it at 0° C. The reaction was allowed to warm to room temperature and stirring was continued for another 3 h. The reaction mixture was concentrated under reduced pressure and purified by silica gel column (8% EtOAc in Hexane) to give diethyl 2-(12-oxododecyl)malonate (2.84 g, 73%) as a colorless liquid.

$R_f$=0.4 (20% EtOAc in Hexane, Iodine and $KMnO_4$ active); $^1H$ NMR (300 MHz, $CDCl_3$) δ 9.73 (t, 3H), 4.20-4.13 (q, 4H), 3.28 (t, 1H), 2.42-2.36 (m, 2H), 1.89-1.82 (m, 2H), 1.64-1.55 (m, 2H), 1.28-1.26 (m, 22H); $^{13}C$ NMR (75 MHz, $CDCl_3$) δ 202.81, 169.53, 61.16, 52.01, 43.84, 29.42, 29.39, 29.32, 29.27, 29.22, 29.13, 29.09, 28.68, 27.24, 22.02, 14.02; MS (FAB) m/z: 299 (5.9%), 173 (60.9%), 133 (15.7%), 127 (10.3%), 98 (20.7%), 95 (18.9%), 69 (23.2%), 55 (62.2%), 43 (34.2%), 41 (39.4%).

(c) Synthesis of diethyl 2-(12-hydroxyhexadecyl)malonate

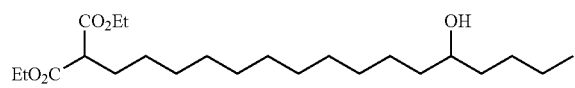 [SMILES: CCCCC(O)CCCCCCCCCCCC(C(=O)OCC)C(=O)OCC]

1-Bromobutane (0.92 ml, 8.512 mmol) in dry THF (5 ml) was slowly added to a stirred suspension of Mg metal (0.25 g, 10.059 mmol) and a catalytic amount of Iodine in dry THF (10 ml) at reflux temperature, and the reaction mixture stirred for 30 min after the completion of the addition. The prepared Grignard reagent was cooled to room temperature, then added dropwise over 15 min to a stirred solution of diethyl 2-(12-oxododecyl)malonate (2.65 g, 7.738 mmol) in THF (30 ml) at −10 to −15° C. and stirred at this temperature for 30 min. The reaction mixture was slowly warmed to room temperature and stirring continued for another one hour. The reaction was quenched with saturated ammonium chloride solution (10 ml), diluted with water (20 ml), extracted with diethyl ether (3×50 ml), dried on anhydrous $MgSO_4$ and concentrated. The crude product was purified by silica gel column (4-6% EtOAc in hexane) and provided diethyl 2-(12-hydroxyhexadecyl)malonate (1.94 g, 62.5%) as a colorless liquid.

$R_f$=0.53 (20% EtOAc in Hexane, Iodine and KMnO4 active); $^1H$ NMR (300 MHz, $CDCl_3$) δ: 4.21-4.13 (q, 4H), 3.58-3.54 (3, 1H), 3.29 (t, 1H), 1.88-1.83 (m, 2H), 1.74 (s, 1H), 1.51-1.22 (m, 33H), 0.89 (t, 3H); $^{13}C$ NMR (75 MHz, $CDCl_3$) δ: 169.57, 71.90, 61.19, 52.04, 37.46, 37.15, 29.68, 29.58, 29.53, 29.45, 29.26, 29.17, 28.70, 27.82, 27.28, 25.62, 22.74, 14.05; MS (FAB) m/z: [M−18]⁺ 382 (1.5%), 343 (26.8%), 297 (14.9%), 251 (29.7%), 173 (100.0%), 161 (15.0%), 160 (77.8%), 98 (23.0%), 87 (20.5%), 73 (19.0%), 69 (47.6%), 55 (51.3%), 43 (26.6%), 41 (35.3%).

(d) Synthesis of diethyl 2-(12-(1H-imidazol-1-yl)hexadecyl)malonate

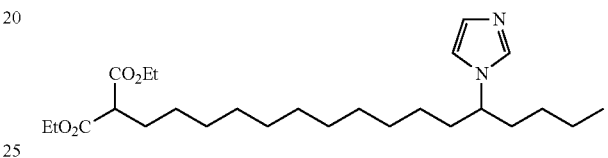

Diethyl 2-(12-hydroxyhexadecyl)malonate (1.75 g, 4.369 mmol), TEA (0.79 ml, 5.679 mmol) and DMAP (53 mg, 0.437 mmol) were dissolved in dry DCM (20 ml), cooled to 0° C., then methane sulfonyl chloride (0.36 ml, 4.587 mmol) was slowly added. The ice bath was removed, and stirring continued for another 2 h at room temperature. The reaction mixture was diluted with DCM (75 ml), washed with water (50 ml), 0.5 N HCl (10 ml) and brine solution (20 ml), dried on dry $MgSO_4$ and concentrated. The crude compound was mixed with imidazole (595 mg, 8.737 mmol) and stirred at 75° C. for 16 h. The crude compound was purified by silica gel column (2% MeOH in DCM) to give diethyl 2-(12-(1H-imidazol-1-yl)hexadecyl)malonate (640 mg, 32.5%) as a light brown coloured liquid.

$R_f$=0.63 (5% MeOH in DCM, Iodine and $KMnO_4$ active); $^1H$ NMR (300 MHz, $CDCl_3$) δ 7.44 (s, 1H), 7.04 (s, 1H), 6.86 (s, 1H), 4.19-4.12 (q, 4H), 3.90-3.80 (m, 1H), 3.27 (t, 1H), 1.85-1.83 (m, 2H), 1.73-1.64 (m, 2H), 1.26-1.00 (m, 29H), 0.81 (t, 3H); $^{13}C$ NMR (75 MHz, $CDCl_3$) δ 169.54, 136.40, 129.21, 116.41, 61.17, 58.70, 52.01, 36.27, 35.98, 29.40, 29.32, 29.22, 29.14, 28.68, 28.17, 27.25, 26.02, 22.24, 14.03, 13.82; MS (EI) m/z: [M+1]⁺ (3.2%), [M]⁺ (8.7%), 405 (17.8%), 393 (26.2%), 291 (40.6%), 137 (55.6%), 95 (23.9%), 81 (22.4%), 69 (100%), 68 (42.5%), 55 (44.3%), 41 (40.9%).

(e) Synthesis of 14-(1H-imidazol-1-yl)octadecanoic acid

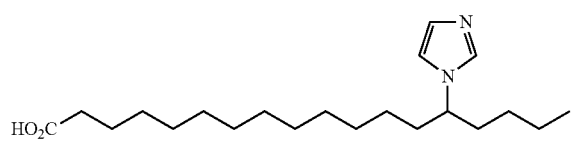 [SMILES: CCCCC(CCCCCCCCCCCCC(=O)O)n1ccnc1]

Diethyl 2-(12-(1H-imidazol-1-yl)hexadecyl)malonate (415 mg, 0.9209 mmol) was dissolved in a 3:1 mixture of methanol (9 ml) and water (3 ml), cooled to 0° C. then NaOH (147 mg, 3.684 mmol) was added and the reaction mixture stirred at room temperature for 3 h. The reaction mixture was then concentrated under reduced pressure to remove MeOH, cooled to 0° C. to 5° C., the pH adjusted to 5, extracted with DCM (3×25 ml), dried on dry MgSO₄, and concentrated under reduced pressure. The crude compound was obtained as a light yellow color liquid. This crude compound was heated at 170° C. to remove one carboxyl acid group from the di-carboxylic acid by the evolution of $CO_2$. The crude product was then purified by silica gel column (3 to 5% of MeOH in DCM) to give 14-(1H-imidazol-1-yl)octadecanoic acid (221 mg, 68%) as a pale yellow gummy liquid.

$R_f$=0.48 (10% MeOH in DCM, Iodine and KMnO₄ active); ¹H NMR (300 MHz, CDCl₃) δ 10.28 (s, 1H), 7.70 (s, 1H), 7.12 (s, 1H), 6.89 (s, 1H), 3.90 (m, 1H), 2.33 (t, 2H), 1.80-1.60 (m, 6H), 1.37-1.00 (m, 23H), 0.85 (t, 3H); ¹³C NMR (151 MHz, CDCl₃) δ 177.76, 136.07, 127.48, 116.65, 59.34, 41.46, 36.20, 36.15, 34.85, 31.78, 29.70, 29.32, 29.29, 29.27, 29.26, 29.17, 29.15, 29.09, 29.06, 29.02, 28.94, 26.03, 25.96, 25.03, 22.61; MS (EI) m/z: [M]⁺ 350 (1.9%), 293 (34.9%), 151 (11.4%), 138 (16.9%), 137 (55.6%), 95 (15.6%), 69 (100%), 55 (31.5%), 43 (22.9%), 41 (30%); HRMS Calculated: 350.2933. Found: 350.29349.

(f) Synthesis of (3414-(1H-imidazol-1-yl)octadecanoyl)oxy)propyl)triphenylphosphonium (TPP-14-ISA)

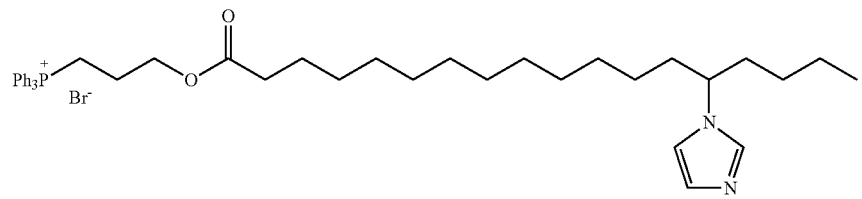

14-(1H-imidazol-1-yl)octadecanoic acid (176 mg, 0.502 mmol) was dissolved in dry DCM (10 ml), cooled to 0° C., then (3-hydroxypropyl)triphenylphosphonium bromide (201 mg, 0.502 mmol), DCC (104 mg, 0.502 mmol) and DMAP (6 mg, 0.05 mmol) were added and the reaction mixture stirred for 16 hours at room temperature. The reaction mixture was filtered to remove the formed DCU and then concentrated. The crude product was dissolved in CHCl₃, filtered and concentrated. The crude product was then purified by silica gel column (4% MeOH in DCM) to give TPP-14-ISA (263 mg, 71%) as a colorless gummy liquid.

$R_f$=0.35 (10% MeOH in DCM, Iodine and KMnO₄ active); ¹H NMR (300 MHz, CDCl₃) δ 7.89-7.66 (m, 15H), 7.49 (s, 1H), 7.06 (s, 1H), 6.90 (s, 1H), 4.36 (t, 2H), 4.05-3.89 (m, 3H), 2.23 (t, 2H), 2.05-1.96 (m, 2H), 1.76-1.66 (m, 4H), 1.55-1.50 (m, 2H), 1.31-1.03 (m, 22H), 0.83 (t, 3H); ¹³C NMR 75 MHz, CDCl₃) δ 173.44, 135.13, 135.10, 133.79, 133.66, 130.61, 130.44, 118.65, 117.51, 63.17, 62.93, 58.87, 36.29, 35.99, 34.15, 29.49, 29.43, 29.37, 29.22, 29.19, 29.09, 28.19, 26.04, 24.82, 22.27, 20.13, 19.43, 13.85; MS (FAB) m/z: [M+1]⁺ 654 (11.7%), 653 (24.1%), 183 (12.1%), 95 (16.5%), 77 (16.5%), 69 (100%), 57 (33.2%), 43 (46%), 41 (51%); HRMS Calculated: 653.4230. Found: 653.42143.

Example 10

Preparation of (3-((10-(1H-imidazol-1-yl)octadecanoyl)oxy)propyl)triphenylphosphonium bromide (TPP-10-ISA)

(a) Synthesis of 10-(benzyloxy)decan-1-ol

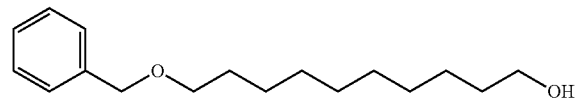 [SMILES: OCCCCCCCCCCOCc1ccccc1]

To a stirred suspension of decane-1,10-diol (3 g, 17.21 mmol), benzyl bromide (2.25 ml, 18.94 mmol) and Ag₂O (5.98 g, 25.82 mmol) in dry DCM (50 ml) were added, the reaction mixture was refluxed overnight, then the Ag₂O was filtered off. The crude product was purified by silica gel column (10% EtOAc in Hexane) to afford 10-(benzyloxy) decan-1-ol as a gummy colorless liquid (2.96 g, 65%).

$R_f$=0.55 (20% EtOAc in Hexane, KMnO₄ active); ¹H NMR 300 MHz, CDCl₃) δ 7.37-7.28 (m, 5H), 4.52 (s, 2H), 3.60 (t, 2H), 3.49 (t, 2H), 2.37 (s, 1H), 1.69-1.51 (m, 4H), 1.37-1.32 (m, 12H); ¹³C NMR (151 MHz, CDCl₃) δ 138.65, 128.42, 128.35, 127.65, 127.49, 126.89, 72.85, 70.52, 62.78, 32.77, 29.76, 29.58, 29.55, 29.47, 26.20, 25.80; MS (EI) m/z: 264 [M]⁺ (6.5%), 108 (24.9%), 107 (65.6%), 92 (37.8%), 91 (100%); HRMS Calculated: 264.2089. Found: 264.2095.

(b) Synthesis of (((10-bromodecyl)oxy)methyl)benzene

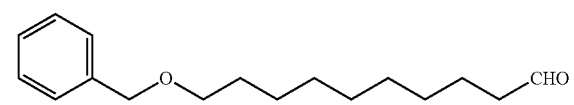 [SMILES: O=CCCCCCCCCCOCc1ccccc1]

10-(benzyloxy)decan-1-ol (8.1 g, 30.64 mmol) was dissolved in dry DCM (150 ml), cooled to 0° C., then PCC (7.86 g, 45.95 mmol) was added, and stirring continued for another 2 h at ambient temperature. The reaction mixture was concentrated and then purified by silica gel column (10% EtOAc in Hexane) to give (((10-bromodecyl)oxy)methyl)benzene as a colorless liquid (6.27 g, 78%).

$R_f$=0.68 (20% EtOAc in Hexane, KMnO₄ active); ¹H NMR 300 MHz, CDCl₃) δ 9.76 (t, 1H), 7.39-7.25 (m, 5H), 4.51 (s, 2H), 3.48 (t, 2H), 2.44-2.39 (m, 2H), 1.67-1.58 (m, 4H), 1.37-1.31 (m, 10H); ¹³C NMR (75 MHz, CDCl₃) δ: 202.83, 138.72, 128.32, 127.59, 127.45, 72.85, 70.47, 43.88, 29.75, 29.38, 29.35, 29.28, 29.13, 26.16, 22.06; MS (EI) m/z: 262 [M]+ (4.1%), 108 (15.8%), 92 (31.5%), 91 (100%), 55 (11.2%); HRMS Calculated: 262.1933. Found: 262.1935.

(c) Synthesis of 18-(benzyloxy)octadecan-9-ol

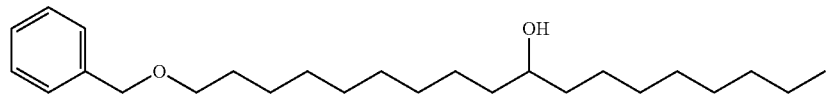 [SMILES: CCCCCCCCC(O)CCCCCCCCCOCc1ccccc1]

To a stirred suspension of Mg metal (0.65 g, 26.83 mmol) and a catalytic amount of Iodine in dry THF (20 ml) at 70° C., 1-bromooctane (3.57 ml, 23.48 mmol) in THF (10 ml) was added dropwise. Stirring was continued for another 30 minutes at this temperature, then the reaction mixture was cooled to room temperature, and was added slowly to a stirred solution of (((10-bromodecyl)oxy)methyl)benzene (4.4 g, 16.77 mmol) in THF (30 ml) at 0° C. The reaction was warmed to room temperature and stirring was continued for another 2 h. The reaction was quenched with ammonium chloride solution, extracted with EtOAc (3×50 ml), the combined organic layers were washed with brine solution, dried over MgSO₄ and concentrated. The crude product was purified by silica gel column (12% EtOAc in Hexane) to give 18-(benzyloxy)octadecan-9-ol as a low melting white colored solid (3.85 g, 61%).

$R_f$=0.45 (20% EtOAc in Hexane, KMnO₄ active); ¹H NMR 300 MHz, CDCl₃) δ 7.37-7.28 (m, 5H), 4.52 (s, 2H), 3.60-3.58 (m, 1H), 3.50-3.46 (t, 2H), 1.68-1.59 (m, 2H), 1.52-1.30 (m, 28H), 0.92-0.88 (m, 3H); ¹³C NMR (75.46 MHz, CDCl₃) δ 138.72, 128.39, 128.33, 127.62, 127.46, 125.9, 72.85, 71.99, 70.52, 37.5, 31.9, 29.77, 29.74, 29.71, 29.61, 29.58, 29.55, 29.48, 29.30, 26.19, 25.67, 22.68, 14.12; MS (EI) m/z: 358 [M−18]+ (2.5%), 107 (25.5%), 92 (19.7%), 91 (100%), 69 (12.8%).

(d) Synthesis of 1-(18-(benzyloxy)octadecan-9-yl)-1H-imidazole

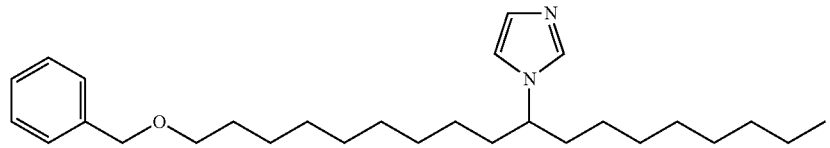 [SMILES: CCCCCCCCC(CCCCCCCCCOCc1ccccc1)n1ccnc1]

18-(benzyloxy)octadecan-9-ol (6 g, 15.93 mmol), DMAP (0.195 g, 1.59 mmol) and TEA (2.9 ml, 20.71 mmol) in dry DCM (90 ml) were cooled to 0° C., then methanesulfonyl chloride (1.64 ml) was added under N₂. The reaction was warmed to room temperature and stirring continued for another 3 h. The reaction mixture was diluted with DCM (100 ml), washed with 1N HCl, water, and brine solution and dried over MgSO₄. The crude compound and imidazole (2.17 g, 31.86 mmol) were then heated at 70° C. for 16 h. The crude product was purified by silica gel column (1.5% MeOH in DCM) to give 1-(18-(benzyloxy)octadecan-9-yl)-1H-imidazole as a gummy liquid (2.22 g, 33%).

$R_f$=0.42 (5% MeOH in DCM, KMnO₄ active); ¹H NMR 300 MHz, CDCl₃) δ 7.41 (s, 1H), 7.29-7.20 (m, 5H), 7.03 (s, 1H), 6.83 (s, 1H), 4.45 (s, 2H), 3.86-3.77 (m, 1H), 3.41 (t, 2H), 1.69-1.52 (m, 6H), 1.30-1.28 (m, 24H), 0.84 (t, 3H); ¹³C NMR (75.46 MHz, CDCl₃) 138.69, 136.43, 129.39, 128.26, 127.5, 127.37, 116.30, 72.78, 70.41, 58.59, 36.28, 31.76, 29.72, 29.38, 29.34, 29.32, 29.29, 29.17, 29.14, 26.12, 26.02, 22.59, 14.07; MS (EI) m/z: 426 [M]+ (0.9%), 270 (5.0%), 203 (10.4%), 193 (13.7%), 105 (28.4%), 92 (10.5%), 91 (100%), 69 (54.3%); HRMS Calculated: 426.3610. Found: 426.36156.

(e) Synthesis of 10-(1H-imidazol-1-yl)octadecan-1-ol 1-(18-(benzyloxy)octadecan-9-yl)-1H-imidazole (1.5 g, 3.52 mmol) was dissolved in EtOH, then 10% Pd on carbon (200 mg) was added and the reaction mixture hydrogenated under hydrogen balloon at reflux for 2 days. The reaction was filtered off to remove Pd carbon, then the filtrate was concentrated. The crude product was purified by silica gel column (3% MeOH in DCM) to give 10-(1H-imidazol-1-yl)octadecan-1-ol as a gummy liquid (0.96 g, 81%).

$R_f$=0.55 (10% MeOH in DCM, KMnO₄ and Iodine active); ¹H NMR (300 MHz, CDCl₃) δ 7.43 (s, 1H), 7.03 (s, 1H), 6.86 (s, 1H), 3.90-3.80 (m, 1H), 3.59 (t, 2H), 3.14 (s, 1H), 1.75-1.61 (m, 4H), 1.56-1.47 (m, 2H), 1.25-1.06 (m, 24H), 0.84 (t, 3H); ¹³C NMR (151 MHz, CDCl₃) δ: 136.38, 129.18, 116.42, 62.50, 58.75, 36.28, 36.24, 32.75, 31.75, 29.31, 29.26, 29.18, 29.13, 29.04, 26.03, 25.94, 25.71, 22.58, 14.05; MS (EI) m/z: 336 [M]+ (4.6%), 306 (7.9%), 223 (23.3%), 221 (14.1%), 194

(14.9%), 193 (66.8%), 123 (11%), 122 (73.9%), 105 (87.6%), 77 (56.7%), 69 (100%), 55 (32.9%); HRMS Calculated: 336.3141. Found: 336.31355.

(f) Synthesis of 10-(1H-imidazol-1-yl)octadecanoic acid

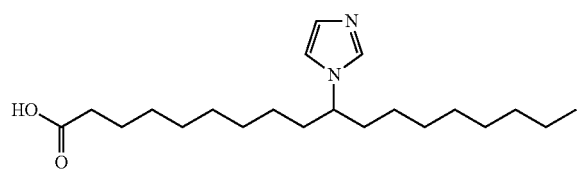 [SMILES: CCCCCCCCC(CCCCCCCCC(=O)O)n1ccnc1]

Jones Reagent Preparation:

1 g of $CrO_3$ was dissolved in concentrated $H_2SO_4$ (1 ml), then diluted with water (3 ml) at 0° C.

10-(1H-imidazol-1-yl)octadecan-1-ol (210 mg, 0.63 mmol) was dissolved in acetone (5 ml) and water (2.5 ml), then Jones reagent (0.75 ml) was added at 0° C. and stirring continued for 3 h at room temperature. The reaction mixture was concentrated and diluted with water (10 ml), and extracted with DCM (3×10 ml), then the combined organic layers were washed with brine solution, dried on $MgSO_4$ and concentrated. The crude compound was purified by silica gel column (3-5% MeOH in DCM) to give 10-(1H-imidazol-1-yl)octadecanoic acid (185 mg, 84%) as a gummy liquid.

$R_f$=0.5 (10% MeOH in DCM, $KMnO_4$ and Iodine active); $^1$H NMR 300 MHz, $CDCl_3$) δ 11.23 (s, 1H), 7.69 (s, 1H), 7.12 (s, 1H), 6.88 (s, 1H), 3.94-3.85 (m, 1H), 2.34-2.29 (m, 2H), 1.78-1.58 (m, 6H), 1.26-1.07 (m, 22H), 0.87 (t, 3H); $^{13}$C NMR (151 MHz, $CDCl_3$) δ: 176.76, 136.07, 127.48, 116.65, 59.34, 41.46, 36.20, 36.15, 34.85, 31.78, 29.70, 29.32, 29.29, 29.27, 29.26, 29.17, 29.15, 29.09, 29.06, 29.02, 28.94, 26.03, 25.96, 25.03, 22.61, 14.09; MS (EI) m/z: 336 [M]$^+$ (2.7%), 238 (12.5%), 237 (67.5%), 194 (18.1%), 193 (100%), 95 (19.8%), 69 (90.4%), 55 (32.6%), 41 (32.7%).

(g) Synthesis of (3-((10-(1H-imidazol-1-yl)octadecanoyl)oxy)propyl)triphenylphosphonium bromide (TPP-10-ISA)

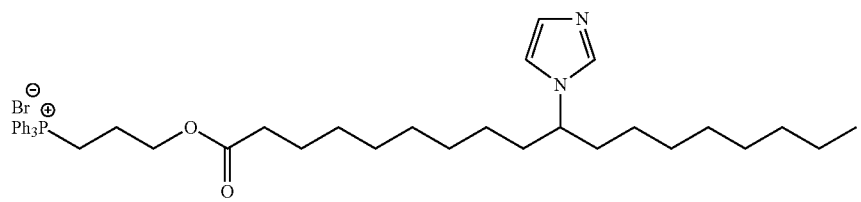

10-(1H-imidazol-1-yl)octadecanoic acid (145 mg, 0.414 mmol) was dissolved in dry DCM (5 ml), cooled to 0° C., then (3-hydroxypropyl)triphenylphosphonium bromide (166 mg, 0.414 mmol), DCC (85 mg, 0.414 mmol) and DMAP (5 mg, 0.04 mmol) were added to it. The reaction mixture was stirred at room temperature for 16 h. The reaction mixture was then filtered off and concentrated under reduced pressure. The crude product was purified by silica gel column (4-5% MeOH in DCM) to give TPP-10-ISA (235 mg, 77%) as a gummy liquid.

$R_f$=0.45 (10% MeOH in DCM, $KMnO_4$ and iodine active); $^1$H NMR (300 MHz, $CDCl_3$) δ 7.89-7.66 (m, 15H), 7.54 (s, 1H), 7.07 (s, 1H), 6.92 (s, 1H), 4.36 (t, 2H), 4.05-3.86 (m, 3H), 2.22 (t, 2H), 2.06-1.94 (m, 2H), 1.73-1.71 (m, 4H), 1.53-1.48 (m, 2H), 1.26-1.03 (m, 22H), 0.85 (t, 3H); $^{13}$C NMR (75 MHz, $CDCl_3$) δ 173.40, 135.15, 135.11, 133.78, 133.64, 130.62, 130.45, 118.62, 117.47, 63.18, 62.95, 58.93, 36.29, 36.24, 34.08, 31.76, 29.32, 29.19, 29.13, 29.04, 29.00, 28.95, 26.04, 25.98, 24.71, 22.58, 22.31, 22.26, 20.11, 19.41, 14.06; MS (EI) m/z 654 (10.7%), 653 (23.2%), 109 (13.3%), 95 (26.5%), 83 (24.9%), 81 (26.1%), 71 (26.4%), 69 (100%), 57 (68%), 55 (84%), 43 (76.8%), 41 (68.6%). HRMS Calculated: 653.4230. Found: 653.42797.

Example 11

Studies of the Effectiveness of TPP-IOA for Protecting Against Cell Death Induced by Oxygen-Glucose Deprivation (OGD)

In this example, the effectiveness of TPP-IOA at improving cell survival following an oxygen-glucose deprivation (OGD) model of ischemic stroke, expected to result in apoptotic cell death, was studied.

For OGD experiments, the human neuronal-like SH-SY5Y cell line was exposed to an 8 hour period of OGD, and then incubated with TPP-IOA upon restoration of normal growth conditions. Viability was assessed using the WST-1 cell proliferation assay after 24 and 48 hours of recovery. TPP-IOA was found to be effective at improving survival after OGD.

(a) Materials and Methods

For the OGD experiments of the present study, neuronal-like SH-SY5Y (human neuroblastoma) cells were subjected to a period of OGD to mimic cerebral ischemia. Following OGD exposure, cells were incubated in the presence of TPP-IOA. Cell viability was then assessed by the WST-1 cell proliferation assay after 24 and 48 hours of recovery.

Reagents and Materials

Dimethylsulfoxide (DMSO), L-glutamine, Roswell Park Memorial Institute (RPMI) 1640 media, and 0.4% Trypan blue solution were purchased from Sigma-Aldrich Canada Ltd (Oakville, ON, Canada). HEPES, L-glutamic acid, and sodium phosphate were purchased from BioShop (Burlington, ON, Canada). High glucose Dulbecco's Modified Eagle Medium (DMEM), fetal bovine serum, isopropanol, non-essential amino acids solution, penicillin/streptomycin solution, potassium phosphate, 0.25% trypsin solution with EDTA, and Triton™ 100× were purchased from Fisher Scientific (Mississauga, ON, Canada; including HyClone). 100 mm diameter, tissue culture-treated, nonpyrogenic, polystyrene, culture plates were purchased from Corning Inc. (Corning, N.Y., USA). Potassium chloride, sodium chloride, and 6-well and 96-well tissue-culture treated, polystyrene, flat bottom culture plates were purchased from VWR (Mississauga, ON, Canada). 2 mL cryogenic vials were purchased from Simport (Beloeil, QC, Canada). TPP-IOA was prepared by a method disclosed in the present application.

Cell lines, Culture Conditions, & Subculturing

The SH-SY5Y (human neuroblastoma; ATCC, Manassas, Va., USA) cell line was used. SH-SY5Y cells were grown in high glucose DMEM supplemented with 10% fetal bovine serum, 4 mM L-glutamine, 584 mg/L glutamate, 25 mM HEPES, phenol red, and 50 I.U./mL penicillin & 50 µg/mL streptomycin solution. The cell line was cultured at 37° C. in a humidified atmosphere containing 5% $CO_2$. SH-SY5Y cells were cultured at atmospheric $O_2$ levels. The cell line was incubated in Thermo Form a Series II water-jacketed $CO_2$ incubators, HEPA Class 100. All cell culture work was performed under sterile conditions inside of a Class II Type A2 biological safety cabinet (Fisher Scientific, Mississauga, ON, Canada & Esco Inc., Hatboro, Pa., USA).

Cells were grown and expanded in culture on 100 mm diameter culture plates. Once approximately 75-80% confluence was reached, cells were subcultured at the following ratio: 1:5 for SH-SY5Y cells. For subculturing, growth medium was removed from the culture plates, and the plates were then rinsed with 1× phosphate-buffered saline buffer (PBS; 137 mM NaCl, 2.7 mM KCl, 10 mM $Na_2HPO_4$, 2 mM $KH_2PO_4$, pH 7.4). Cells were then incubated with 0.25% Trypsin/EDTA solution at 37° C. for 5 minutes to detach them from the plates. Once cells were visibly detached, growth media was added to stop trypsin action. Cell suspensions were then collected into conical tubes, and centrifuged for 5 minutes at 250 g. The resulting supernatant was discarded, and the cell pellet was resuspended with growth media (1 mL per new plate). 1 mL of the resulting cell suspension was added to throughout the growth surface of each new culture plate containing fresh growth media. Growth media was refreshed every two days when necessary.

For all cell culture work, any buffers, solutions, or media used were pre-warmed at 37° C. in an Isotemp 110 water bath (Fisher Scientific, Mississauga, ON, Canada) for at least 30 minutes prior to use.

For all experiments, cell densities for seeding onto culture plates were determined by trypan blue exclusion (see below for protocol).

TPP-IOA Stock Solutions & Treatment Conditions

TPP-IOA was stored in a −20° C. freezer throughout the duration of the present study. 1000× stock solutions of TPP-IOA dissolved in sterile DMSO were made in the following manner: TPP-IOA was first obtained using a microspatula (VWR, Mississauga, ON, Canada) and weighed out in a microcentrifuge tube. Once the correct mass was obtained, TPP-IOA was thoroughly dissolved in sterile DMSO by resuspending using a micropipette, and the resulting solution was filtered through a Fisherbrand syringe filter containing a 0.2 µm pore size nylon membrane (Fisher Scientific, Mississauga, ON, Canada). Different concentrations of TPP-IOA stock solutions were then made by a set of serial dilutions into sterile microcentrifuge tubes. All TPP-IOA stock solutions were stored at −20° C.

Cell cultures were treated with the indicated TPP-IOA concentrations by incubation with TPP-IOA in the surrounding growth media. To help ensure that TPP-IOA was not concentrated in one particular area of the culture plates, TPP-IOA was added to media inside of conical tubes, then briefly vortexed, followed by the careful addition to culture plates. For all concentrations of TPP-IOA treatments used, the final percentage of DMSO in the media was 0.1%. Control groups (0 µM TPP-IOA) received equivalent volumes of sterile DMSO.

Oxygen Glucose Deprivation Experiments

SH-SY5Y cells were harvested from 100 mm diameter culture plates once 70-80% confluence was reached, and were then seeded on 96-well plates at a density of $3.0 \times 10^4$ cells per well in normal growth media. The cells were then incubated overnight (approximately 16 hours) under normal growth conditions to allow for attachment to plates. During this time, DMEM (supplemented with 25 mM HEPES, 4 mM L-glutamine, and 584 mg/L glutamate) with no glucose or serum to be used for OGD was incubated on a culture plate in the 3% oxygen, 5% carbon dioxide, 37° C. incubator to reduce the oxygen levels within the media. In the following morning, this plate of media was placed inside of a custom-built anoxic chamber that was continuously pumped with 95% nitrogen-5% carbon dioxide gas mixture from Praxair Canada (St. Catharines, ON, Canada) to further reduce/eliminate the amount of oxygen present in the media. 0.2% oxygen level within the chamber was reached within approximately 10 minutes, and the plate of media was incubated for 30 minutes under these conditions. After this period, the growth media on the 96-well plates of SH-SY5Y cells was removed, and carefully replaced with the de-oxygenated DMEM containing no glucose or serum. The plates of cells were then incubated in the anoxia chamber at 0.2% oxygen for 8 hours, continuously pumped with the 95% nitrogen-5% carbon dioxide gas mixture. An oxygen sensor was kept inside of the chamber, and the 0.2% oxygen level was monitored and maintained by a Roxy-1 universal regulator/controller (Sable Systems Int., Las Vegas, Nev., USA). Throughout the duration of the media de-oxygenation and OGD, the anoxic chamber was kept inside of a 37° C. Isotemp incubator (Fisher Scientific, Mississauga, ON, Canada). The lid of the chamber was also tightly sealed with tape for the duration of the experiment. A small hole present at the back of the chamber to allow for the oxygen to be released was sealed off with tape once the 0.2% oxygen level was reached, which took approximately ten minutes.

After the 8 hour period of OGD, the glucose/serum-free DMEM was carefully removed from the wells, and replaced with normal growth media containing TPP-IOA. The cells were incubated at their normal growth conditions, and viability was assessed after 24 and 48 hours of recovery with the use of the WST-1 cell proliferation assay.

Measures of Viability

Cell Counting Using Trypan Blue Exclusion:

All cell counts done to determine cell density for seeding were performed using the trypan blue exclusion method. For all measurements, a 20 µL sample was taken from each cell suspension desired to be counted. 2.5 µL of this sample cell suspension was then diluted with 47.5 µL of 0.4% trypan blue solution, resulting in a dilution factor of 20. This solution was carefully mixed and allowed to incubate for 3 minutes at room temperature. Following incubation, the mixture was briefly resuspended, and 10 µL was loaded on a hemacytometer with a cover slip in place. The hemacytometer was then viewed by a Hund Wetzlar Wilovert A Inverted microscope (Fisher Scientific, Mississauga, ON, Canada), and the number of cells in the four large corner squares and large middle square were counted. Cells appearing colourless/opaque were recorded as living, while cells appearing blue were recorded as non-viable. The number of cells per mL was calculated by the following equation:

$$\text{Cells/mL} = \text{average number of cells per square} \times \text{dilution factor} \times 10000.$$

To determine the total cell number, the amount of cells per mL was multiplied by the total volume of the cell suspension.

WST-1 Cell Proliferation Assay:

The Premixed WST-1 Cell Proliferation Reagent from Clontech Laboratories, Inc. (Mountain View, Calif., USA) was used to assess the viability of oxygen/glucose-deprived SH-SY5Y cells after 24 and 48 hours recovery. This assay is based on the cleavage of the water-soluble tetrazolium salt WST-1 by mitochondrial dehydrogenases, which are active in viable cells, to formazan dye (Scheme 2; Clontech Laboratories, Inc.). Manufacturer's protocols were followed.

Scheme 2 shows the cleavage of the tetrazolium salt WST-1 to formazan by mitochondrial succinate dehydrogenase. Activity of this enzyme increases proportionally with the number of viable cells. This leads to an increased production of formazan dye conversion from WST-1. The amount of formazan dye produced is quantified by absorbance at 420-480 nm. (EC=electron coupling reagent, RS=mitochondrial succinate-tetrazolium reductase system). Adapted from Clontech Laboratories, Inc.[45].

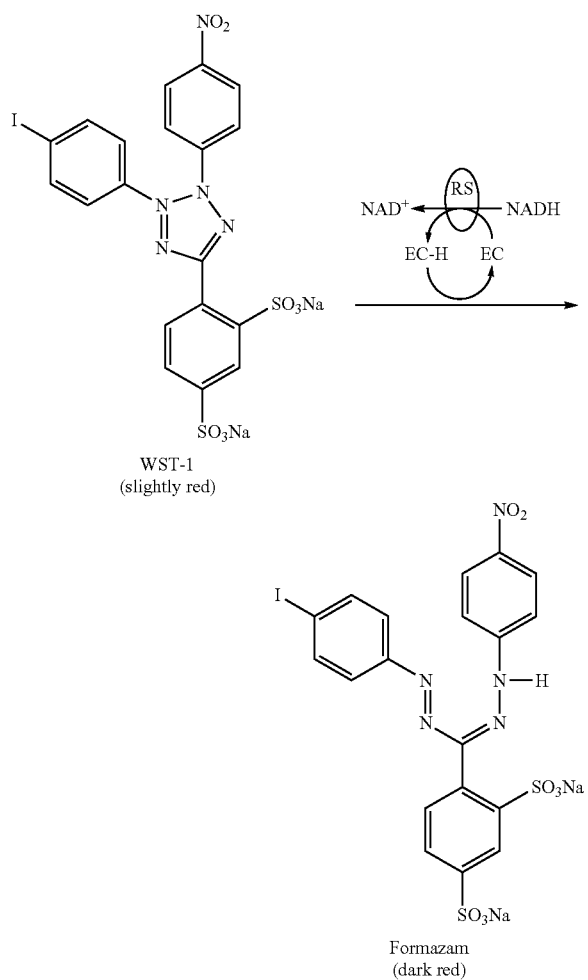

Scheme 2

WST-1
(slightly red)

Formazam
(dark red)

For measurements, premixed WST-1 cell proliferation reagent was added to the wells of cells (ratio of 1:10 with growth media) cultured on 96-well flat bottomed plates. A background control of growth media with no cells was used for each time point and TPP-IOA treatment. The plate was shaken for 1 minute on a plate shaker (Vortex-Genie 2, Scientific Industries), and then incubated in the proper growth incubator. SH-SY5Y cells were incubated for 4 hours. The plate was then shaken thoroughly for 1 minute on a plate shaker, and then absorbance at 450 nm, with a reference wavelength of 650 nm, was measured using a microplate reader (BioTek, Winooski, Vt., USA).

For data analysis, the background control and reference wavelength absorbance readings were subtracted from the 450 nm reading for each sample. The average absorbance reading for the 0 µM TPP-IOA treatment was then set equal to 1, and all sample readings were divided by the mean absorbance of the 0 µM TPP-IOA treatment to obtain a measure of fold change in viability compared to the control.

A preliminary experiment to ensure that experimental absorbance measures were within a linear range for each cell line was not performed.

Statistical Analysis

All data were analyzed using a two-tailed, unequal variance Student's t-test in Microsoft Excel™ 2010. $\alpha=0.05$ was used to determine statistical significance. Standard error of the mean (SEM) was calculated by dividing the standard deviation of the data sets by the square root of the number of samples in the data sets.

(b) Results

The human neuronal-like cell line SH-SY5Y was used to assess the effectiveness of TPP-IOA at protecting against cell death that occurs following a period of OGD, which is an in vitro model of cerebral ischemia. Once an experimental system for the OGD experiments was developed, an initial experiment was performed whereby SH-SY5Y cells were exposed to a 16-hour period of OGD (data not included herein). Trypan blue exclusion measurements of cell viability were made immediately after the OGD period, before TPP-IOA treatment, however a virtually undetectable amount of cells were present. From then on, the duration of OGD was adjusted to be 8 hours. This was intended for there to still be a sufficient amount of viable cells present immediately after OGD so that possible protection by TPP-IOA against apoptotic cell death induced following OGD could be better assessed. Survival after 24 and 48 hours of recovery compared to control samples was assessed using the WST-1 cell proliferation assay.

Significant improvements in viability were observed at 24 hours of recovery in cells incubated in the presence of 2.5 µM and 5 µM TPP-IOA (FIG. 13). With 2.5 µM TPP-IOA treatment, a 1.192±0.058-fold change in viability compared to control cells that did not receive TPP-IOA treatment was observed (p=0.017). In cells that were incubated in the presence of 5 µM TPP-IOA, a 1.356±0.074-fold change in viability was observed (p=0.0094). Increased viability was also observed in the 10 µM treatment group, which exhibited a 1.179±0.038-fold change, however, this was non-significant (p=0.0955). After 48 hours of incubation with TPP-IOA, no significant improvements in viability appeared to have been present (all p>0.005).

(c) Discussion

Cell death occurs in response to cerebral ischemia, or stroke. Although the core area of brain tissue affected by cerebral ischemia dies primarily through necrosis during the ischemic event, a large border region of brain tissue surrounding the core area, termed the penumbra, undergoes apoptotic cell death in the following days and hours[16]. With this in mind, some sort of post-stroke therapy aimed at preventing apoptosis may be able to prevent or reduce neural cell death in this region, thus limiting the infarct volume[16]. The present study has demonstrated that anti-apoptotic TPP-IOA was effectively able to reduce cell death in a neuronal-like cell line following a period of OGD, which is an in vitro model of cerebral ischemia. This suggests that this strategy of inhibiting the peroxidase activity of cyt c during mitochondria-mediated apoptosis, and thus suppressing the release of cyt c from the mitochondria, was an effective approach at reducing cell death following OGD.

The current study was done with a commercially available, cancerous neuronal-like cell line, whereby a relatively lengthy duration of OGD was required to induce a sufficient amount of cell death. In some other previous studies that have used this cell line in the context of OGD, long transient periods of OGD (i.e. upwards of 16 hours) have typically been required to induce cell death (e.g. Wang et al., 2002[24]; Fordel et al., 2007[23]; & Serra-Perez et al., 2007[25]). In the current study, a 16 hour period of OGD was found to be too potent. While not wishing to be limited by theory, this was perhaps due to a more efficient experimental setup. An 8 hour period of OGD was then chosen, and protection against cell death was observed with TPP-IOA treatment.

While not wishing to be limited by theory, although the apparent protection of TPP-IOA against cell death that was observed at 24 hours of recovery disappeared at 48 hours, it is possible that the experimental conditions of the present study could be responsible for this observation. Cells were cultured in 96-well plates, with each well containing 100 μL of growth media that was not refreshed during the duration of recovery. The small volume of growth media used may have presented limitations in the metabolic fuel/energy supply for the cells beyond 24 hours. This is important because apoptosis is an energy-dependent process, and ATP depletion is known to cause a shift from apoptotic cell death to necrotic cell death[46]. A larger volume of growth media or a refreshment of growth media after 24 hours is utilized to potentially avoid this possible confounding factor. A measurement that quantifies cell death, such as the assay of released LDH, is used in conjunction with this WST-1 assay to characterize cell survival.

The findings in the current study may have potential implications for clinical stroke. Mitochondria-mediated pathways contribute to the activation of apoptotic cell death following this pathological event, and pro-apoptotic proteins, including cyt c, have been found to be released from mitochondria after cerebral ischemia.[20] Therefore, post-stroke treatment with mitochondrial-targeted TPP-IOA, aimed at inhibiting the peroxidase activity of cyt c and suppressing the release of cyt c, might be an effective approach to prevent neural cell death in the penumbra region.

(d) Conclusions

An experimental setup for an OGD model of transient cerebral ischemia was successfully developed and implemented in the present study. This system can be utilized extensively to perform a variety of future studies in the context of OGD. When this OGD model was used in the present study, it was found that TPP-IOA was effective at reducing cell death in a neuronal-like cell line following a period of OGD. This finding has implications for TPP-IFAs as a possible post-stroke treatment in a clinical setting to limit neural cell death.

Further studies using an OGD model that represents stroke, in terms of both cell type and duration of ischemia are performed, with the ultimate goal being to further test the effectiveness of TPP-IFAs at reducing cell death following an in vivo model of stroke. For further OGD experiments, both the presence of apoptotic markers and measurements of cell death in the following hours and days are examined to determine the effectiveness of TPP-IFAs. For example, the current experiment is repeated using differentiated SH-SY5Y cells. Differentiation of this cell line can be accomplished through the sequential exposure of these cells to retinoic acid and brain-derived neurotrophic factor in serum-free media, which gives rise to a homogeneous population of differentiated human neuronal cells that display similar characteristics to primary cultures of neurons[47]. Beyond this cell type, OGD experiments are also performed on cultured neural cells/tissues from rodents that are particularly sensitive to impairments induced by stroke. The hippocampus is one part of the brain that commonly shows impairment following stroke in rodents and humans[48] and cultures of hippocampal slices are commonly used for ex vivo studies of brain pathophysiology.[49] Hippocampal slices have been used in many OGD studies,[49] and would be an appropriate model. Beyond these OGD experiments, the effectiveness of TPP-IFAs at reducing apoptotic cell death in vivo following stroke are studied using rodent models. The most frequently used model to mimic cerebral ischemia/stroke in rodents is the middle coronary artery occlusion (MCAO) method.[50] TPP-IFAs are administered to the animals after a period of transient MCAO, and measures of apoptotic markers and infarct size are evaluated in brain tissue to determine the effectiveness of TPP-IFAs. Also, behavioral deficits are typically observed following MCAO and stroke,[50] and the effectiveness of TPP-IFAs at ameliorating these are evaluated through a variety of behavioral assessment tests.

Example 12

Further Positional Isomers of IFAs

The synthesis of further positional isomers (described above in Examples 6-10) was performed to probe the effect of changing the location of the imidazole on the acyl chain for TPP compounds.

The racemic structures TPP-6-imidazole-stearic acid, TPP-8-imidazole-stearic acid and TPP-10-imidazole-stearic acid were prepared and their activity compared with TPP-ISA (TPP-12-imidazole-stearic acid).

The binding and behavior of these compounds with partially unfolded cyt c has also been modeled and assessed. Compounds TPP-6-imidazole-stearic acid and TPP-8-imidazole-stearic acid have been tested in vitro and shown to be significantly better inhibitors of cyt c peroxidase than TPP-ISA (TPP-12-imidazole-stearic acid) at a ratio of compound to cyt c of 2.5:1 (FIG. 14A). The effect of TPP-10-imidazole stearic acid on peroxidase activity of cyt c/TOCL complexes has also been assessed (FIG. 14B).

Methods have also been devised for analogues in which the imidazole group is closer to the terminus of the alkyl chain (C-13 and C-14). In general this relies on the mono-bromination of dodecane-1,12-diol, followed by the manipulation of the terminal functional groups to make a long chain secondary alcohol that can be substituted with imidazole. The final materials so produced (13- and 14-substituted imidazole fatty acids) are then esterified with (3-hydroxypropyl)triphenylphosphonium bromide to give the appropriate TPP-13-ISA and TPP-14-ISA. Approaches to imidazole substitution at C-13 and C-14 of stearic acid are shown in FIG. 12.

The compounds TPP-13-imidazole-stearic acid (TPP-13-ISA; Example 8) and TPP-14-imidazole-stearic acid (TPP-14-ISA; Example 9) have been synthesized. The effect of TPP-13-imidazole-stearic acid on peroxidase activity of cyt c/TOCL complexes has also been assessed via $H_2O_2$-dependent oxidation of Amplex Red (FIG. 14A).

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE APPLICATION

[1] Paris, F. et al. Endothelial apoptosis as the primary lesion initiating intestinal radiation damage in mice. *Science* 293, 293-297 (2001).

[2] Merritt, A. J. et al. The role of p53 in spontaneous and radiation-induced apoptosis in the gastrointestinal tract of normal and p53-deficient mice. *Cancer Res.* 54, 614-617 (1994).

[3] Komarova, E. A. et al. Dual effect of p53 on radiation sensitivity in vivo: p53 promotes hematopoietic injury, but protects from gastro-intestinal syndrome in mice. *Oncogene* 23, 3265-3271 (2004).

[4] Ott, M., Gogvadze, V., Orrenius, S. & Zhivotovsky, B. Mitochondria, oxidative stress and cell death. *Apoptosis* 12, 913-922 (2007).

[5] Giorgio, M., Trinei, M., Migliaccio, E. & Pelicci, P. G. Hydrogen peroxide: a metabolic by-product or a common mediator of ageing signals? *Nat. Rev. Mol. Cell. Biol.* 8, 722-728 (2007).

[6] Weiss, J. F. & Landauer, M. R. Protection against ionizing radiation by antioxidant nutrients and phytochemicals. *Toxicology* 189, 1-20 (2003).

[7] Dziegielewski, J. et al. WR-1065, the active metabolite of amifostine, mitigates radiation-induced delayed genomic instability. *Free Radic. Biol. Med.* 45, 1674-1681 (2008).

[8] Dorr, R. T. Radioprotectants: pharmacology and clinical applications of amifostine. *Semin. Radiat. Oncol.* 8, 10-13 (1998).

[9] Belikova, N. A. et al. Peroxidase activity and structural transitions of cytochrome c bound to cardiolipin-containing membranes. *Biochemistry* 45, 4998-5009 (2006).

[10] Krebs, J. J., Hauser, H. & Carafoli, E. Asymmetric distribution of phospholipids in the inner membrane of beef heart mitochondria. *J. Biol. Chem.* 254, 5308-5316 (1979).

[11] Liu, J. et al. Phospholipid scramblase 3 controls mitochondrial structure, function, and apoptotic response. *Mol. Cancer. Res.* 1, 892-902 (2003).

[12] Schlattner, U. et al. Mitochondrial kinases and their molecular interaction with cardiolipin. *Biochim. Biophys. Acta* 1788, 2032-2047 (2009).

[13] Sorice, M. et al. Cardiolipin and its metabolites move from mitochondria to other cellular membranes during death receptor-mediated apoptosis. *Cell. Death Differ.* 11, 1133-1145 (2004).

[14] Tyurina, Y. Y. et al. Oxidative lipidomics of hyperoxic acute lung injury: mass spectrometric characterization of cardiolipin and phosphatidylserine peroxidation. *Am. J. Physiol. Lung Cell. Mol. Physiol.* 299, L73-L85 (2010).

[15] Hanai, A., Yang, W. L., & Ravikumar, T. S. Induction of apoptosis in human colon carcinoma cells HT29 by sublethal cryo-injury: mediation by cytochrome c release International Journal of Cancer, 93(4), 526-533 (2001).

[16] Broughton B R, Reutens D C, Sobey C G. Apoptotic mechanisms after cerebral ischemia. *Stroke.* 2009 May; 40 (5):e331-9. PubMed PMID:19182083.

[17] Eltzschig H K, Eckle T. Ischemia and reperfusion—from mechanism to translation. *Nat. Med.* 2011 Nov. 7; 17 (11): 1391-401. PubMed PMID:22064429.

[18] Lopez-Neblina F, Toledo A H, Toledo-Pereyra LH. Molecular biology of apoptosis in ischemia and reperfusion. J Invest Surg. 2005 November-December; 18 (6): 335-50. PubMed PMID:16319055.

[19] Kroemer G, Galluzzi L, Brenner C. Mitochondrial membrane permeabilization in cell death. Physiol Rev. 2007 January; 87 (1):99-163. PubMed PMID:17237344.

[20] Niizuma K, Yoshioka H, Chen H, Kim G S, Jung J E, Katsu M, Okami N, Chan P H. Mitochondrial and apoptotic neuronal death signaling pathways in cerebral ischemia. Biochim Biophys Acta. 2010 January; 1802 (1):92-9. PubMed PMID:19751828; PubMed Central PMCID: PMC2790539.

[21] Yin X M, Luo Y, Cao G, Bai L, Pei W, Kuharsky D K, Chen J. Bid-mediated mitochondrial pathway is critical to ischemic neuronal apoptosis and focal cerebral ischemia. J Biol. Chem. 2002 Nov. 1; 277 (44):42074-81. PubMed PMID:12200426.

[22] Goldberg M P, Choi D W. Combined oxygen and glucose deprivation in cortical cell culture: calcium-dependent and calcium-independent mechanisms of neuronal injury. J. Neurosci. 1993 August; 13 (8):3510-24. PubMed PMID: 8101871.

[23] Fordel E, Thijs L, Martinet W, Schrijvers D, Moens L, Dewilde S. Anoxia or oxygen and glucose deprivation in SH-SY5Y cells: a step closer to the unraveling of neuroglobin and cytoglobin functions. Gene. 2007 Aug. 15; 398 (1-2):114-22. PubMed PMID:17532579.

[24] Wang C, Nguyen H N, Maguire J L, Perry D C. Role of intracellular calcium stores in cell death from oxygen-glucose deprivation in a neuronal cell line. J Cereb Blood Flow Metab. 2002 February; 22 (2):206-14. PubMed PMID:11823718.

[25] Serra-Pérez A, Verdaguer E, Planas A M, Santalucia T. Glucose promotes caspase-dependent delayed cell death after a transient episode of oxygen and glucose deprivation in SH-SY5Y cells. J. Neurochem. 2008 August; 106 (3): 1237-47. PubMed PMID:18466326.

[26] Agudo-López A, Miguel B G, Fernández I, Martínez A M. Involvement of mitochondria on neuroprotective effect of sphingosine-1-phosphate in cell death in an in vitro model of brain ischemia. Neurosci Lett. 2010 Feb. 12; 470 (2): 130-3. PubMed PMID:20045720.

[27] Kagan, V. E. et al. Cytochrome c acts as a cardiolipin oxygenase required for release of proapoptotic factors. *Nat. Chem. Biol.* 1, 223-232 (2005).

[28] Ross, M. F. et al. Lipophilic Triphenylphosphonium Cations as Tools in Mitochondrial Bioenergetics and Free Radical Biology. *Biochemistry (Moscow)*, 70, 222-230 (2005).

[29] Tang, Z. L. et al. Roles for metallothionein and zinc in mediating the protective effects of nitric oxide on lipopolysaccharide-induced apoptosis. *Mol. Cell. Biochem.* 234/235, 211-217 (2002).

[30] Tyurin, V. A., Tyurina, Y. Y., Kochanek, P. M., Hamilton, R., DeKosky, S. T., Greenberger, J. S., Bayir, H., & Kagan, V. E. Oxidative lipidomics of programmed cell death, *Methods Enzymol.* 442, 375-393 (2008).

[31] Malavolta, M., Bocci, F., Boselli, E. & Frega, N. G. Normal phase liquid chromatography-electrospray ionization tandem mass spectrometry analysis of phospholipids molecular species in blood mononuclear cells: application to cyctic fibrosis. *J. Chromatogr. B* 810, 173-176 (2004).

[32] Qian, S. Y. et al. Identification of protein-derived tyrosyl radical in the reaction of cytochrome c and hydrogen peroxide: characterization by ESR spin-trapping, HPLC and MS. *Biochem. J.* 363, 281-288 (2002).

33 Kon, H. Paramagnetic resonance study of Nitric Oxide hemoglobin. *J. Biol. Chem.* 243, 4350-4357 (1968).
34 Gadsby, P. M., Peterson, J., Foote, N., Greenwood, C. & Thomson, A. J. Identification of the ligand-exchange process in the alkaline transition of horse heart cytochrome c. *Biochem. J.* 246, 43-54 (1987).
35 Brautigan, D. L. et al. Multiple low spin forms of the cytochrome c ferrihemochrome. EPR spectra of various eukaryotic and prokaryotic cytochromes c. *J. Biol. Chem.* 252, 574-582 (1977).
36 Carraway, A. D., Miller, G. T., Pearce, L. L. & Peterson, J. The Alkaline Transition of Bis(N-acetylated) Heme Undecapeptide. *Inorg. Chem.* 37, 4654-4661 (1998).
37 Folch, J., Lees, M., & Sloane Stanley G. H. A simple method for the isolation and purification of total lipides from animal tissues, *J. Biol. Chem.* 226, 497-509 (1957).
38 Liu, X., Kim, C. N., Yang, J., Jemmerson, R. & Wang, X. Induction of apoptotic program in cell-free extracts: requirement for dATP and cytochrome c. *Cell* 86, 147-157 (1996).
39 Murphy, M. P. & Smith, R. A. Targeting antioxidants to mitochondria by conjugation to lipophilic cations. *Annu. Rev. Pharmacol. Toxicol.* 47, 629-656 (2007).
40 Du, C. et al. Mitochondrial ROS and radiation induced transformation in mouse embryonic fibroblasts. *Cancer Biol. Ther.* 8, 1962-1971 (2009).
41 Zhang, Y. et al. Loss of manganese superoxide dismutase leads to abnormal growth and signal transduction in mouse embryonic fibroblasts. *Free Radic. Biol. Med.* 49, 1255-1262 (2010).
42 Duprez, L., Wirawan, E., Vanden Berghe, T. & Vandenabeele, P. Major cell death pathways at a glance. *Microbes Infect.* 11, 1050-1062 (2009).
43 Nagley, P., Higgins, G. C., Atkin, J. D. & Beart, P. M. Multifaceted deaths orchestrated by mitochondria in neurones. *Biochim. Biophys. Acta.* 1802, 167-185 (2010).
44 Porteous, C. M. et al. Rapid uptake of lipophilic triphenylphosphonium cations by mitochondria in vivo following intravenous injection: implications for mitochondria-specific therapies and probes. *Biochim. Biophys. Acta.* 1800, 1009-1017 (2010).
45 Clontech Laboratories, Inc. 2007. Premixed WST-1 Cell Proliferation Reagent User Manual.
46 Eguchi Y, Shimizu S, Tsujimoto Y. Intracellular ATP levels determine cell death fate by apoptosis or necrosis. Cancer Res. 1997 May 15; 57 (10):1835-40. PubMed PMID: 9157970.
47 Encinas M, Iglesias M, Liu Y, Wang H, Muhaisen A, Ceña V, Gallego C, Comella J X. Sequential treatment of SH-SY5Y cells with retinoic acid and brain-derived neurotrophic factor gives rise to fully differentiated, neurotrophic factor-dependent, human neuron-like cells. J. Neurochem. 2000 September; 75 (3):991-1003. PubMed PMID:10936180.
48 Abe K, Aoki M, Kawagoe J, Yoshida T, Hattori A, Kogure K, Itoyama Y. Ischemic delayed neuronal death A mitochondrial hypothesis. Stroke. 1995 August; 26 (8):1478-89. PubMed PMID:7631357.
49 Cho S, Wood A, Bowlby MR. Brain slices as models for neurodegenerative disease and screening platforms to identify novel therapeutics. Curr Neuropharmacol. 2007 March; 5 (1):19-33. PubMed PMID:18615151; PubMed Central PMCID: PMC2435340.
50 Chiang T, Messing R O, Chou W H. Mouse model of middle cerebral artery occlusion. J V is Exp. 2011 Feb. 13; PubMed PMID:21372780; PubMed Central PMCID: PMC3197421.

TABLE 1

| Treatment Group | Overall Survival (52 days) | | Survival Over First 20 Days | | N |
|---|---|---|---|---|---|
| | Median Survival (95% Confidence Interval) | p* | Median Survival (95% Confidence Interval) | p* | |
| 9.25Gy | 13 (11, 14) | | 13 (11, 14) | | 22 |
| TPP-IOA 5 mg/kg body weight, 1 hr before 9.25Gy | —(12, —) | 0.0230 | —(12, —) | 0.0230 | 10 |
| TPP-IOA 5 mg/kg body weight, 10 min before 9.25Gy | —(18, —) | 0.0009 | —(18, —) | 0.0009 | 10 |
| TPP-IOA 5 mg/kg body weight, 10 min after 9.25Gy | —(—, —) | <0.0001 0.4567† | —(—, —) | <0.0001 | 23 |
| TPP-IOA 5 mg/kg body weight, 5 hr after 9.25Gy | —(17, —) | 0.0030 | —(17, —) | 0.0030 | 10 |
| TPP-IOA 5 mg/kg body weight, 24 hr after 9.25Gy | 18 (13, —) | 0.0416 | 18 (13, —) | 0.0416 | 10 |
| TPP-IOA 2.5 mg/kg body weight, 10 min after 9.25 Gy | 17 (14, —) | 0.0525 | 17 (14, —) | 0.0525 | 10 |
| TPP-ISA 5.0 mg/kg body weight 10 min after 9.25 Gy | —(13, —) | 0.0114 | —(13, —) | 0.0114 | 22 |

The two-sided log-rank test was used to examine the differences between irradiated mice with or without treatment with TPP-ISA or TPP-IOA.
Mice were irradiated to 9.25 Gy using a Varian TrueBeam linear accelerator (Varian Medical Systems) and injected i.p. with either TPP-ISA or TPP-IOA (2.5 or 5 mg per kg body weight in 100 μl of water containing 25% ethanol) at 1 h or 10 min before irradiation or 10 min, 5 or 24 h after irradiation.
*TPP-IOA and TPP-ISA versus irradiated mice.
†TPP-IOA (5 mg per kg body weight 10 min after irradiation) versus TPP-ISA (5 mg per kg body weight 10 min after irradiation).

The invention claimed is:
1. A compound of Formula I:

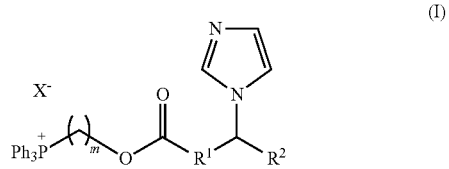

(I)

wherein:

m is 1, 2, 3, 4, 5, or 6;

$R^1$ and $R^2$ are independently selected from $C_{1-20}$alkylene and $C_{2-20}$alkenylene, provided that $R^1$ and $R^2$, together, comprise at least 10 carbon atoms; and X is a counteranion, or a stereoisomer or a solvate thereof.

2. The compound of claim 1, wherein m is 2, 3 or 4.

3. The compound of claim 2, wherein m is 3.

4. The compound of claim 1, wherein $R^1$ and $R^2$ are independently selected from $C_{4-15}$alkylene and $C_{4-15}$alkenylene, provided that $R^1$ and $R^2$, together, comprise at least 12 carbon atoms.

5. The compound of claim 1, wherein $R^1$ is selected from $C_{4-15}$alkylene and $C_{4-15}$ alkenylene and $R^2$ is selected from $C_{4-15}$alkylene.

6. The compound of claim 5, wherein when $R^1$ or $R^2$ is alkenylene, it contains 1 or 2 double bonds.

7. The compound of claim 1, wherein the group, —$R^1$—C-(imidazole)-$R^2$ contains 17 carbons in the longest contiguous carbon chain.

8. The compound of claim 1, wherein the longest contiguous carbon chain is unbranched.

9. The compound of claim 1, wherein X is chloride or bromide.

10. The compound of claim 1, selected from:

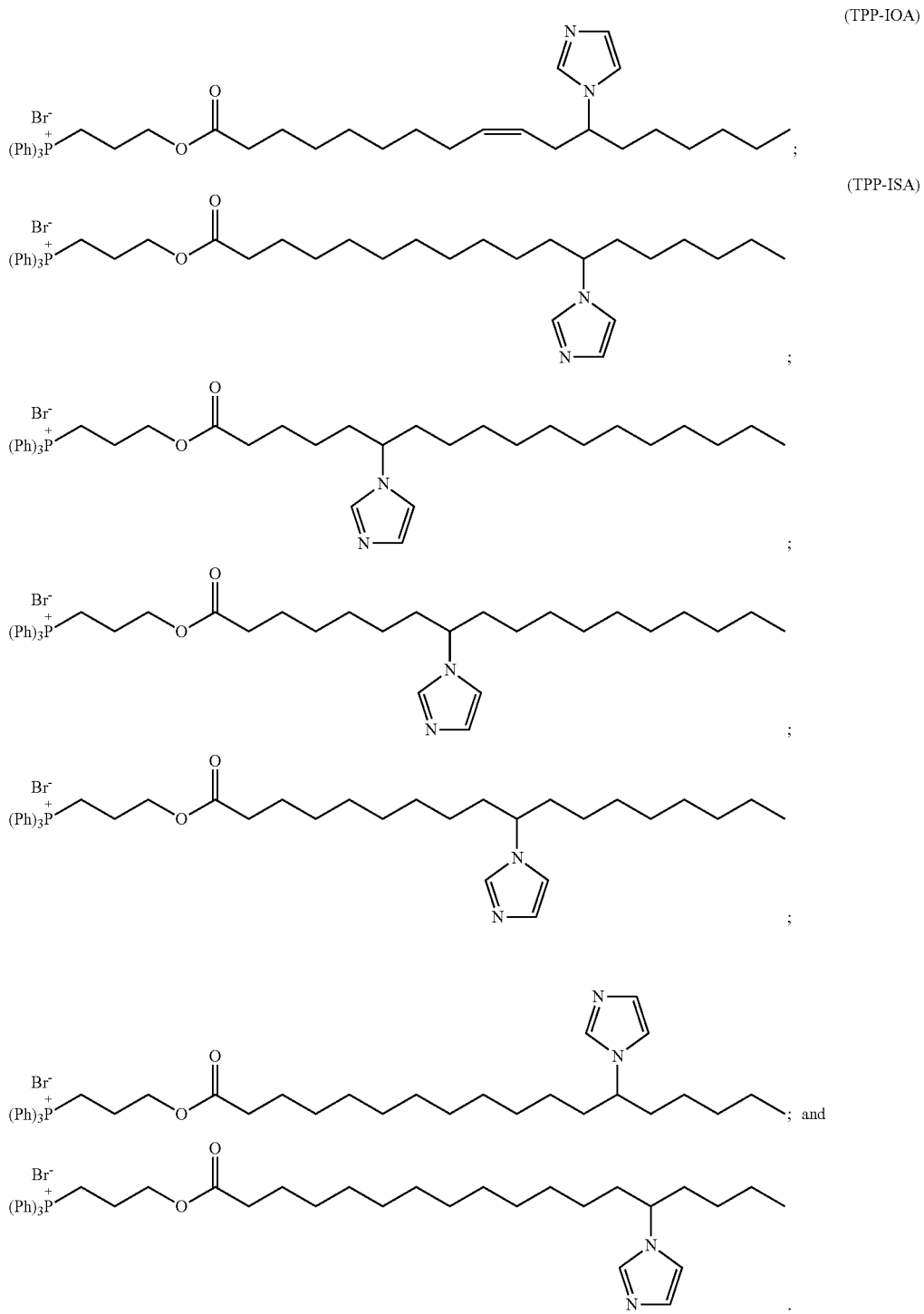

11. The compound of claim 10, selected from:

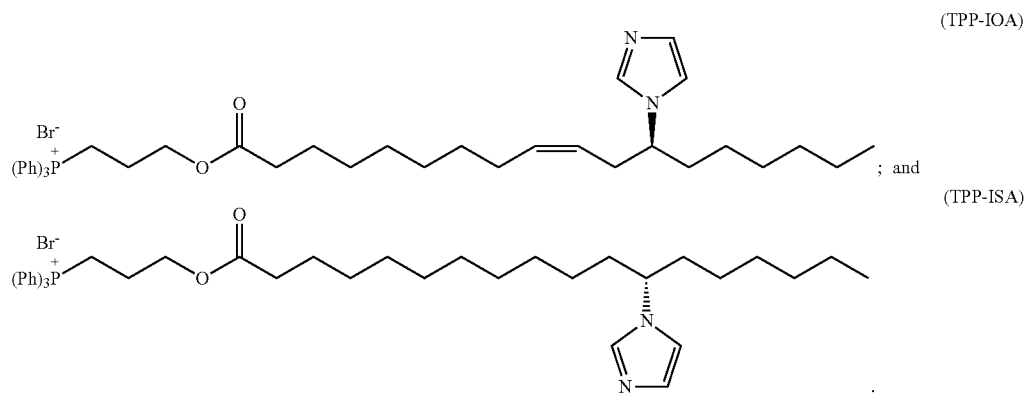

(TPP-IOA); and (TPP-ISA)

12. The compound of claim 10, selected from:

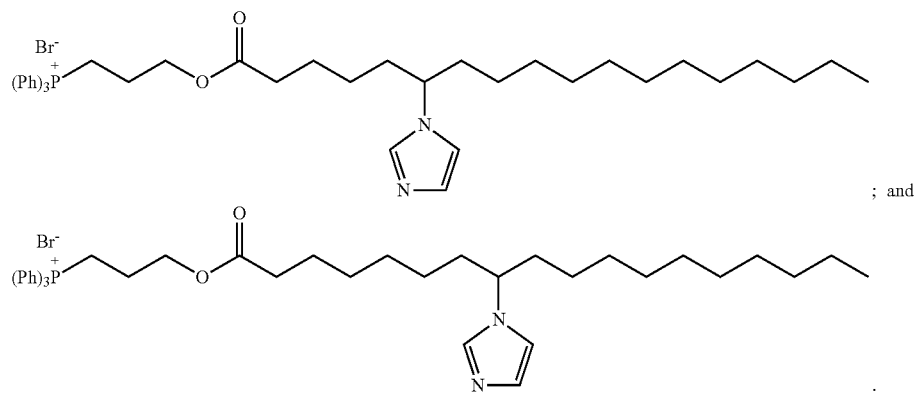

; and

13. A composition comprising one or more compounds of claim 1, and at least one carrier.

14. A pharmaceutical composition comprising one or more compounds of claim 1 and at least one pharmaceutically acceptable carrier.

15. A method to inhibit cytochrome c (cyt c) peroxidase comprising administering an effective amount of one or more compounds of claim 1 to a cell or subject in need thereof.

16. A method to prevent or treat apoptosis comprising administering an effective amount of one or more compounds of claim 1 to a cell or subject in need thereof.

17. The method of claim 16, wherein the apoptosis is mitochondria-dependent apoptosis.

18. The method of claim 16, wherein the apoptosis is radiation induced apoptosis.

19. The method of claim 18, wherein the radiation induced apoptosis is caused by exposure of the subject or cell to full-body irradiation (for example, for bone marrow transplantation), clinical radiation therapy (for example for cancer therapy to protect healthy cells) or accidental radiation exposure.

20. The method of claim 16, wherein the apoptosis is induced by subjecting a cell to a freeze/thaw cycle.

21. The method of claim 16, wherein the apoptosis is induced by ischemia.

* * * * *